(12) United States Patent
Rivella et al.

(10) Patent No.: US 11,311,632 B2
(45) Date of Patent: Apr. 26, 2022

(54) VIRAL VECTORS FOR PROPHYLAXIS AND THERAPY OF HEMOGLOBINOPATHIES

(71) Applicants: Cornell University, Ithaca, NY (US); The Children's Hospital of Philadelphia, Philadelphia, PA (US)

(72) Inventors: Stefano Rivella, New York, NY (US); Laura Breda, New York, NY (US); Alisa Dong, New York, NY (US); Gerd Blobel, Bala Cynwyd, PA (US); Wulan Deng, Ashburn, VA (US)

(73) Assignees: CORNELL UNIVERSITY, Ithaca, NY (US); THE CHILDREN'S HOSPITAL OF PHILADELPHIA, Philadelphia, PA (US)

( * ) Notice: Subject to any disclaimer, the term of this patent is extended or adjusted under 35 U.S.C. 154(b) by 0 days.

(21) Appl. No.: 15/545,159

(22) PCT Filed: Jan. 21, 2016

(86) PCT No.: PCT/US2016/014269
§ 371 (c)(1),
(2) Date: Jul. 20, 2017

(87) PCT Pub. No.: WO2016/118715
PCT Pub. Date: Jul. 28, 2016

(65) Prior Publication Data
US 2018/0008725 A1    Jan. 11, 2018

Related U.S. Application Data

(60) Provisional application No. 62/105,829, filed on Jan. 21, 2015.

(51) Int. Cl.
| | | |
|---|---|---|
| C12N 15/00 | (2006.01) | |
| A61K 39/00 | (2006.01) | |
| A61K 48/00 | (2006.01) | |
| C12N 15/86 | (2006.01) | |
| C12N 15/867 | (2006.01) | |

(52) U.S. Cl.
CPC ............ *A61K 48/005* (2013.01); *C12N 15/86* (2013.01); *C12N 15/867* (2013.01); *C12N 2740/15043* (2013.01); *C12N 2830/40* (2013.01); *C12N 2830/48* (2013.01); *C12N 2830/50* (2013.01); *C12N 2830/52* (2013.01)

(58) Field of Classification Search
None
See application file for complete search history.

(56) References Cited

U.S. PATENT DOCUMENTS

| | | | | |
|---|---|---|---|---|
| 7,541,179 B2* | 6/2009 | Sadelain | ............ | A61K 48/0066 |
| | | | | 424/93.2 |
| 7,901,671 B2* | 3/2011 | Leboulch | ............ | A01K 67/0278 |
| | | | | 424/93.2 |
| 8,058,061 B2* | 11/2011 | Sadelain | ............ | A61K 48/0066 |
| | | | | 435/320.1 |
| 9,068,199 B2* | 6/2015 | Leboulch | ............ | A01K 67/0278 |
| 2009/0124566 A1 | 5/2009 | Chi et al. | | |
| 2012/0009161 A1 | 1/2012 | Leboulch et al. | | |
| 2012/0039932 A1 | 2/2012 | Allen et al. | | |
| 2015/0224209 A1* | 8/2015 | Kohn | ............ | A61K 48/0066 |
| | | | | 424/93.21 |
| 2018/0051059 A1* | 2/2018 | Blobel | ............ | C07K 14/47 |

FOREIGN PATENT DOCUMENTS

| | | |
|---|---|---|
| WO | 2004/083383 A2 | 9/2004 |
| WO | 2011/011584 A1 | 1/2011 |
| WO | 2013184197 A1 | 12/2013 |
| WO | 2014/043131 A1 | 3/2014 |

OTHER PUBLICATIONS

Helmut et al The Physiology of Tran sf errin and Transferrin Receptors Physiol. Rev. 67, 520-582 (1987).*
Li et al., Transferrin therapy ameliorates disease in ��-thalassemic mice (2010; Nature Medicine, pp. 177-183).*
Abelson et al., tRNA Splicing Minireview The Journal of Biological Chemistry vol. 273, No. 21, Issue of May 22, pp. 12685-12688, 1998.*
http://www.web-books.com/MoBio/Free/Ch5A4.htm; pp. 1-5, downloaded Feb. 4, 2019.*
Complementary DNA—Wikipedia; pp. 1-3; downloaded on Feb. 4, 2019.*
Drakopoulou et al., Towards More Successful Gene Therapy Clinical Trials for beta-Thalassemia Current Molecular Medicine 2013, 13, 1314-1330.*
Musallam, K.M., et al., "Non-transfusion-dependent thalassemias" Haematologica (2013) 98(6):833-44.

(Continued)

*Primary Examiner* — Maria G Leavitt
(74) *Attorney, Agent, or Firm* — Robert C. Netter, Jr.; Dann, Dorfman, Herrell & Skillman

(57) ABSTRACT

Provided are compositions and methods for inducing expression of human beta-globin in erythrocytes for use in prophylaxis and/or therapy of a hemoglobinopathy in an individual. The method generally entails introducing into CD34+ cells a poly-nucleotide encoding: i) a 5' long terminal repeat (LTR) and a self-inactivating 3' LTR; ii) at least one polyadenylation signal; iii) at least one promoter; iv) a globin gene locus control region (LCR); v) an ankyrin insulator element (Ank); vi) a Woodchuck Post-Regulatory Element (WPRE) configured such that the WPRE does not integrate into a target genome; and vii) a sequence that is a reverse complement of a sequence encoding human beta-globin, and can include beta-globin that has a PT87Q mutation. Intron 2 of the beta globin gene can be a complete intron. Modified erythrocyte progenitor cells, recombinant vectors and virions comprising recombinant polynucleotides, and methods of making the vectors and virions are included.

19 Claims, 43 Drawing Sheets

Specification includes a Sequence Listing.

(56) References Cited

OTHER PUBLICATIONS

Rivella, S., "The role of ineffective erythropoiesis in non-transfusion-dependent thalassemia" Blood Rev. (2012) 26 Suppl 1:S12-5.
Ginzburg, Y., et al., "β-thalassemia: a model for elucidating the dynamic regulation of ineffective erythropoiesis and iron metabolism" Blood (2011) 118(16):4321-30.
May, C., et al., "Successful treatment of murine beta-thalassemia intermedia by transfer of the human beta-globin gene" Blood (2002) 99(6):1902-8.
May, C., et al., "Therapeutic haemoglobin synthesis in beta-thalassaemic mice expressing lentivirus-encoded human beta-globin" Nature (2000) 406(6791):82-6.
Rivella, S., et al., "A novel murine model of Cooley anemia and its rescue by lentiviral-mediated human beta-globin gene transfer" Blood (2003) 101(8):2932-9.
Breda, L., et al., "Therapeutic hemoglobin levels after gene transfer in β-thalassemia mice and in hematopoietic cells of β-thalassemia and sickle cells disease patients" PLoS One (2012) 7(3):e32345.
Pawliuk, R., et al., "Correction of sickle cell disease in transgenic mouse models by gene therapy" Science (2001) 294(5550):2368-71.
Cavazzana-Calvo, M., et al., "Transfusion independence and HMGA2 activation after gene therapy of human β-thalassaemia" Nature (2010) 467(7313):318-22.
Samakoglu, S., et al., "A genetic strategy to treat sickle cell anemia by coregulating globin transgene expression and RNA interference" Nat. Biotechnol. (2006) 24(1):89-94.
Deng, W., et al., "Reactivation of developmentally silenced globin genes by forced chromatin looping" Cell (2014) 158(4):849-860.
Antoniou, M., et al., Efficient 3'-end formation of human beta-globin mRNA in vivo requires sequences within the last intron but occurs independently of the splicing reaction. Nucleic Acids Research, Feb. 1998, vol. 26, No. 3, pp. 721-729.
El-Rashidi, F.H., et al., The role of soluble transferrin receptor in iron overload in children with chronic hemolytic anemia, Menoufia Medical Journal, 2013, vol. 26, No. 2, pp. 132-137.
Negre, O., et al., "Gene Therapy of the β-Hemoglobinopathies by Lentiviral Transfer of the β(A(T87Q))-Globin Gene" Hum Gene Ther. (2016) 27(2):148-65.
Bokinni, et al., "Producing and evaluating a novel lentiviral vector for beta-thalassaemia gene therapy" BMC Proceedings (2012) 6(Suppl 4):O15.
Leboulch, P., et al., "Mutagenesis of retroviral vectors transducing human beta-globin gene and beta-globin locus control region derivatives results in stable transmission of an active transcriptional structure" EMBO J. (1994) 13(13):3065-76.
Arumugam, P., et al., "Genetic Therapy for Beta-Thalassemia: From the Bench to the Bedside" Hematology Am. Soc. Hematol. Educ. Program (2010) 2010(1):445-450.

\* cited by examiner

Figure 13

```
5'  cgcgttcgaaggggcaaccaggggtccgcgcgccgaggcctggggagcgggcctcctgg
                                                                    60
    |_____Ank Promoter_____|

5'  ggttgggggaggaggtgctcttgtaatctgcggtggtccccaggcgggcgccacccctcc
                                                                    120
                              Ank Promoter 5'  gcccgcccgtgccgggagcgcccggcccgacagcaagcgcctctggggccgataaggccc
                                                                    180
                              Ank Promoter 5'  tcggggggcctggccccgcacgtcacaggccccgcagaggctgcggtgagtccgccagcccc
                                                                    240
                              Ank Promoter 5'  agctgctcctcctcaagccccccaaggcccttcggcggcaattcccaccggtcgccaccAT
                                                                    300
    |_____Ank Promoter_____|  M
                                                                     1

5'  GGCCCAGGCGGCCCTTGGAGCCCGGAGAGAAACCCTACAAATGCCCCGGAGTGTGGAAAGTC
                                                                    360
                              GG1-ZF
     A  Q  A  A  L  E  P  G  E  K  P  Y  K  C  P  E  C  G  K  S
     2  3  4  5  6  7  8  9  10 11 12 13 14 15 16 17 18 19 20 21
```

Figure 13, continued

```
5'  CTTCAGCGACTGTAGGGACCTGGCACGCCACCAGCGAACCCACACAGGCGAGAAGCCCTA
                                                                          420
                            GG1-ZF
     F  S  D  C  R  D  L  A  R  H  Q  R  T  H  T  G  E  K  P  Y
     22 23 24 25 26 27 28 29 30 31 32 33 34 35 36 37 38 39 40 41

5'  TAAATGTCCAGAGTGTGGAAAGAGCTTCTCTAGAAACGATGCACTGACTGAGCACCAACG
                                                                          480
                            GG1-ZF
     K  C  P  E  C  G  K  S  F  S  R  N  D  A  L  T  E  H  Q  R
     42 43 44 45 46 47 48 49 50 51 52 53 54 55 56 57 58 59 60 61

5'  CACCCATACCGGGGAAAAACCTTATAAATGTCCTGAGTGTGGTAAAAGTTTTTCTCAATT
                                                                          540
                            GG1-ZF
     T  H  T  G  E  K  P  Y  K  C  P  E  C  G  K  S  F  S  Q  L
     62 63 64 65 66 67 68 69 70 71 72 73 74 75 76 77 78 79 80 81

5'  GGCTCATCTCCGCGCTCACCAACGCACGCATACTGGTGAGAAGCCCTATAAGTGCCCCGA
                                                                          600
                            GG1-ZF
     A  H  L  R  A  H  Q  R  T  H  T  G  E  K  P  Y  K  C  P  E
     82 83 84 85 86 87 88 89 90 91 92 93 94 95 96 97 98 99 100 101

5'  ATGCGGCAAGAGTTTTTCTCAAAGCGGGGACCTTAGAAGACACCAAAGAACCCATACCGG
                                                                          660
                            GG1-ZF
     C  G  K  S  F  S  Q  S  G  D  L  R  R  H  Q  R  T  H  T  G
     102 103 104 105 106 107 108 109 110 111 112 113 114 115 116 117 118 119 120 121
```

Figure 13, continued

```
5'  CGAAAAACCTTACAAGTGTCCCGAGTGCGGAAAATCTTTTTCACGCAAAGACAATTTGAA
                                                                              720
                              GG1-ZF
      E   K   P   Y   K   C   P   E   C   G   K   S   F   S   R   K   D   N   L   K
     122 123 124 125 126 127 128 129 130 131 132 133 134 135 136 137 138 139 140 141

5'  GAACCACCAGCGGACACACACCGGTGAAAAGCCTTACAAATGTCCCGAATGTGGCAAGTC
                                                                              780
                              GG1-ZF
      N   H   Q   R   T   H   T   G   E   K   P   Y   K   C   P   E   C   G   K   S
     142 143 144 145 146 147 148 149 150 151 152 153 154 155 156 157 158 159 160 161

5'  ATTCTCAGACCCCGGAGCCCTGGTGCGCCATCAGCGCACTCACACTGGCAAGAAGACTAG
                                                                              840
                              GG1-ZF
      F   S   D   P   G   A   L   V   R   H   Q   R   T   H   T   G   K   K   T   S
     162 163 164 165 166 167 168 169 170 171 172 173 174 175 176 177 178 179 180 181

5'  CGGCCAGGCCGGCCAGGCTAGCCCCGAAAAAGAAACGCAAAGTTGggcgcgcCCTGGATCG
                                                                              900
                              GG1-ZF                                |DDi-LDB1|
      G   Q   A   G   Q   A   S   P   K   K   K   R   K   V   G   R   A   L   D   R
     182 183 184 185 186 187 188 189 190 191 192 193 194 195 196 197 198 199 200 201

5'  GGATGTGGGCCCAACTCCCATGTACCCACCTACATACCTGGAGCCTGGGATCGGGAGGCA
                                                                              960
                              DDi-LDB1
      D   V   G   P   T   P   M   Y   P   P   T   Y   L   E   P   G   I   G   R   H
     202 203 204 205 206 207 208 209 210 211 212 213 214 215 216 217 218 219 220 221
```

Figure 13, continued

```
5' CACACCATATGGTAACCAAACCGACTATAGAATATTTGAGCTTAACAAACGGCTACAGAA
                                                                      1020
                              DDI-LDB1
     T  P  Y  G  N  Q  T  D  Y  R  I  F  E  L  N  K  R  L  Q  N
    222 223 224 225 226 227 228 229 230 231 232 233 234 235 236 237 238 239 240 241

5' CTGGACAGAGGAGTGTGACAATCTCTGGTGGGATGCTTTCACAACTGAGTTCTTTGAAGA
                                                                      1080
                              DDI-LDB1
     W  T  E  E  C  D  N  L  W  W  D  A  F  T  T  E  F  F  E  D
    242 243 244 245 246 247 248 249 250 251 252 253 254 255 256 257 258 259 260 261

5' TGACGCCATGCTGACCATCACTTTCTGCTTGGAGGATGGACCAAAGAGATATACCATTGG
                                                                      1140
                              DDI-LDB1
     D  A  M  L  T  I  T  F  C  L  E  D  G  P  K  R  Y  T  I  G
    262 263 264 265 266 267 268 269 270 271 272 273 274 275 276 277 278 279 280 281

5' CCCGGACCCTGATACCACGCTACTTCCGAAGCATTTTTGAGGGGGGTGCCACAGAGCTGTA
                                                                      1200
                              DDI-LDB1
     R  T  L  I  P  R  Y  F  R  S  I  F  E  G  G  A  T  E  L  Y
    282 283 284 285 286 287 288 289 290 291 292 293 294 295 296 297 298 299 300 301

5' CTACGTGCTCAAGCACCCCAAGGAGGCATTCCACAGCAACTTCGTGTCCCTCGACTGTGA
                                                                      1260
                              DDI-LDB1
     Y  V  L  K  H  P  K  E  A  F  H  S  N  F  V  S  L  D  C  D
    302 303 304 305 306 307 308 309 310 311 312 313 314 315 316 317 318 319 320 321
```

Figure 13, continued

```
5'  CCAGGGCAGCATGGTGACCCAGCACGGCAAACCCATGTTTACCCAGGTGTGTGTGGAAGG
                                                                        1320
                        DDI-LDB1
     Q  G  S  M  V  T  Q  H  G  K  P  M  F  T  Q  V  C  V  E  G
    322 323 324 325 326 327 328 329 330 331 332 333 334 335 336 337 338 339 340 341

5'  CCGGTTGTACCTGGAGTTCATGTTTGACGACATGATGCGGATAAAGACGTGGCACTTCAG
                                                                        1380
                        DDI-LDB1
     R  L  Y  L  E  F  M  F  D  D  M  M  R  I  K  T  W  H  F  S
    342 343 344 345 346 347 348 349 350 351 352 353 354 355 356 357 358 359 360 361

5'  CATCCGGCAACACAGAGAGCTCATCCCCAGAAGTATCCTGGCCATGCACGCCCAGGACCC
                                                                        1440
                        DDI-LDB1
     I  R  Q  H  R  E  L  I  P  R  S  I  L  A  M  H  A  Q  D  P
    362 363 364 365 366 367 368 369 370 371 372 373 374 375 376 377 378 379 380 381

5'  CCAGATGCTGGATCAGCTGTCCAAAAACATTACCCGGTGTGGGCTGTCCTTAATTAACTA
                                                                        1500
                        DDI-LDB1
     Q  M  L  D  Q  L  S  K  N  I  T  R  C  G  L  S  L  I  N  Y
    382 383 384 385 386 387 388 389 390 391 392 393 394 395 396 397 398 399 400 401

5'  CCCGTACGACGTTCCGGACTACGCTTCTTGAatcggtaggaattaattctgcagcggccg
                                                                        1560
                HA
     P  Y  D  V  P  D  Y  A  S
    402 403 404 405 406 407 408 409 410 411
```

Figure 13, continued

```
5' cggatccgcccctctccctcccccccccctaacgttactggccgaagccgcttggaataa
                                                                    1620
              EMCV-IRES 5' ggccggtgtgcgtttgtctatatgttattttccaccatattgccgtcttttggcaatgtg
                                                                    1680
              EMCV-IRES 5' agggcccggaaacctggccctgtcttcttgacgagcattcctaggggtctttcccctctc
                                                                    1740
              EMCV-IRES 5' gccaaaggaatgcaaggtctgttgaatgtcgtgaaggaagcagttcctctggaagcttct
                                                                    1800
              EMCV-IRES 5' tgaagacaaacaacgtctgtagcgaccctttgcaggcagcggaaccccccacctggcgac
                                                                    1860
              EMCV-IRES 5' aggtgcctctgcggccaaaagccacgtgtataagatacacctgcaaaggcggcacaaccc
                                                                    1920
              EMCV-IRES 5' cagtgccacgttgtgagttggatagttgtggaaagagtcaaatggctctcctcaagcgta
                                                                    1980
              EMCV-IRES 5' ttcaacaaggggctgaaggatgcccagaaggtaccccattgtatgggatctgatctgggg
                                                                    2040
              EMCV-IRES
```

Figure 13, continued

```
5'  cctcggtgcacatgctttacatgtgtttagtcgaggttaaaaaaacgtctaggccccccg
                                                                    2100
                        EMCV-IRES 5'  aaccacggggacgtggttttcctttgaaaaacacgatgataatatggccacaaccatggt
                                                                    2160
                        EMCV-IRES                          EGFP 5'  gagcaagggcgaggagctgttcaccggggtggtgcccatcctggtcgagctggacggcga
                                                                    2220
                            EGFP 5'  cgtaaacggccacaagttcagcgtgtccggcgagggcgagggcgatgccacctacggcaa
                                                                    2280
                            EGFP 5'  gctgaccctgaagttcatctgcaccaccggcaagctgcccgtgccctggcccaccctcgt
                                                                    2340
                            EGFP 5'  gaccaccctgacctacggcgtgcagtgcttcagccgctaccccgaccacatgaagcagca
                                                                    2400
                            EGFP 5'  cgacttcttcaagtccgccatgcccgaaggctacgtccaggagcgcaccatcttcttcaa
                                                                    2460
                            EGFP 5'  ggacgacggcaactacaagacccgcgccgaggtgaagttcgagggcgacaccctggtgaa
                                                                    2520
                            EGFP
```

Figure 13, continued

```
5'  ccgcatcgagctgaagggcatcgacttcaaggaggacggcaacatcctggggcacaagct
                                                                    2580
                              EGFP 5'  ggagtacaactacaacagccacaacgtctatatcatggccgacaagcagaagaacggcat
                                                                    2640
                              EGFP 5'  caaggtgaacttcaagatccgccacaacatcgaggacggcagcgtgcagctcgccgacca
                                                                    2700
                              EGFP 5'  ctaccagcagaacacccccatcggcgacggccccgtgctgctgcccgacaaccactacct
                                                                    2760
                              EGFP 5'  gagcacccagtccgccctgagcaaagaccccaacgagaagcgcgatcacatggtcctgct
                                                                    2820
                              EGFP 5'  ggagttcgtgaccgccgcgggatcactctcggcatggacgagctgtacaagtaa
                                                                    2875
                              EGFP
```

Figure 14, continued
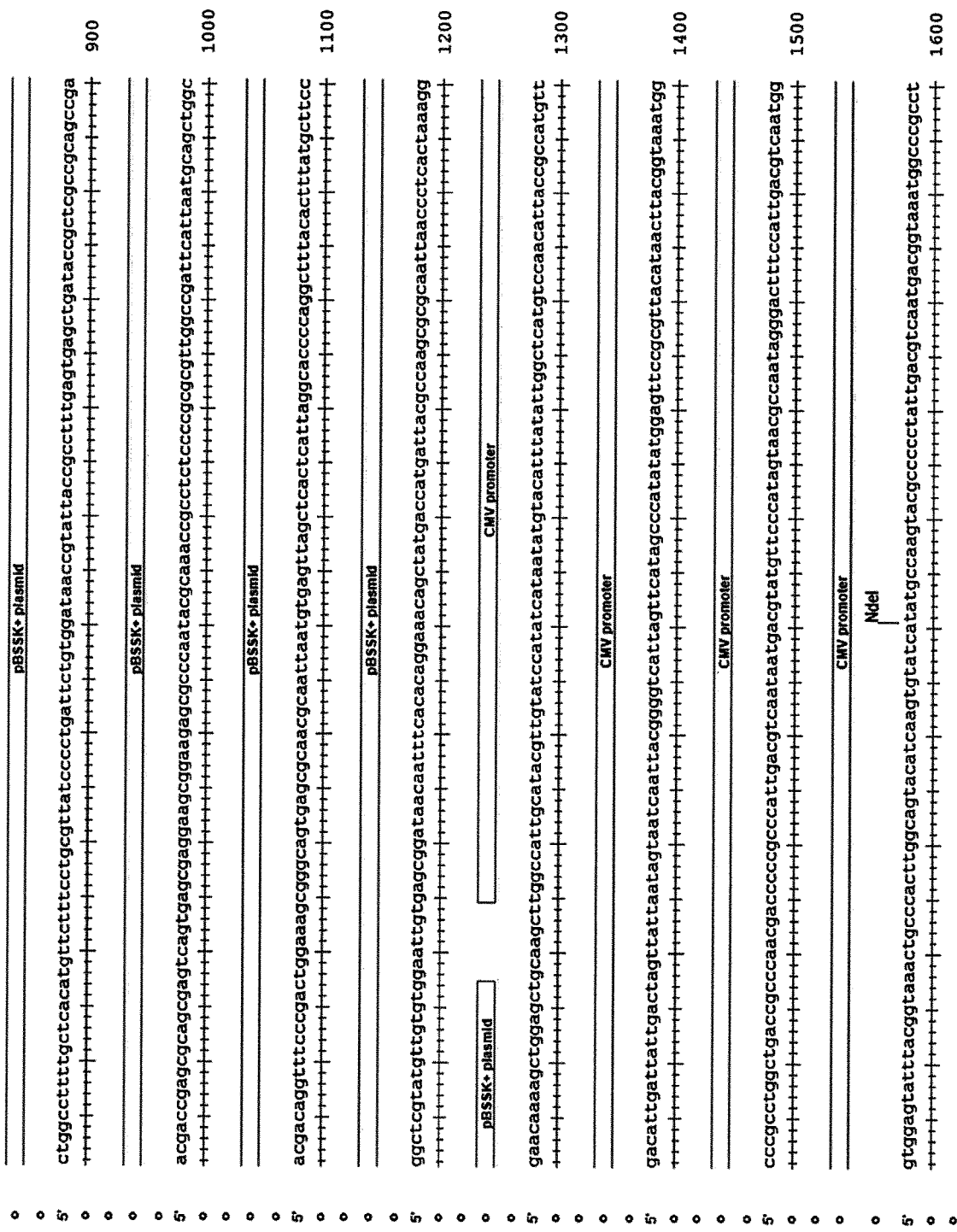

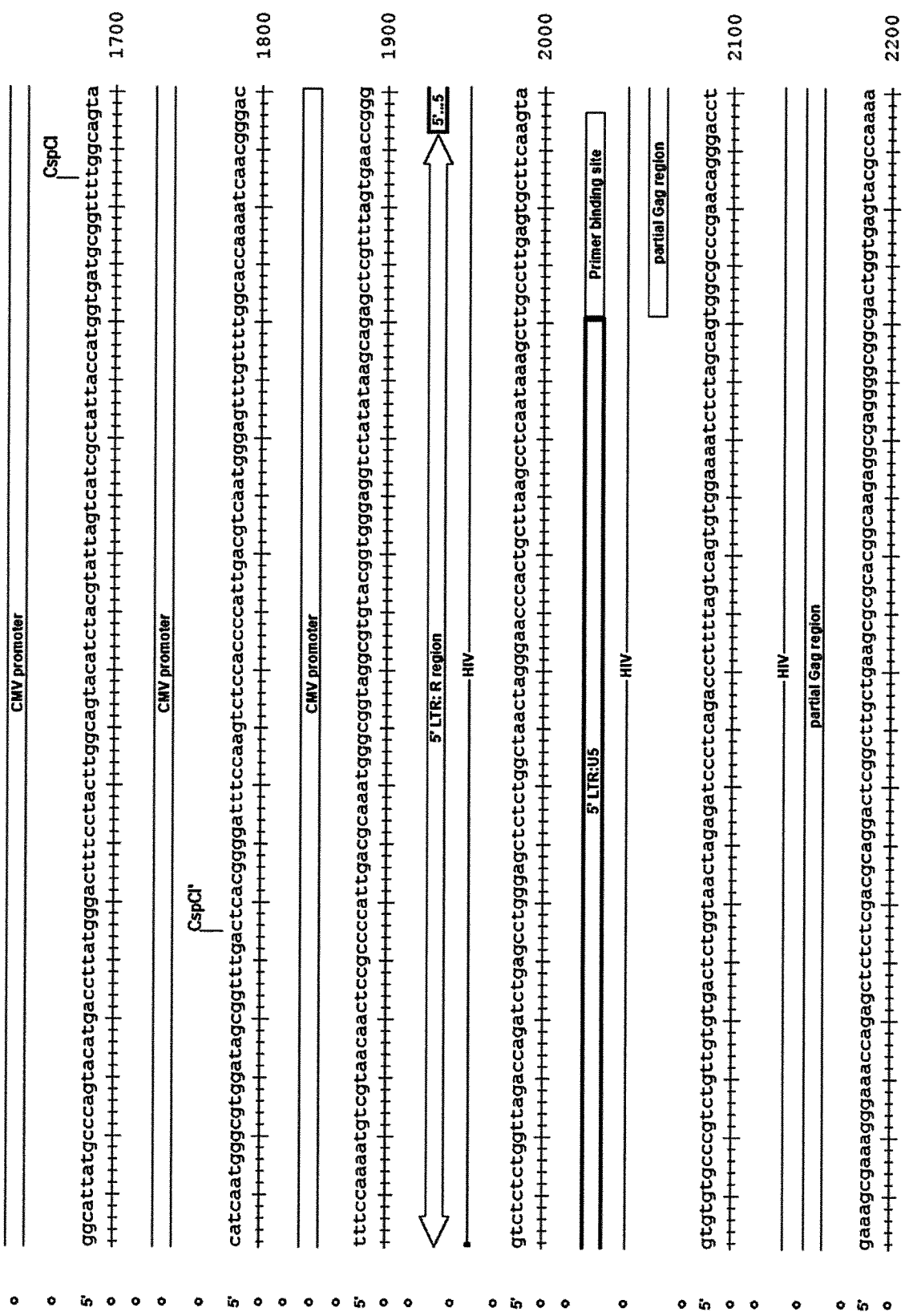
Figure 14, continued

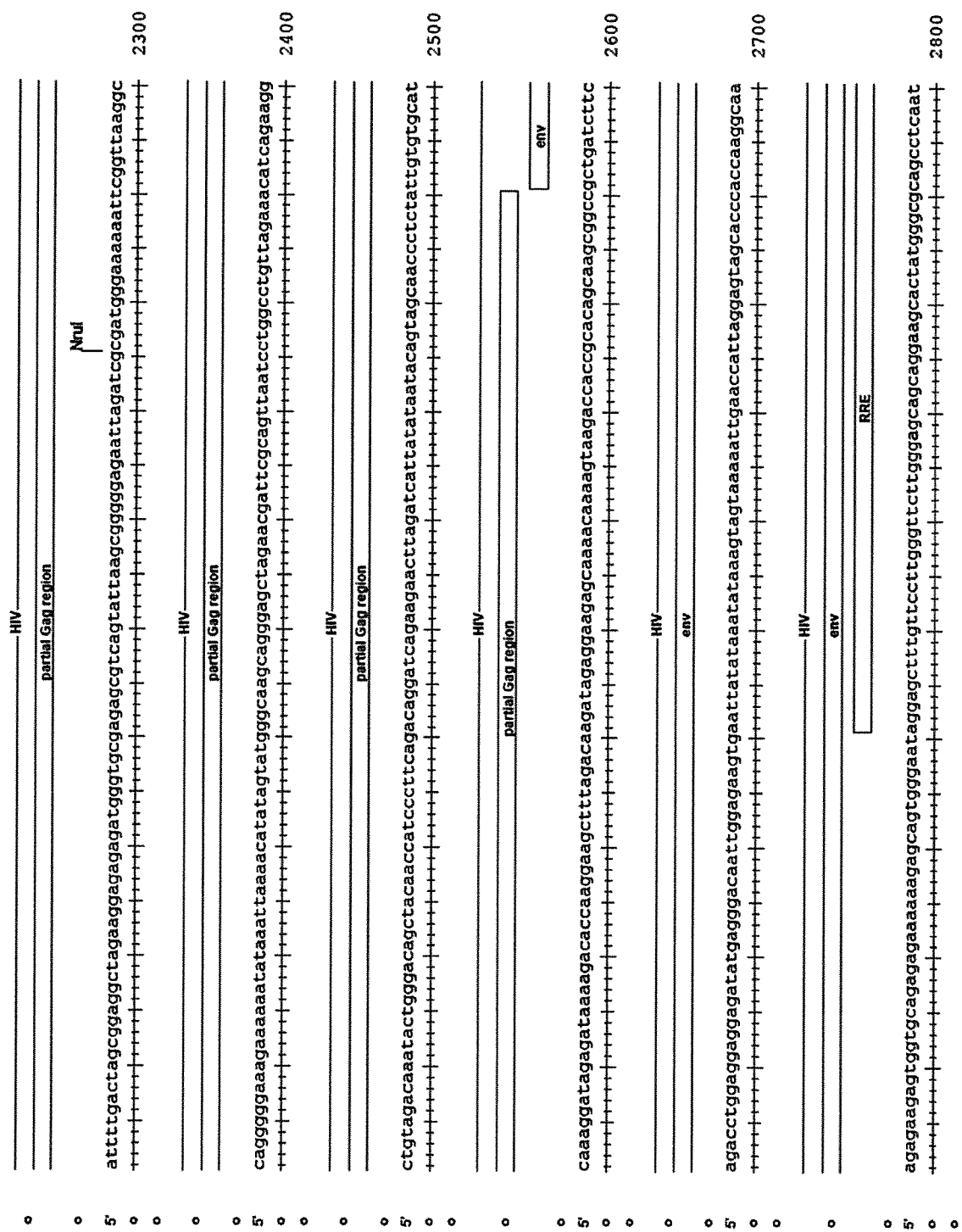
Figure 14, continued

Figure 14, continued

```
                                                                    2900
         gacgctgacgqtacaggccagacaattattgtctggtatagtgcagcagcagaacaatttgctgagggctattgaggcgcaacagcatctgttgcaactc
                                                            HIV
                                                            env
                                                            RRE 3000
         acagtcctggggcatcaagcagctccagcaagatcctggctgtggaaagatacctaaaggatcaacagctcctggggatttggggttgctcctggaaac
                                                            HIV
                                                            env
                                                        RRE 3100
         tcatttgcaccactgctgtgccttggaatgctagttggagtaataaatctctggaacagatttggaatcacacgacctgatgagtgggacagagaaat
                                                            HIV
                                                            env 3200
         taacaattacacaagcttaatacactccttaattgaagaatcgcaaaaccagcaagaaaagaatgaacaagaatattgaattagataaatgggcaagt
                                                            HIV
                                                            env 3300
         ttgtggaattggtttaacataacaattggctgtggtatataaaattattcataatgatagtaggaggcttggtaggtttaagaatagtttttgctgtac
                                                            HIV
                                                            env 3400
         tttctatagtgaatagagttaggcaggatattcaccattatgtttcagacccacctcccaaccccgaggggacccgacaggcccgaaggaatagaaga
                                                            HIV
                                                            env
```

Figure 14, continued
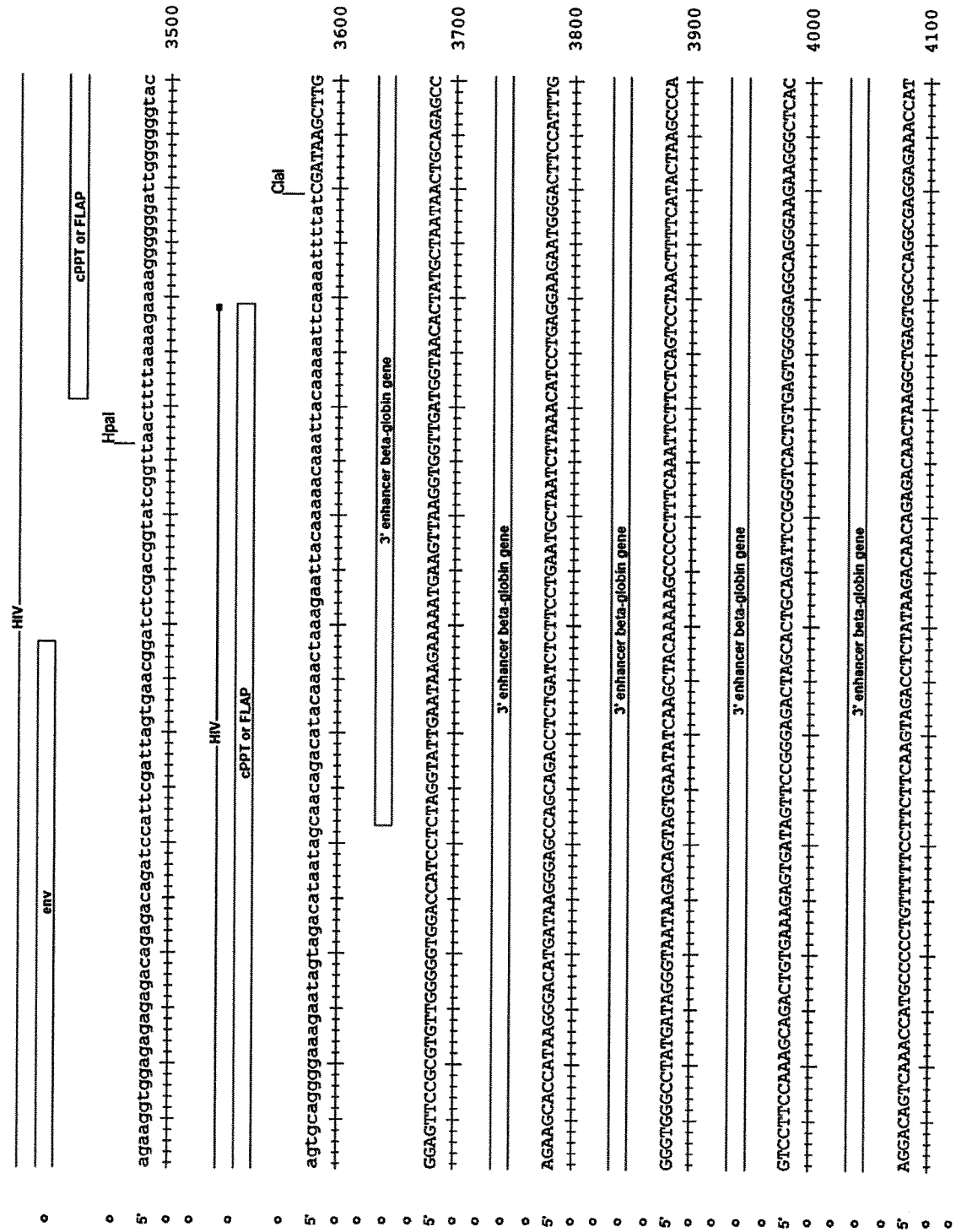

Figure 14, continued
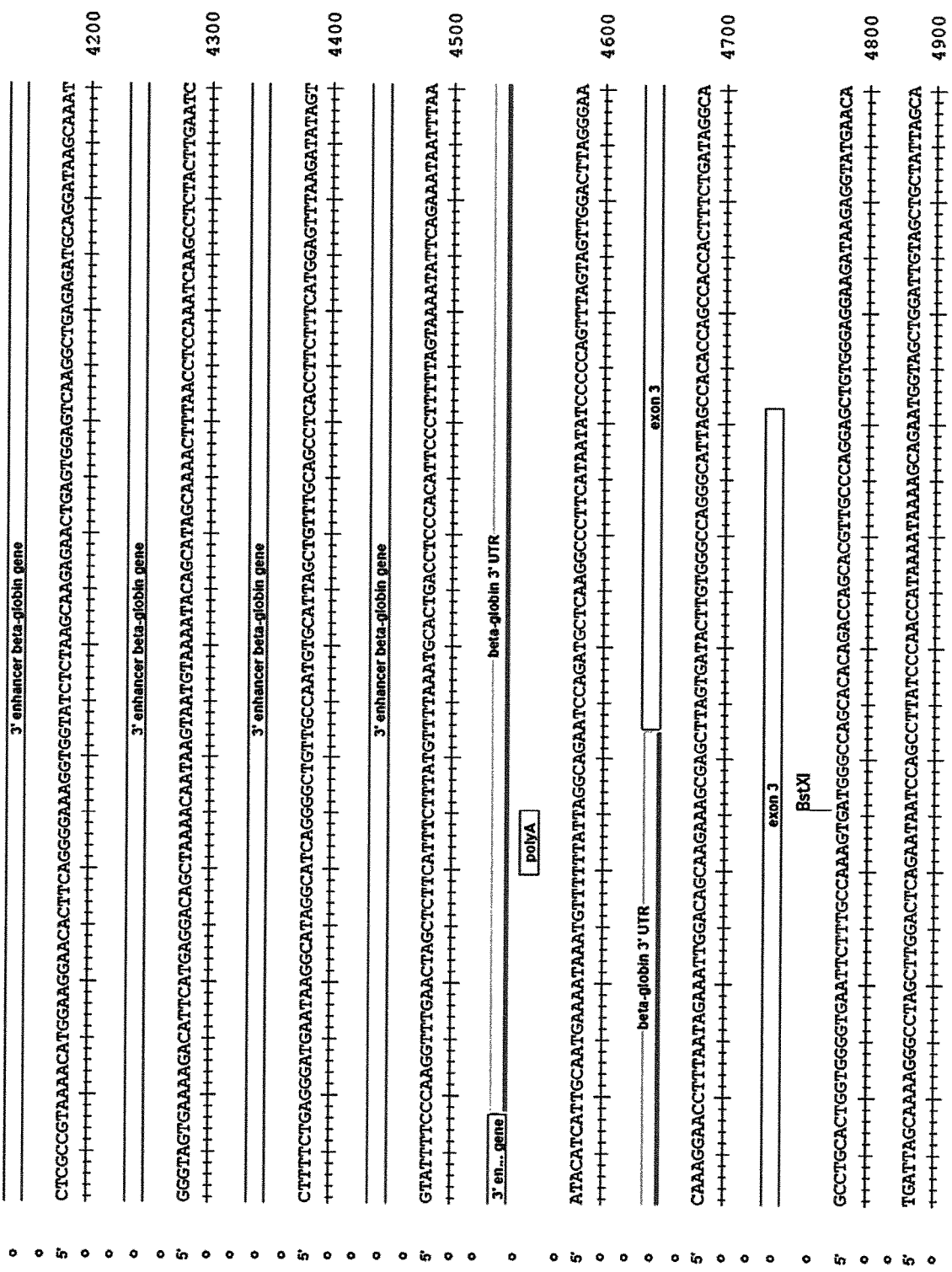

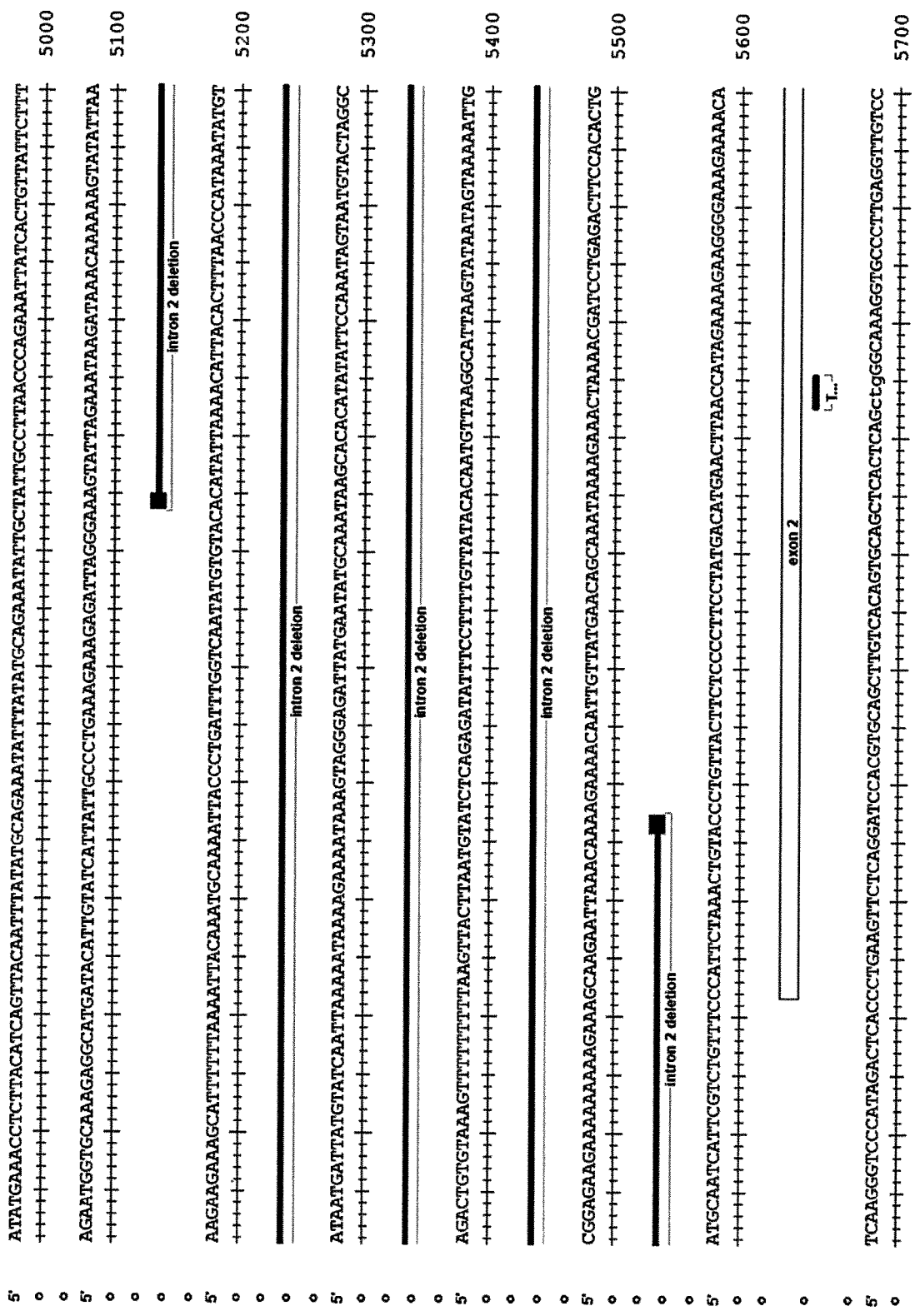
Figure 14, continued

Figure 14, continued
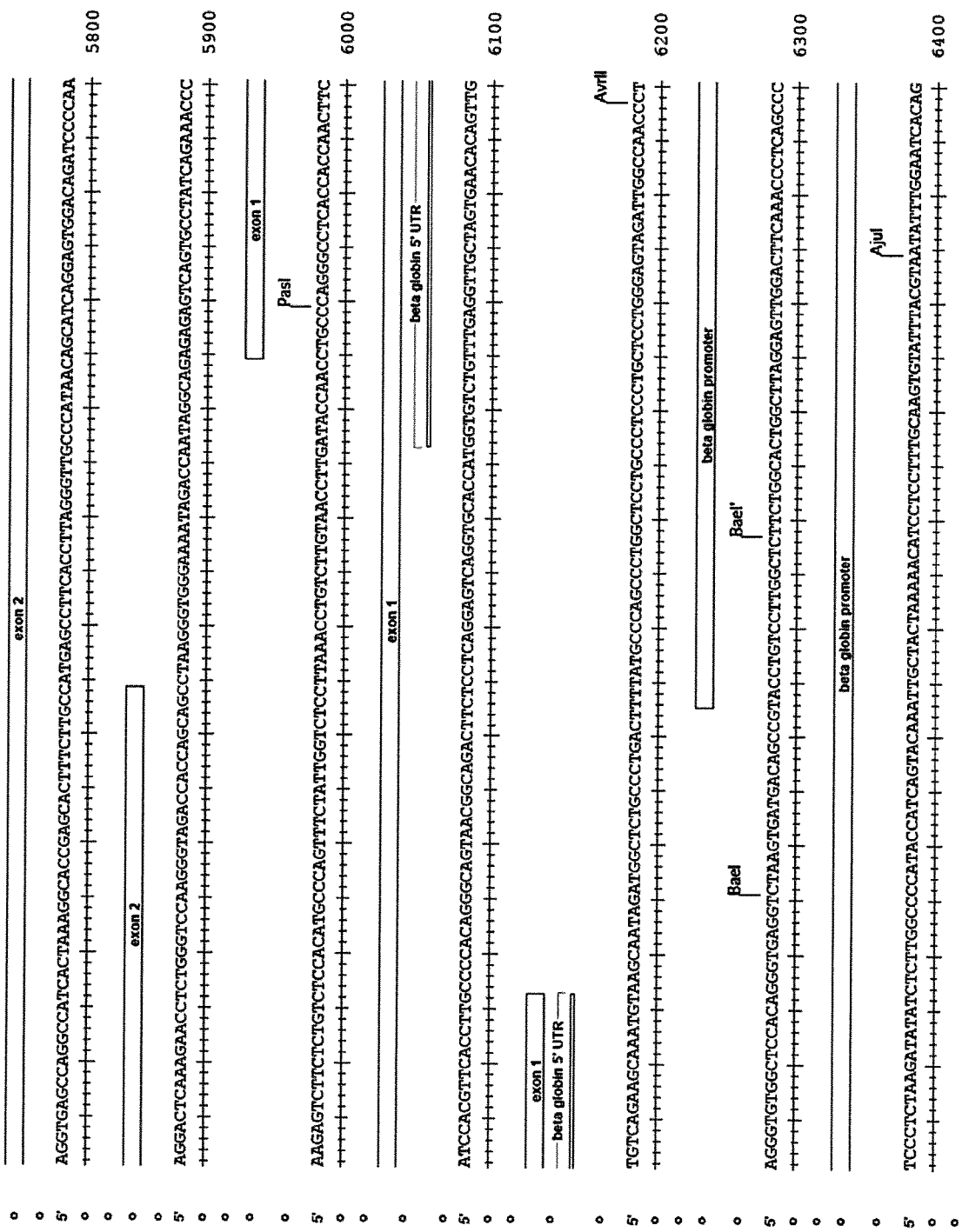

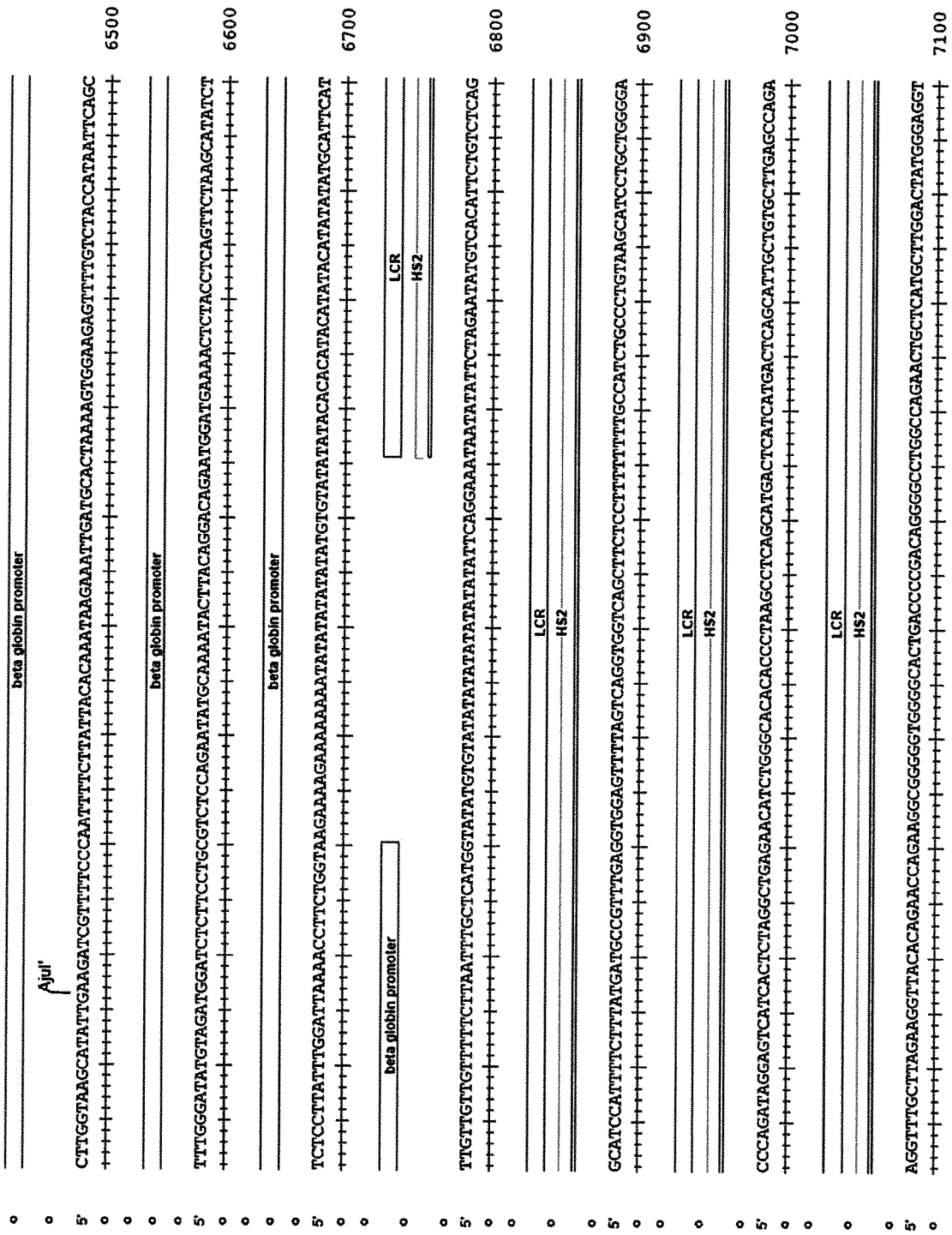
Figure 14, continued

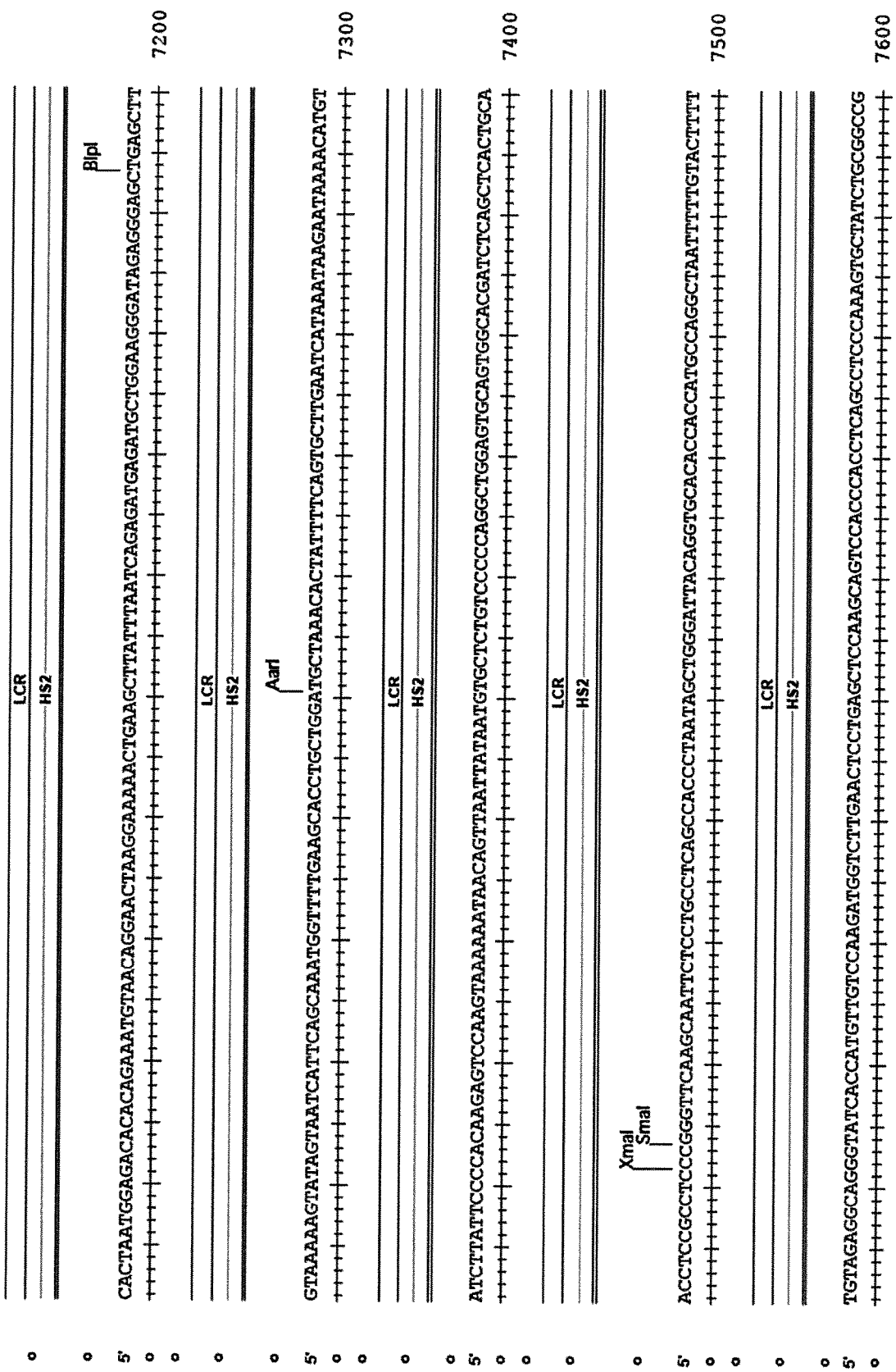
Figure 14, continued

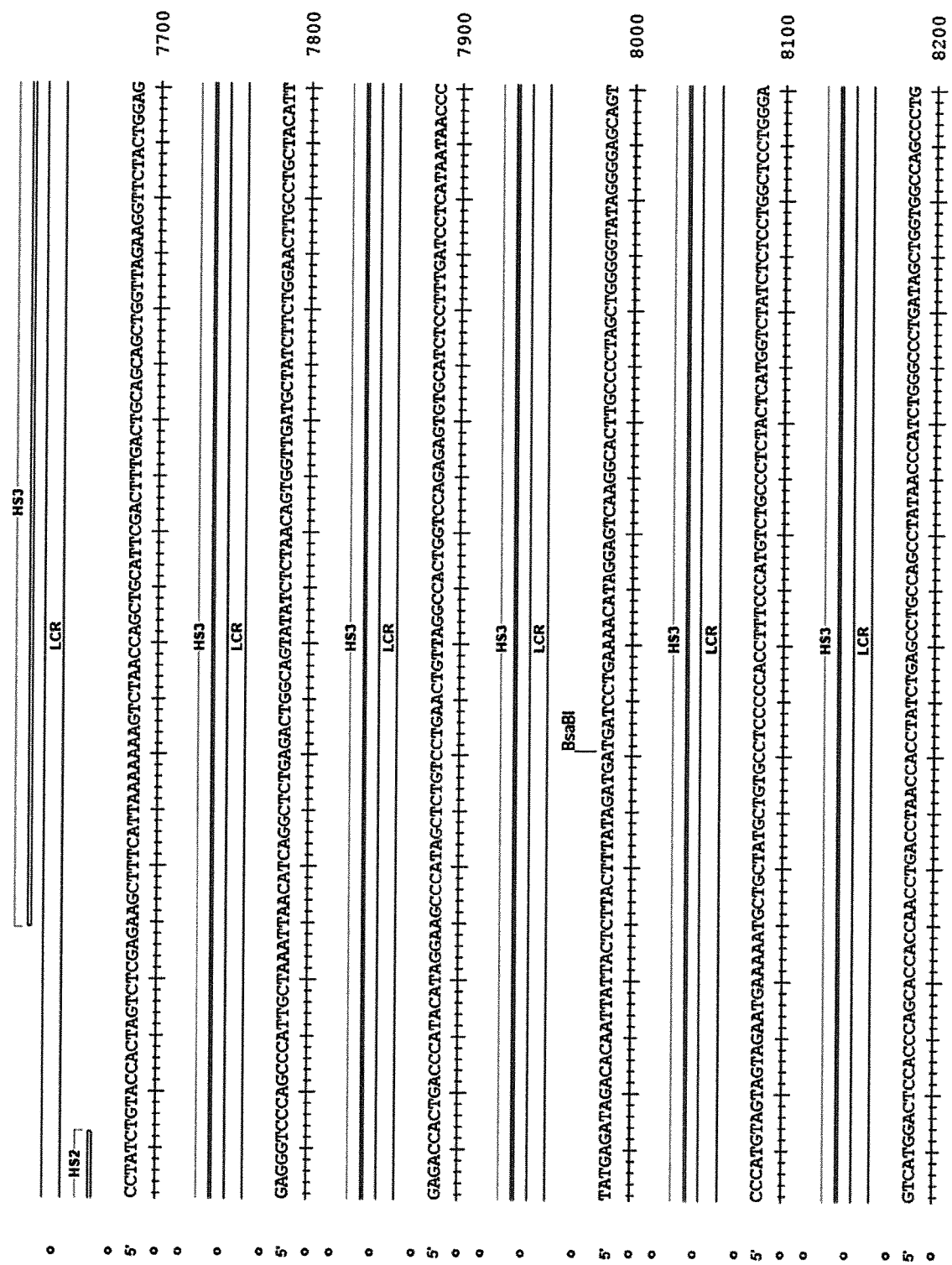
Figure 14, continued

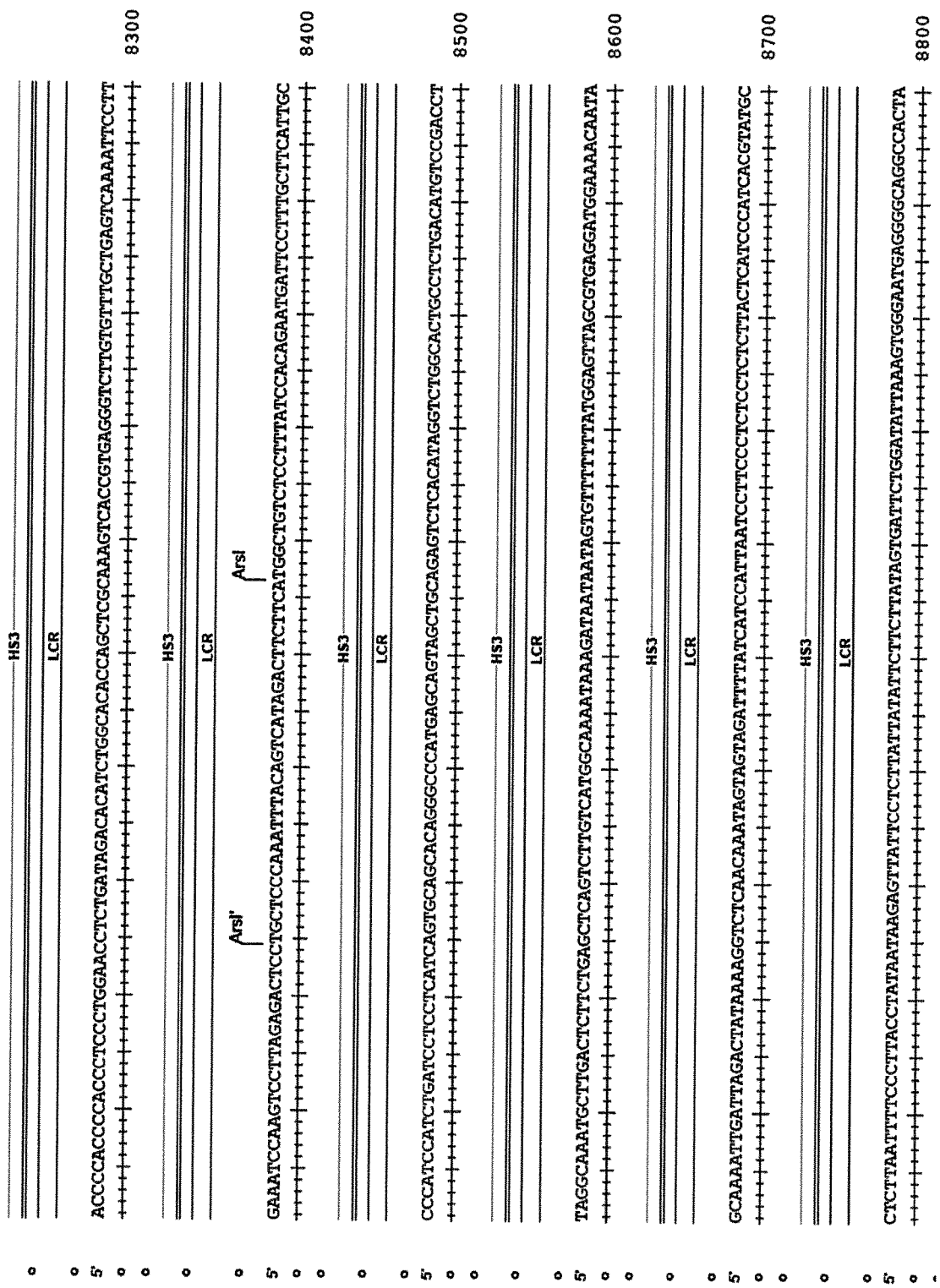
Figure 14, continued

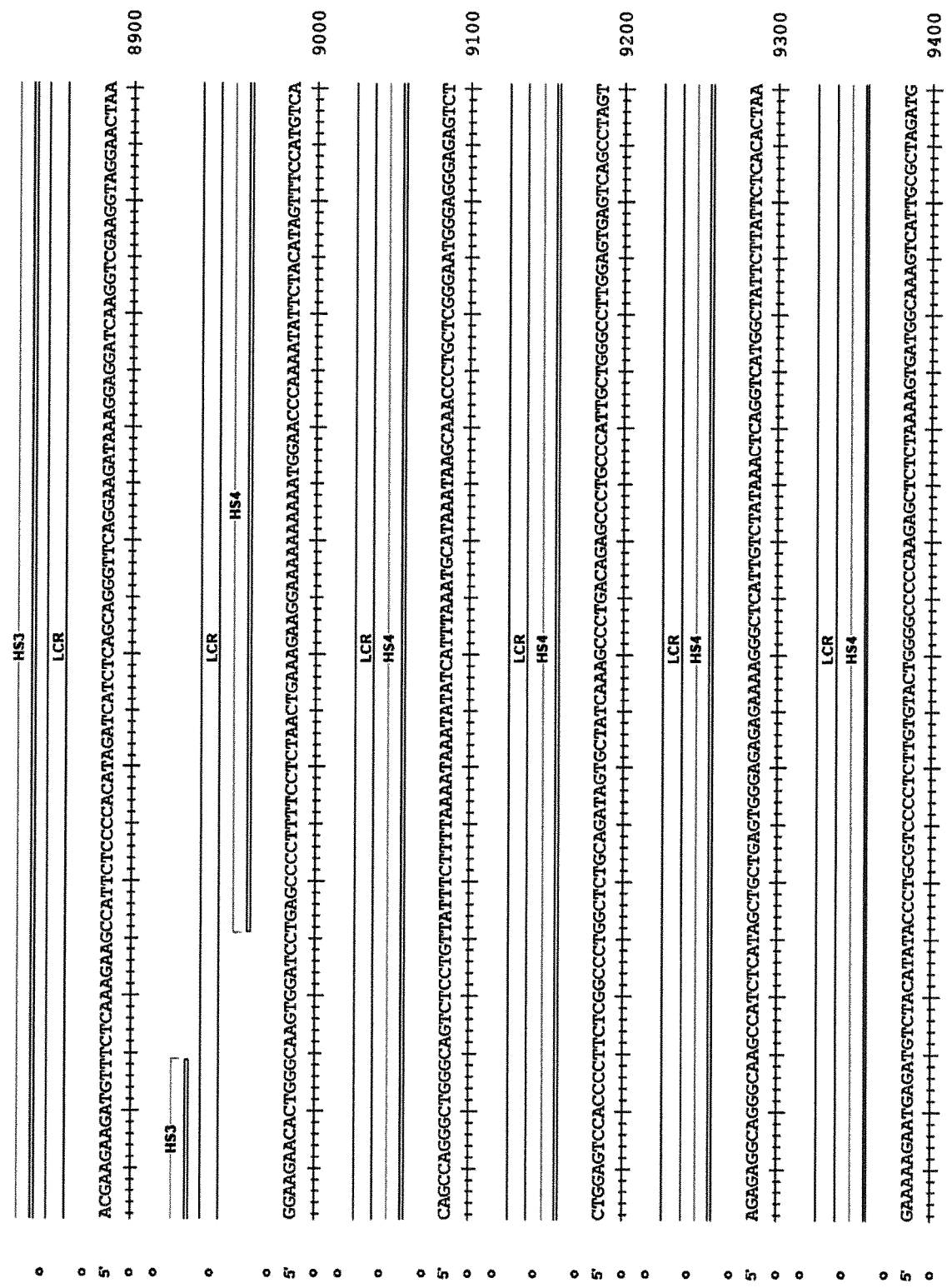
Figure 14, continued

Figure 14, continued

```
                                                                                              9500
     CCATCCCATCTATTATAAACCTGCATTTGTCTCCACACCAGTCATGGACAATAACCCTCCTCCCAGGTCCACGTGCTTGTCTTTGTATATATACTCAAG

9600
     TAATTTCGGAAAATGTATTCTTTCAATCTGTTCTGTTATTCCTGTTTCAATGGCTTAGTAGAAAAAGTACATACTTGTTTTCCCATAAATTGACAATAG

9700
     ACAATTTCACACATCAATGTCTATATGGGTCGTTGTGTTTGCAAAAACTCACAATAACTTTATATTGTTACTACTCTAAGAAAGTTACAACAT

9800
     GGTGAATACAAGAGAAAAGCTATTACAAGTCCAGAAAATAAAAGTTATCATCTTGAGGCCCTCAGCTTTCTAGGAATAATATCAATATTACAAAATTAATCT

9900
     AACAATTATGAACAGCAATGAGATAATATGTACAAAGTACCCAGACCTATGTGGTAGAGCATCAAGGAAGCGCATTGCGGAGCAGTTTTTGTTTGTTTG

10000
     TTTTTGTATTCTGTTTCGTTGAGGCAAGGTTTCACTCTGTCTGCTGTCCAGGCTGGAGTGCAGTGGCAAGATCATGTCTCACTGCAGCCTTGACACTacacgtgC
```

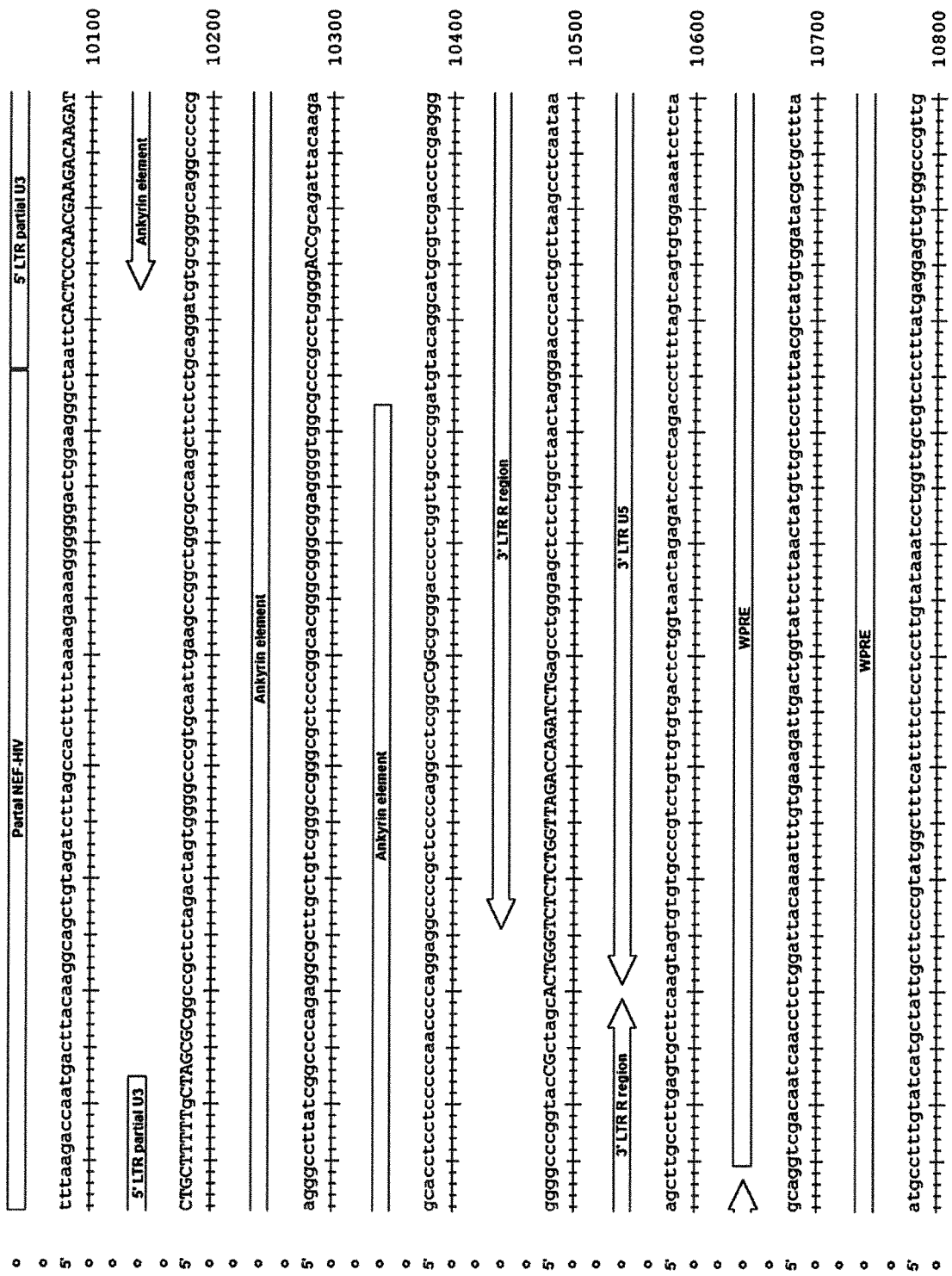
Figure 14, continued

Figure 14, continued
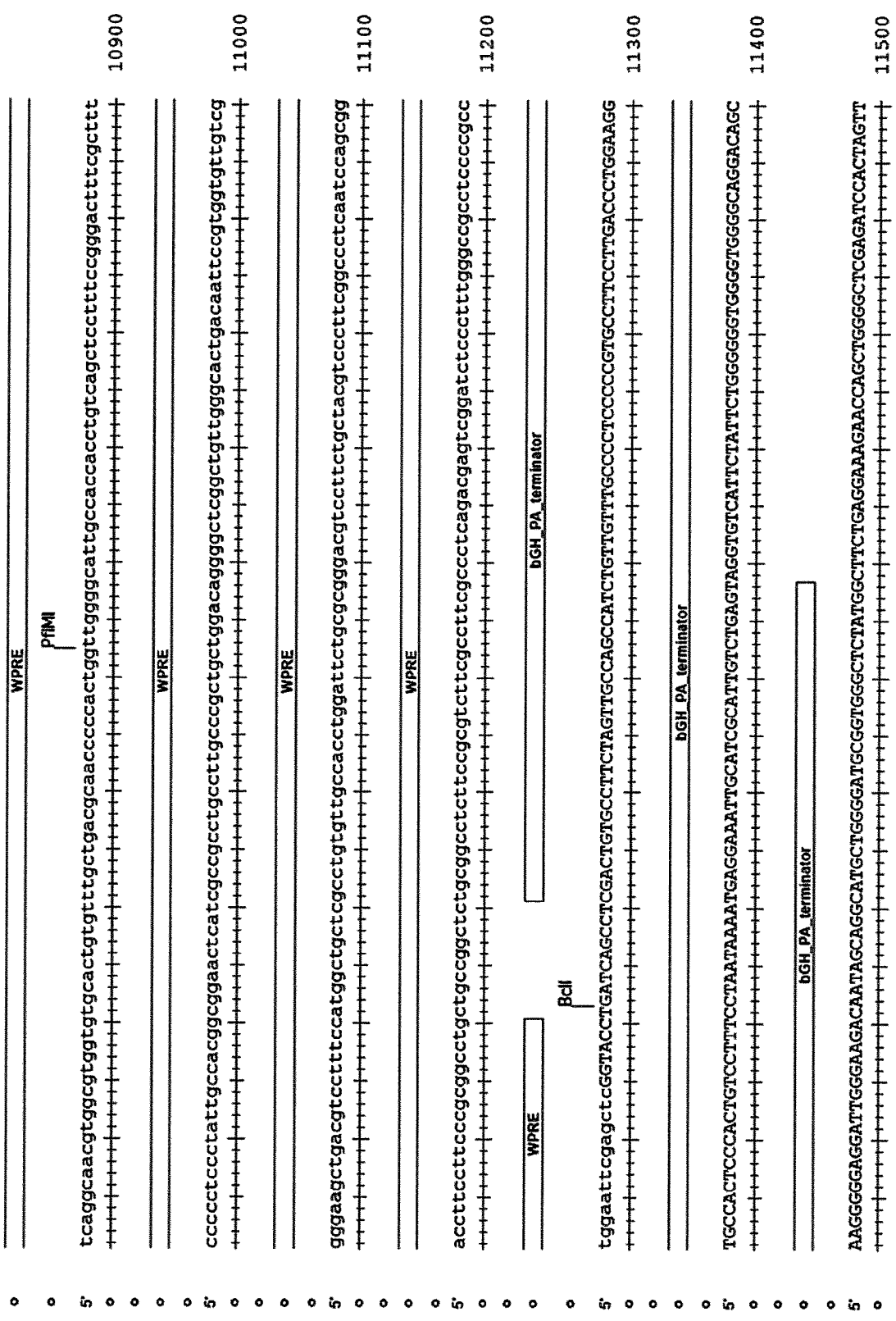

Figure 14, continued

```
                                    SV40 OriR + pA
           CTAGCCTCGAGGCGGCCGCCACCGCGtagtagttcatgtcatcttattcagtattcttatatcttataacttgcaaagaaatgaatcagagagtgag    11600

SV40 OriR + pA
           aggaacttgtgtttattgcagctataatgttacaaatagcataacaaatttcacaaataaagcattttttcactgcattctagttgtgtt    11700

SV40 OriR + pA
           tgtccaaactcatcatcaatgtatcttatcatgtctctggctctagctaactccgcccctaatcccgcccagtccgcccattctccgccccatggctgactaatt    11800

SV40 OriR + pA                              AvrII
           ttttttatttatgcagagaggccgaggccgcctcggcctctgagctattccagaagtagtgaggaggcttttttggAGGCCTaggctttttgcgtcgagacgt    11900

SV40 OriR + pA
           acccaattcgccctatagtgagtcgtattacgcgcgctcactggccgtcgttttacaacgtcgtgactgggaaaacctggcgttaccaacttaatcgc    12000

SV40 OriR + pA
           cttgcagcacatcccccctttcgccagctggcgtaatagcgaagaggcccgcaccgatcgcccttcccaacagttgcgcagcctgaatggcgaatggcgcg    12100

SV40 OriR + pA
           acgcgccctgtagcggcgcattaagcgcggcgggtgtggtggttacgcgcagcgtgaccgctacacttgccagcgccctagcgcccgctcctttcgctttt    12200

SV40 OriR + pA
           cttcccttcctttctcgccacgttcgccggctttccccgtcaagctctaaatcggggctccctttagggttccgatttagtgctttacggcacctcgac    12300
```

Figure 14, continued
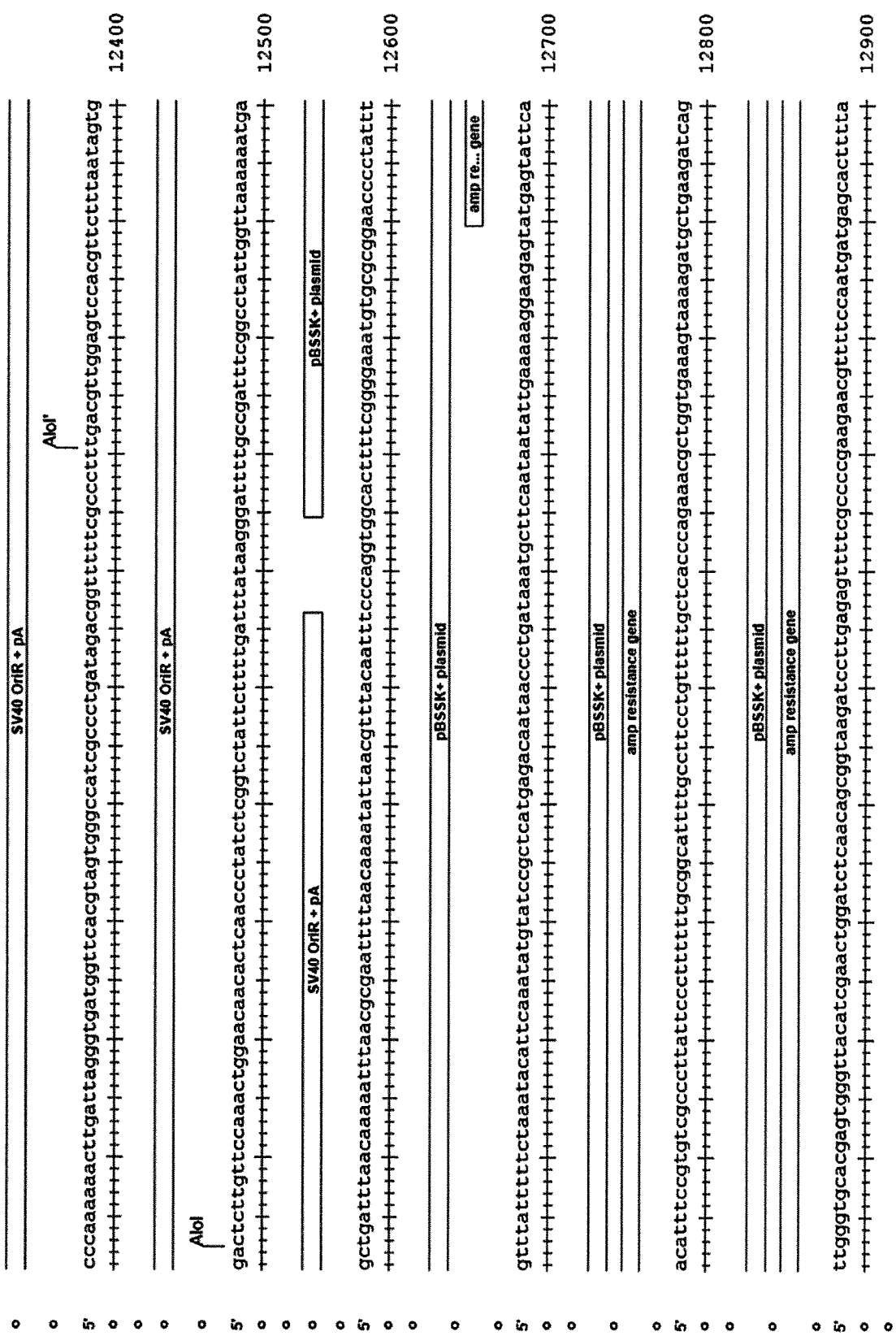

Figure 14, continued
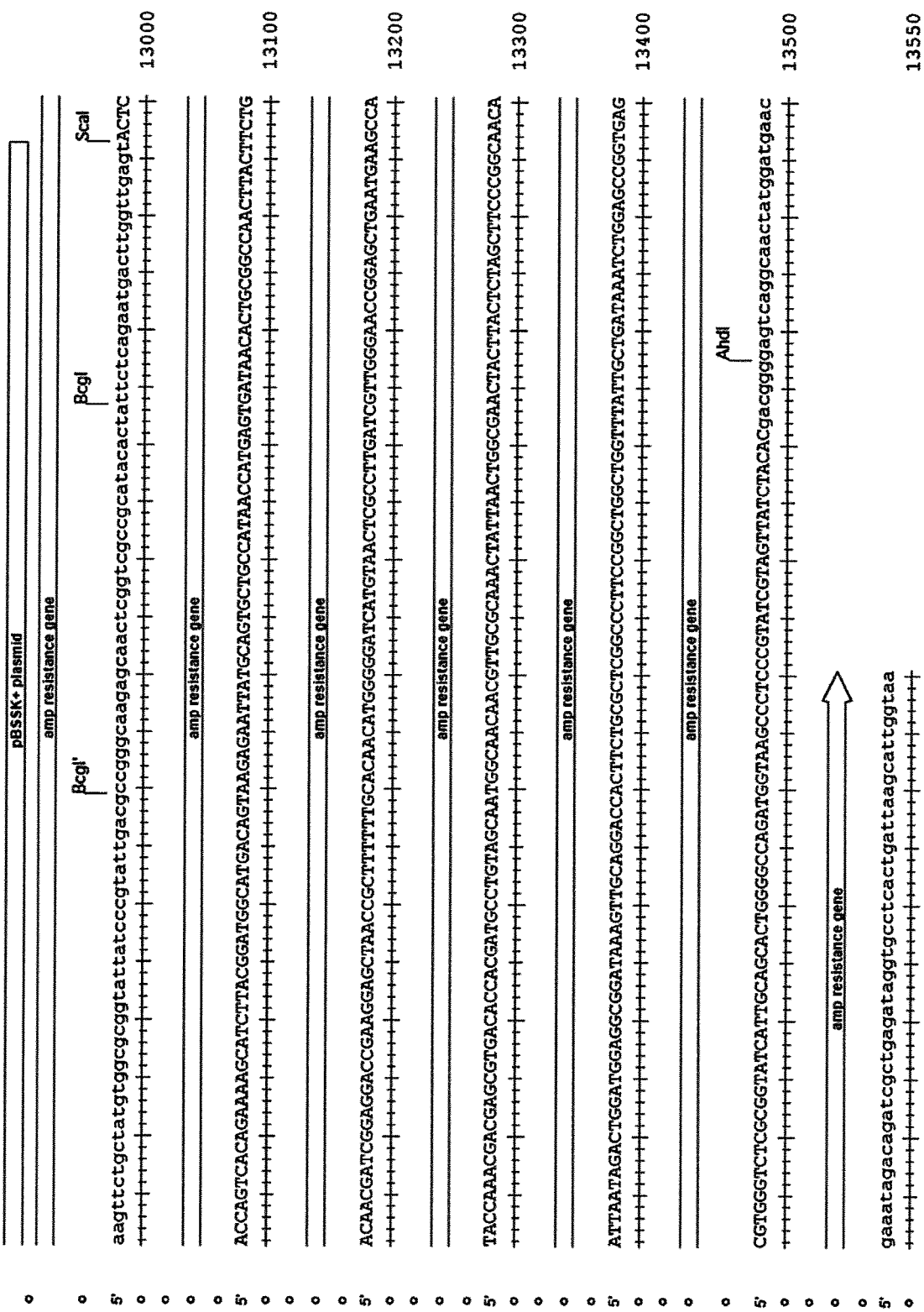

SEQUENCE LISTING

<160> NUMBER OF SEQ ID NOS: 29

<210> SEQ ID NO 1
<211> LENGTH: 2875
<212> TYPE: DNA
<213> ORGANISM: artificial sequence
<220> FEATURE:
<223> OTHER INFORMATION: ZF-Ldb1 vector as DNA equivalent of RNA lentivirus

<400> SEQUENCE: 1

| | | | | | | |
|---|---|---|---|---|---|---|
| cgcgttcgaa | ggggcaacca | ggggtccgcg | cgccgaggcc | tggggagcgg | ggcctcctgg | 60 |
| ggttggggga | ggaggtgctc | ttgtaatctg | cggtggtccc | caggcgggcg | ccacccctcc | 120 |
| gcccgcccgt | gccgggagcg | cccggcccga | cagcaagcgc | tctgggggcc | gataaggccc | 180 |
| tcgggggcct | ggcccgcacg | tcacaggccc | cgcagaggct | gcggtgagtc | cgccagcccc | 240 |
| agctgctcct | cctcaagccc | caaggcctt | tcggcggcaa | ttcccaccgg | tcgccaccat | 300 |
| ggcccaggcg | gccttggagc | ccggagagaa | accctacaaa | tgcccggagt | gtggaaagtc | 360 |
| cttcagcgac | tgtagggacc | tggcacgcca | ccagcgaacc | cacacaggcg | agaagcccta | 420 |
| taaatgtcca | gagtgtggaa | agagcttctc | tagaaacgat | gcactgactg | agcaccaacg | 480 |
| cacccatacc | ggggaaaaac | cttataaatg | tcctgagtgt | ggtaaaagtt | tttctcaatt | 540 |
| ggctcatctc | cgcgctcacc | aacgcacgca | tactggtgag | aagccctata | gtgccccga | 600 |
| atgcggcaag | agttttctc | aaagcgggga | ccttagaaga | caccaaagaa | cccataccgg | 660 |
| cgaaaaacct | tacaagtgtc | ccgagtgcgg | aaaatctttt | tcacgcaaag | acaatttgaa | 720 |
| gaaccaccag | cggacacaca | ccggtgaaaa | gccttacaaa | tgtcccgaat | gtggcaagtc | 780 |
| attctcagac | cccggagccc | tggtgcgcca | tcagcgcact | cacactggca | agaagactag | 840 |
| cggccaggcc | ggccaggcta | gcccgaaaaa | gaaacgcaaa | gttgggcgcg | ccctggatcg | 900 |
| ggatgtgggc | ccaactccca | tgtacccacc | tacatacctg | gagcctggga | tcgggaggca | 960 |
| cacaccatat | ggtaaccaaa | ccgactatag | aatatttgag | cttaacaaac | ggctacagaa | 1020 |
| ctggacagag | gagtgtgaca | atctctggtg | ggatgctttc | acaactgagt | tctttgaaga | 1080 |
| tgacgccatg | ctgaccatca | ctttctgctt | ggaggatgga | ccaaagagat | ataccattgg | 1140 |
| ccggaccctg | ataccacgct | acttccgaag | cattttttgag | gggggtgcca | cagagctgta | 1200 |
| ctacgtgctc | aagcacccca | aggaggcatt | ccacagcaac | ttcgtgtccc | tcgactgtga | 1260 |
| ccagggcagc | atggtgaccc | agcacggcaa | acccatgttt | acccaggtgt | gtgtggaagg | 1320 |
| ccggttgtac | ctggagttca | tgtttgacga | catgatgcgg | ataaagacgt | ggcacttcag | 1380 |
| catccggcaa | cacagagagc | tcatccccag | aagtatcctg | gccatgcacg | cccaggaccc | 1440 |
| ccagatgctg | gatcagctgt | ccaaaaacat | taccggtgt | gggctgtcct | taattaacta | 1500 |
| cccgtacgac | gttccggact | acgcttcttg | aatcggtagg | aattaattct | gcagcggccg | 1560 |
| cggatccgcc | cctctccctc | cccccccct | aacgttactg | gccgaagccg | cttggaataa | 1620 |
| ggccggtgtg | cgtttgtcta | tatgttattt | tccaccatat | tgccgtcttt | tggcaatgtg | 1680 |
| agggcccgga | aacctggccc | tgtcttcttg | acgagcattc | ctaggggtct | ttcccctctc | 1740 |
| gccaaaggaa | tgcaaggtct | gttgaatgtc | gtgaaggaag | cagttcctct | ggaagcttct | 1800 |
| tgaagacaaa | caacgtctgt | agcgaccctt | tgcaggcagc | ggaaccccc | acctggcgac | 1860 |
| aggtgcctct | gcggccaaaa | gccacgtgta | taagatacac | ctgcaaaggc | ggcacaaccc | 1920 |
| cagtgccacg | ttgtgagttg | gatagttgtg | gaaagagtca | aatggctctc | ctcaagcgta | 1980 |

```
ttcaacaagg ggctgaagga tgcccagaag gtaccccatt gtatgggatc tgatctgggg   2040
cctcggtgca catgctttac atgtgtttag tcgaggttaa aaaaacgtct aggcccccg    2100 aaccacgggg acgtggtttt cctttgaaaa acacgatgat aatatggcca caaccatggt   2160
gagcaagggc gaggagctgt tcaccggggt ggtgcccatc ctggtcgagc tggacggcga   2220
cgtaaacggc cacaagttca gcgtgtccgg cgagggcgag ggcgatgcca cctacggcaa   2280
gctgaccctg aagttcatct gcaccaccgg caagctgccc gtgccctggc ccaccctcgt   2340
gaccaccctg acctacggcg tgcagtgctt cagccgctac cccgaccaca tgaagcagca   2400
cgacttcttc aagtccgcca tgcccgaagg ctacgtccag gagcgcacca tcttcttcaa   2460
ggacgacggc aactacaaga cccgcgccga ggtgaagttc gagggcgaca ccctggtgaa   2520
ccgcatcgag ctgaagggca tcgacttcaa ggaggacggc aacatcctgg ggcacaagct   2580
ggagtacaac tacaacagcc acaacgtcta tatcatggcc gacaagcaga gaacggcat    2640 caaggtgaac ttcaagatcc gccacaacat cgaggacggc agcgtgcagc tcgccgacca   2700
ctaccagcag aacacccca tcggcgacgg ccccgtgctg ctgcccgaca ccactacct    2760 gagcacccag tccgccctga gcaaagaccc caacgagaag cgcgatcaca tggtcctgct   2820
ggagttcgtg accgccgccg ggatcactct cggcatggac gagctgtaca agtaa         2875
```

<210> SEQ ID NO 2
<211> LENGTH: 410
<212> TYPE: PRT
<213> ORGANISM: artificial sequence
<220> FEATURE:
<223> OTHER INFORMATION: ZF-LDB1 fusion

<400> SEQUENCE: 2

```
Met Ala Gln Ala Ala Leu Glu Pro Gly Glu Lys Pro Tyr Lys Cys Pro
 1               5                   10                  15

Glu Cys Gly Lys Ser Phe Ser Asp Cys Arg Asp Leu Ala Arg His Gln
                20                  25                  30

Arg Thr His Thr Gly Glu Lys Pro Tyr Lys Cys Pro Glu Cys Gly Lys
            35                  40                  45

Ser Phe Ser Arg Asn Asp Ala Leu Thr Glu His Gln Arg Thr His Thr
        50                  55                  60

Gly Glu Lys Pro Tyr Lys Cys Pro Glu Cys Gly Lys Ser Phe Ser Gln
 65                  70                  75                  80

Leu Ala His Leu Arg Ala His Gln Arg Thr His Thr Gly Glu Lys Pro
                 85                  90                  95

Tyr Lys Cys Pro Glu Cys Gly Lys Ser Phe Ser Gln Ser Gly Asp Leu
            100                 105                 110

Arg Arg His Gln Arg Thr His Thr Gly Glu Lys Pro Tyr Lys Cys Pro
        115                 120                 125

Glu Cys Gly Lys Ser Phe Ser Arg Lys Asp Asn Leu Lys Asn His Gln
    130                 135                 140

Arg Thr His Thr Gly Glu Lys Pro Tyr Lys Cys Pro Glu Cys Gly Lys
145                 150                 155                 160

Ser Phe Ser Asp Pro Gly Ala Leu Val Arg His Gln Arg Thr His Thr
                165                 170                 175

Gly Lys Lys Thr Ser Gly Gln Ala Gly Gln Ala Ser Pro Lys Lys Lys
            180                 185                 190

Arg Lys Val Gly Arg Ala Leu Asp Arg Asp Val Gly Pro Thr Pro Met
        195                 200                 205
```

Tyr Pro Thr Tyr Leu Glu Pro Gly Ile Gly Arg His Thr Pro Tyr
    210                 215                 220

Gly Asn Gln Thr Asp Tyr Arg Ile Phe Glu Leu Asn Lys Arg Leu Gln
225                 230                 235                 240

Asn Trp Thr Glu Glu Cys Asp Asn Leu Trp Trp Asp Ala Phe Thr Thr
                245                 250                 255

Glu Phe Phe Glu Asp Asp Ala Met Leu Thr Ile Thr Phe Cys Leu Glu
                260                 265                 270

Asp Gly Pro Lys Arg Tyr Thr Ile Gly Arg Thr Leu Ile Pro Arg Tyr
            275                 280                 285

Phe Arg Ser Ile Phe Glu Gly Gly Ala Thr Glu Leu Tyr Tyr Val Leu
290                 295                 300

Lys His Pro Lys Glu Ala Phe His Ser Asn Phe Val Ser Leu Asp Cys
305                 310                 315                 320

Asp Gln Gly Ser Met Val Thr Gln His Gly Lys Pro Met Phe Thr Gln
                325                 330                 335

Val Cys Val Glu Gly Arg Leu Tyr Leu Glu Phe Met Phe Asp Asp Met
            340                 345                 350

Met Arg Ile Lys Thr Trp His Phe Ser Ile Arg Gln His Arg Glu Leu
355                 360                 365

Ile Pro Arg Ser Ile Leu Ala Met His Ala Gln Asp Pro Gln Met Leu
            370                 375                 380

Asp Gln Leu Ser Lys Asn Ile Thr Arg Cys Gly Leu Ser Leu Ile Asn
385                 390                 395                 400

Tyr Pro Tyr Asp Val Pro Asp Tyr Ala Ser
                405                 410

<210> SEQ ID NO 3
<211> LENGTH: 13550
<212> TYPE: DNA
<213> ORGANISM: artificial sequence
<220> FEATURE:
<223> OTHER INFORMATION: ALS10 as DNA equilvalent of RNA lentiviral
      vector

<400> SEQUENCE: 3
ctgtcagacc aagtttactc atatatactt tagattgatt taaaacttca ttttaattt    60 aaaaggatct aggtgaagat cctttttgat aatctcatga ccaaaatccc ttaacgtgag   120
ttttcgttcc actgagcgtc agaccccgta gaaaagatca aaggatcttc ttgagatcct   180
ttttttctgc gcgtaatctg ctgcttgcaa acaaaaaaac caccgctacc agcggtggtt   240
tgtttgccgg atcaagagct accaactctt tttccgaagg taactggctt cagcagagcg   300
cagataccaa atactgtcct tctagtgtag ccgtagttag gccaccactt caagaactct   360
gtagcaccgc ctacataccc gctctgctaa tcctgttac cagtggctgc tgccagtggc   420
gataagtcgt gtcttaccgg gttggactca agacgatagt taccggataa ggcgcagcgg   480
tcgggctgaa cggggggttc gtgcacacag cccagcttgg agcgaacgac ctacaccgaa   540
ctgagatacc tacagcgtga gctatgagaa agcgccacgc ttcccgaagg gagaaaggcg   600
gacaggtatc cggtaagcgg cagggtcgga acaggagagc gcacgaggga gcttccaggg   660
ggaaacgcct ggtatcttta tagtcctgtc gggtttcgcc acctctgact tgagcgtcga   720 ttttgtgat gctcgtcagg gggcggagc ctatggaaaa acgccagcaa cgcggccttt   780
ttacggttcc tggccttttg ctggcctttt gctcacatgt tctttcctgc gttatcccct   840
gattctgtgg ataaccgtat taccgccttt gagtgagctg ataccgctcg ccgcagccga   900

```
acgaccgagc gcagcgagtc agtgagcgag gaagcggaag agcgcccaat acgcaaaccg    960
cctctccccg cgcgttggcc gattcattaa tgcagctggc acgacaggtt cccgactgg    1020 aaagcgggca gtgagcgcaa cgcaattaat gtgagttagc tcactcatta ggcaccccag   1080
gctttacact ttatgcttcc ggctcgtatg ttgtgtggaa ttgtgagcgg ataacaattt   1140
cacacaggaa acagctatga ccatgattac gccaagcgcg caattaaccc tcactaaagg   1200
gaacaaaagc tggagctgca agcttggcca ttgcatacgt tgtatccata tcataatatg   1260
tacatttata ttggctcatg tccaacatta ccgccatgtt gacattgatt attgactagt   1320
tattaatagt aatcaattac ggggtcatta gttcatagcc catatatgga gttccgcgtt   1380
acataactta cggtaaatgg cccgcctggc tgaccgccca acgacccccg cccattgacg   1440
tcaataatga cgtatgttcc catagtaacg ccaatagga cttccattg acgtcaatgg    1500 gtggagtatt tacggtaaac tgcccacttg gcagtacatc aagtgtatca tatgccaagt   1560 acgccccta ttgacgtcaa tgacggtaaa tggcccgcct ggcattatgc ccagtacatg    1620
accttatggg actttcctac ttggcagtac atctacgtat tagtcatcgc tattaccatg   1680
gtgatgcggt tttggcagta catcaatggg cgtggatagc ggtttgactc acggggattt   1740
ccaagtctcc accccattga cgtcaatggg agtttgtttt ggcaccaaaa tcaacgggac   1800
tttccaaaat gtcgtaacaa ctccgcccca ttgacgcaaa tgggcggtag gcgtgtacgg   1860
tgggaggtct atataagcag agctcgttta gtgaaccggg gtctctctgg ttagaccaga   1920
tctgagcctg ggagctctct ggctaactag ggaacccact gcttaagcct caataaagct   1980
tgccttgagt gcttcaagta gtgtgtgccc gtctgttgtg tgactctggt aactagagat   2040
ccctcagacc cttttagtca gtgtggaaaa tctctagcag tggcgcccga acagggacct   2100
gaaagcgaaa gggaaaccag agctctctcg acgcaggact cggcttgctg aagcgcgcac   2160
ggcaagaggc gaggggcggc gactggtgag tacgccaaaa attttgacta gcggaggcta   2220
gaaggagaga gatgggtgcg agagcgtcag tattaagcgg gggagaatta gatcgcgatg   2280
ggaaaaaatt cggttaaggc caggggggaaa gaaaaaatat aaattaaaac atatagtatg   2340
ggcaagcagg gagctagaac gattcgcagt taatcctggc ctgttagaaa catcagaagg   2400
ctgtagacaa atactgggac agctacaacc atcccttcag acaggatcag aagaacttag   2460
atcattatat aatacagtag caaccctcta ttgtgtgcat caaaggatag agataaaaga   2520
caccaaggaa gctttagaca agatagagga agagcaaaac aaaagtaaga ccaccgcaca   2580
gcaagcggcc gctgatcttc agacctggag gaggagatat gagggacaat ggagaagtg    2640 aattatataa atataaagta gtaaaaattg aaccattagg agtagcaccc accaaggcaa   2700
agagaagagt ggtgcagaga gaaaaaagag cagtgggaat aggagctttg ttccttgggt   2760
tcttgggagc agcaggaagc actatgggcg cagcctcaat gacgctgacg gtacaggcca   2820
gacaattatt gtctggtata gtgcagcagc agaacaattt gctgagggct attgaggcgc   2880
aacagcatct gttgcaactc acagtctggg gcatcaagca gctccaggca agaatcctgg   2940
ctgtggaaag atacctaaag gatcaacagc tcctggggat ttggggttgc tctggaaaac   3000
tcatttgcac cactgctgtg ccttggaatg ctagttggag taataaatct ctggaacaga   3060
tttggaatca cacgacctgg atggagtggg acagagaaat taacaattac acaagcttaa   3120
tacactcctt aattgaagaa tcgcaaaacc agcaagaaaa gaatgaacaa gaattattgg   3180
aattagataa atgggcaagt ttgtggaatt ggtttaacat aacaaattgg ctgtggtata   3240
```

```
taaaattatt cataatgata gtaggaggct tggtaggttt aagaatagtt tttgctgtac    3300
tttctatagt gaatagagtt aggcagggat attcaccatt atcgtttcag acccacctcc    3360
caaccccgag gggacccgac aggcccgaag gaatagaaga agaaggtgga gagagagaca    3420
gagacagatc cattcgatta gtgaacggat ctcgacggta tcggttaact tttaaaagaa    3480 aagggggat  tgggggggtac agtgcagggg aaagaatagt agacataata gcaacagaca    3540
tacaaactaa agaattacaa aaacaaatta caaaaattca aattttatc  gataagcttg    3600 ggagttccgc gtgttggggg tggaccatcc tctaggtatt gaataagaaa aatgaagtta    3660
aggtggttga tggtaacact atgctaataa ctgcagagcc agaagcacca taagggacat    3720
gataagggag ccagcagacc tctgatctct tcctgaatgc taatcttaaa catcctgagg    3780
aagaatggga cttccatttg gggtgggcct atgatagggt aataagacag tagtgaatat    3840
caagctacaa aaagcccct  ttcaaattct tctcagtcct aacttttcat actaagccca    3900
gtccttccaa agcagactgt gaaagagtga tagttccggg agactagcac tgcagattcc    3960
gggtcactgt gagtggggga ggcagggaag aagggctcac aggacagtca aaccatgccc    4020
cctgtttttc cttcttcaag tagacctcta taagacaaca gagacaacta aggctgagtg    4080
gccaggcgag gagaaaccat ctcgccgtaa acatggaag  gaacacttca ggggaaaggt    4140
ggtatctcta agcaagagaa ctgagtggag tcaaggctga gagatgcagg ataagcaaat    4200
gggtagtgaa aagacattca tgaggacagc taaaacaata agtaatgtaa aatacagcat    4260
agcaaaactt taacctccaa atcaagcctc tacttgaatc cttttctgag ggatgaataa    4320
ggcataggca tcaggggctg ttgccaatgt gcattagctg tttgcagcct caccttcttt    4380
catggagttt aagatatagt gtattttccc aaggtttgaa ctagctcttc atttctttat    4440
gttttaaatg cactgacctc ccacattccc ttttagtaa  aatattcaga ataatttaa    4500 atacatcatt gcaatgaaaa taatgttttt ttattaggca gaatccagat gctcaaggcc    4560
cttcataata tcccccagtt tagtagttgg acttagggaa caaggaacc  tttaatagaa    4620 attggacagc aagaaagcga gcttagtgat acttgtgggc cagggcatta gccacaccag    4680
ccaccacttt ctgataggca gcctgcactg gtggggtgaa ttcttttgcca aagtgatggg    4740 ccagcacaca gaccagcacg ttgcccagga gctgtgggag aagataaga  ggtatgaaca    4800 tgattagcaa aagggcctag cttggactca gaataatcca gccttatccc aaccataaaa    4860
taaaagcaga atggtagctg gattgtagct gctattagca atatgaaacc tcttacatca    4920
gttacaattt atatgcagaa atatttatat gcagaaatat tgctattgcc ttaacccaga    4980
aattatcact gttattcttt agaatggtgc aaagaggcat gatacattgt atcattattg    5040
ccctgaaaga aagagattag ggaaagtatt agaaataaga taaacaaaaa agtatattaa    5100
aagaagaaag catttttaa  aattacaaat gcaaaattac cctgatttgg tcaatatgtg    5160
tacacatatt aaaacattac actttaaccc ataaatatgt ataatgatta tgtatcaatt    5220
aaaaataaaa gaaaataaag tagggagatt atgaatatgc aaataagcac acatatattc    5280
caaatagtaa tgtactaggc agactgtgta aagttttttt ttaagttact taatgtatct    5340
cagagatatt tccttttgtt atacacaatg ttaaggcatt aagtataata gtaaaaattg    5400
cggagaagaa aaaaaagaa  agcaagaatt aaacaaaaga aaacaattgt tatgaacagc    5460
aaataaaaga aactaaaacg atcctgagac ttccacactg atgcaatcat tcgtctgttt    5520
cccattctaa actgtacccct gttacttctc cccttcctat gacatgaact taaccataga    5580
aaagaagggg aaagaaaaca tcaagggtcc catagactca ccctgaagtt ctcaggatcc    5640
```

```
acgtgcagct tgtcacagtg cagctcactc agtgtggcaa aggtgccctt gaggttgtcc    5700
aggtgagcca ggccatcact aaaggcaccg agcactttct tgccatgagc cttcaccttg    5760
gggttgccca taacagcatc aggagtggac agatccccaa aggactcaaa gaacctctgg    5820
gtccaagggt agaccaccag cagcctaagg gtgggaaaat agaccaatag gcagagagag    5880
tcagtgccta tcagaaaccc aagagtcttc tctgtctcca catgcccagt ttctattggt    5940
ctccttaaac ctgtcttgta accttgatac caacctgccc agggcctcac caccaacttc    6000
atccacgttc accttgcccc acagggcagt aacggcagac ttctcctcag gagtcaggtg    6060
caccatggtg tctgtttgag gttgctagtg aacacagttg tgtcagaagc aaatgtaagc    6120
aatagatggc tctgccctga cttttatgcc cagccctggc tcctgccctc cctgctcctg    6180
ggagtagatt ggccaaccct agggtgtggc tccacagggt gaggtctaag tgatgacagc    6240
cgtacctgtc cttggctctt ctggcactgg cttaggagtt ggacttcaaa ccctcagccc    6300
tccctctaag atatatctct tggccccata ccatcagtac aaattgctac taaaaacatc    6360
ctcctttgca agtgtattta cgtaatattt ggaatcacag cttggtaagc atattgaaga    6420 tcgtttttccc aattttctta ttacacaaat aagaaattga tgcactaaaa gtggaagagt    6480
tttgtctacc ataattcagc tttgggatat gtagatggat ctcttcctgc gtctccagaa    6540
tatgcaaaat acttacagga cagaatggat gaaaactcta cctcagttct aagcatatct    6600
tctccttatt tggattaaaa ccttctggta agaaaagaaa aaaatatat atatatatgt    6660 gtatatatac acacatacat atacatatat atgcattcat ttgttgttgt ttttcttaat    6720
ttgctcatgg tatatgtgta tatatatata tatatattca ggaaataata tattctagaa    6780
tatgtcacat tctgtctcag gcatccattt tctttatgat gccgtttgag gtggagtttt    6840
agtcaggtgg tcagcttctc cttttttttg ccatctgccc tgtaagcatc ctgctgggga    6900
cccagatagg agtcatcact ctaggctgag aacatctggg cacacaccct aagcctcagc    6960
atgactcatc atgactcagc attgctgtgc ttgagccaga aggtttgctt agaaggttac    7020
acagaaccag aaggcggggg tggggcactg accccgacag gggcctggcc agaactgctc    7080
atgcttggac tatgggaggt cactaatgga gacacacaga aatgtaacag gaactaagga    7140
aaaactgaag cttatttaat cagagatgag atgctggaag ggatagaggg agctgagctt    7200
gtaaaaagta tagtaatcat tcagcaaatg gttttgaagc acctgctgga tgctaaaacac    7260 tattttcagt gcttgaatca taaataagaa taaaacatgt atcttattcc ccacaagagt    7320
ccaagtaaaa aataacagtt aattataatg tgctctgtcc cccaggctgg agtgcagtgg    7380
cacgatctca gctcactgca acctccgcct cccgggttca gcaattctc ctgcctcagc    7440 caccctaata gctgggatta caggtgcaca ccaccatgcc aggctaattt ttgtactttt    7500
tgtagaggca gggtatcacc atgttgtcca agatggtctt gaactcctga gctccaagca    7560
gtccacccac ctcagcctcc caaagtgcta tctgcggccg cctatctgta ccactagtct    7620
cgagaagctt tcattaaaaa aagtctaacc agctgcattc gactttgact gcagcagctg    7680
gttagaaggt tctactggag gagggtccca gcccattgct aaattaacat caggctctga    7740
gactggcagt atatctctaa cagtggttga tgctatcttc tggaacttgc ctgctacatt    7800
gagaccactg acccatacat aggaagccca tagctctgtc ctgaactgtt aggccactgg    7860
tccagagagt gtgcatctcc tttgatcctc ataataaccc tatgagatag acacaattat    7920
tactcttact ttatagatga tgatcctgaa aacataggag tcaaggcact tgcccctagc    7980
```

```
tgggggtata ggggagcagt cccatgtagt agtagaatga aaaatgctgc tatgctgtgc   8040
ctcccccacc tttcccatgt ctgccctcta ctcatggtct atctctcctg gctcctggga   8100
gtcatggact ccacccagca ccaccaacct gacctaacca cctatctgag cctgccagcc   8160
tataacccat ctgggccctg atagctggtg gccagccctg accccacccc accctccctg   8220
gaacctctga tagacacatc tggcacacca gctcgcaaag tcaccgtgag ggtcttgtgt   8280
ttgctgagtc aaaattcctt gaaatccaag tccttagaga ctcctgctcc caaatttaca   8340
gtcatagact tcttcatggc tgtctccttt atccacagaa tgattccttt gcttcattgc   8400
cccatccatc tgatcctcct catcagtgca gcacagggcc catgagcagt agctgcagag   8460
tctcacatag gtctggcact gcctctgaca tgtccgacct taggcaaatg cttgactctt   8520
ctgagctcag tcttgtcatg gcaaaataaa gataataata gtgttttttt atggagttag   8580
cgtgaggatg gaaaacaata gcaaaattga ttagactata aaaggtctca acaaatagta   8640
gtagatttta tcatccatta atccttccct ctcctctctt actcatccca tcacgtatgc   8700
ctcttaattt tcccttacct ataataagag ttattcctct tattatattc ttcttatagt   8760
gattctggat attaaagtgg gaatgagggg caggccacta acgaagaaga tgtttctcaa   8820
agaagccatt ctccccacat agatcatctc agcagggttc aggaagataa aggaggatca   8880
aggtcgaagg taggaactaa ggaagaacac tgggcaagtg gatcctgagc ccctttttcct  8940
ctaactgaaa gaaggaaaaa aaaatggaaa cccaaaatat tctacatagt ttccatgtca   9000
cagccagggc tgggcagtct cctgttattt cttttaaaat aaatatatca tttaaatgca   9060
taaataagca aaccctgctc gggaatggga gggagagtct ctggagtcca ccccttctcg   9120
gccctggctc tgcagatagt gctatcaaag ccctgacaga gccctgccca ttgctgggcc   9180
ttggagtgag tcagcctagt agagaggcag ggcaagccat ctcatagctg ctgagtggga   9240
gagagaaaag ggctcattgt ctataaactc aggtcatggc tattcttatt ctcacactaa   9300
gaaaaagaat gagatgtcta catatacccct gcgtcccctc ttgtgtactg gggcccccaa   9360
gagctctcta aaagtgatgg caaagtcatt gcgctagatg ccatcccatc tattataaac   9420
ctgcatttgt ctccacacac cagtcatgga caataaccct cctcccaggt ccacgtgctt   9480
gtctttgtat aatactcaag taatttcgga aaatgtattc tttcaatctt gttctgttat   9540
tcctgtttca atggcttagt agaaaaagta catacttgtt ttcccataaa ttgacaatag   9600
acaatttcac atcaatgtct atatgggtcg ttgtgtttgc tgtgtttgca aaaactcaca   9660
ataactttat attgttacta ctctaagaaa gttacaacat ggtgaataca agagaaagct   9720
attacaagtc cagaaaataa aagttatcat cttgaggcct cagctttcta ggaataatat   9780
caatattaca aaattaatct aacaattatg aacagcaatg agataaatatg tacaaagtac   9840
ccagacctat gtggtagagc atcaaggaag cgcattgcgg agcagttttt tgtttgtttg   9900
ttttgtatt ctgtttcgtg aggcaaggtt tcactctgct gtccaggctg gagtgcagtg    9960
gcaagatcat gtctcactgc agccttgaca ctacacgtgc tttaagacca atgacttaca   10020
aggcagctgt agatcttagc cactttttaa aagaaaaggg gggactggaa gggctaattc   10080
actcccaacg aagacaagat ctgcttttg ctagcgcggc cgctctagac tagtggggcc    10140
cgtgcaattg aagccggctg gcgccaagct tctctgcagg atgtgcgggc caggcccccg    10200
agggccttat cggccccaga ggcgcttgct gtcgggccgg gcgctccgg cacgggcggg     10260
cggaggggtg gcgcccgcct ggggaccgca gattacaaga gcacctcctc ccccaacccc    10320
aggaggcccc gctcccagg cctcggccgg cgcggacccc tggttgcccc ggatgtacag    10380
```

```
gcatgcgtcg acctcgaggg ggggcccggt accgctagca ctgggtctct ctggttagac   10440
cagatctgag cctgggagct ctctggctaa ctagggaacc cactgcttaa gcctcaataa   10500
agcttgcctt gagtgcttca agtagtgtgt gcccgtctgt tgtgtgactc tggtaactag   10560
agatccctca gacccttta gtcagtgtgg aaaatctcta gcaggtcgac aatcaacctc    10620
tggattacaa aatttgtgaa agattgactg gtattcttaa ctatgttgct ccttttacgc   10680
tatgtggata cgctgcttta atgcctttgt atcatgctat tgcttcccgt atggctttca   10740
ttttctcctc cttgtataaa tcctggttgc tgtctcttta tgaggagttg tggcccgttg   10800
tcaggcaacg tggcgtggtg tgcactgtgt ttgctgacgc aaccccact ggttggggca    10860 ttgccaccac ctgtcagctc ctttccggga cttcgctttt ccccctccct attgccacgg   10920
cggaactcat cgccgcctgc cttgcccgct gctggacagg ggctcggctg ttgggcactg   10980
acaattccgt ggtgttgtcg gggaagctga cgtccttcc atggctgctc gcctgtgttg    11040
ccacctggat tctgcgcggg acgtccttct gctacgtccc ttcggccctc aatccagcgg   11100
accttccttc ccgcggcctg ctgccggctc tgcggcctct tccgcgtctt cgccttcgcc   11160
ctcagacgag tcggatctcc cttttgggccg cctcccccgcc tggaattcga gctcggtacc   11220
tgatcagcct cgactgtgcc ttctagttgc cagccatctg ttgtttgccc ctcccccgtg   11280
ccttccttga ccctggaagg tgccactccc actgtccttt cctaataaaa tgaggaaatt   11340
gcatcgcatt gtctgagtag gtgtcattct attctggggg gtggggtggg gcaggacagc   11400 aaggggagg attgggaaga caatagcagg catgctgggg atgcggtggg ctctatggct    11460
tctgaggaaa gaaccagctg gggctcgaga tccactagtt ctagcctcga ggctagagcg   11520
gccgccaccg cggtagtagt tcatgtcatc ttattattca gtatttataa cttgcaaaga   11580
aatgaatatc agagagtgag aggaacttgt ttattgcagc ttataatggt tacaaataaa   11640
gcaatagcat cacaaatttc acaaataaag catttttttc actgcattct agttgtggtt   11700
tgtccaaact catcaatgta tcttatcatg tctggctcta gctatcccgc ccctaactcc   11760
gcccagttcc gcccattctc cgccccatgg ctgactaatt ttttttattt atgcagaggc   11820
cgaggccgcc tcggcctctg agctattcca gaagtagtga ggaggctttt ttggaggcct   11880
aggcttttgc gtcgagacgt acccaattcg ccctatagtg agtcgtatta cgcgcgctca   11940
ctggccgtcg ttttacaacg tcgtgactgg gaaaaccctg gcgttaccca acttaatcgc   12000
cttgcagcac atccccctt cgccagctgg cgtaatagcg aagaggcccg caccgatcgc    12060
ccttcccaac agttgcgcag cctgaatggc gaatggcgcg acgcgccctg tagcggcgca   12120
ttaagcgcgg cgggtgtggt ggttacgcgc agcgtgaccg ctacacttgc cagcgcccta   12180
gcgcccgctc ctttcgcttt cttcccttcc tttctcgcca cgttcgccgg ctttccccgt   12240
caagctctaa atcgggggct cccttagggg ttccgattta gtgctttacg gcacctcgac   12300
cccaaaaaac ttgattaggg tgatggttca cgtagtgggc catcgccctg atagacggtt   12360
tttcgccctt tgacgttgga gtccacgttc tttaatagtg gactcttgtt ccaaactgga   12420
acaacactca accctatctc ggtctattct tttgatttat aagggatttt gccgatttcg   12480
gcctattggt taaaaaatga gctgatttaa caaaaattta acgcgaattt taacaaaata   12540
ttaacgttta caatttccca ggtggcactt ttcggggaaa tgtgcgcgga acccctattt   12600
gtttattttt ctaaatacat tcaaatatgt atccgctcat gagacaataa ccctgataaa   12660
tgcttcaata atattgaaaa aggaagagta tgagtattca acatttccgt gtcgccctta   12720
```

-continued

```
ttccctttt  tgcggcattt  tgccttcctg  tttttgctca  cccagaaacg  ctggtgaaag    12780
taaaagatgc  tgaagatcag  ttgggtgcac  gagtgggtta  catcgaactg  gatctcaaca    12840
gcggtaagat  ccttgagagt  tttcgccccg  aagaacgttt  tccaatgatg  agcacttta    12900 aagttctgct  atgtggcgcg  gtattatccc  gtattgacgc  cgggcaagag  caactcggtc    12960
gccgcataca  ctattctcag  aatgacttgg  ttgagtactc  accagtcaca  gaaaagcatc    13020
ttacggatgg  catgacagta  agagaattat  gcagtgctgc  cataaccatg  agtgataaca    13080
ctgcggccaa  cttacttctg  acaacgatcg  gaggaccgaa  ggagctaacc  gcttttttgc    13140
acaacatggg  ggatcatgta  actcgccttg  atcgttggga  accggagctg  aatgaagcca    13200
taccaaacga  cgagcgtgac  accacgatgc  ctgtagcaat  ggcaacaacg  ttgcgcaaac    13260
tattaactgg  cgaactactt  actctagctt  cccgcaaca  attaatagac  tggatggagg    13320
cggataaagt  tgcaggacca  cttctgcgct  cggcccttcc  ggctggctgg  tttattgctg    13380
ataaatctgg  agccggtgag  cgtgggtctc  gcggtatcat  tgcagcactg  gggccagatg    13440
gtaagccctc  ccgtatcgta  gttatctaca  cgacggggag  tcaggcaact  atggatgaac    13500
gaaatagaca  gatcgctgag  ataggtgcct  cactgattaa  gcattggtaa              13550
```

<210> SEQ ID NO 4
<211> LENGTH: 754
<212> TYPE: DNA
<213> ORGANISM: human

<400> SEQUENCE: 4

```
cggctgtcat  cacttagacc  tcaccctgtg  gagccacacc  ctagggttgg  ccaatctact      60
cccaggagca  gggagggcag  gagccagggc  tgggcataaa  agtcagggca  gagccatcta     120
ttgcttacat  ttgcttctga  cacaactgtg  ttcactagca  acctcaaaca  gacaccatgg     180
tgcacctgac  tcctgaggag  aagtctgccg  ttactgccct  gtggggcaag  gtgaacgtgg     240
atgaagttgg  tggtgaggcc  ctgggcaggc  tgctggtggt  ctaccccttgg  acccagaggt     300 tctttgagtc  ctttggggat  ctgtccactc  ctgatgctgt  tatgggcaac  cctaaggtga     360
aggctcatgg  caagaaagtg  ctcggtgcct  ttagtgatgg  cctggctcac  ctggacaacc     420
tcaagggcac  ctttgccaca  ctgagtgagc  tgcactgtga  caagctgcac  gtggatcctg     480
agaacttcag  gctcctgggc  aacgtgctgg  tctgtgtgct  ggcccatcac  tttggcaaag     540
aattcacccc  accagtgcag  gctgcctatc  agaaagtggt  ggctggtgtg  gctaatgccc     600
tggcccacaa  gtatcactaa  gctcgctttc  ttgctgtcca  atttctatta  aaggttcctt     660
tgttccctaa  gtccaactac  taaactgggg  gatattatga  agggccttga  gcatctggat     720
tctgcctaat  aaaaaacatt  tattttcatt  gcaa                                  754
```

<210> SEQ ID NO 5
<211> LENGTH: 147
<212> TYPE: PRT
<213> ORGANISM: human

<400> SEQUENCE: 5

```
Met Val His Leu Thr Pro Glu Glu Lys Ser Ala Val Thr Ala Leu Trp
1               5                   10                  15

Gly Lys Val Asn Val Asp Glu Val Gly Gly Glu Ala Leu Gly Arg Leu
            20                  25                  30

Leu Val Val Tyr Pro Trp Thr Gln Arg Phe Phe Glu Ser Phe Gly Asp
        35                  40                  45
```

```
Leu Ser Thr Pro Asp Ala Val Met Gly Asn Pro Lys Val Lys Ala His
    50                  55                  60
Gly Lys Lys Val Leu Gly Ala Phe Ser Asp Gly Leu Ala His Leu Asp
 65                  70                  75                  80
Asn Leu Lys Gly Thr Phe Ala Thr Leu Ser Glu Leu His Cys Asp Lys
                 85                  90                  95
Leu His Val Asp Pro Glu Asn Phe Arg Leu Leu Gly Asn Val Leu Val
            100                 105                 110
Cys Val Leu Ala His His Phe Gly Lys Glu Phe Thr Pro Pro Val Gln
        115                 120                 125
Ala Ala Tyr Gln Lys Val Val Ala Gly Val Ala Asn Ala Leu Ala His
    130                 135                 140
Lys Tyr His
145

<210> SEQ ID NO 6
<211> LENGTH: 20
<212> TYPE: DNA
<213> ORGANISM: artificial sequence
<220> FEATURE:
<223> OTHER INFORMATION: Primer

<400> SEQUENCE: 6
caagaaagtg ctcggtgcct                                          20

<210> SEQ ID NO 7
<211> LENGTH: 19
<212> TYPE: DNA
<213> ORGANISM: artificial sequence
<220> FEATURE:
<223> OTHER INFORMATION: Primer

<400> SEQUENCE: 7
gcaaaggtgc ccttgaggt                                           19

<210> SEQ ID NO 8
<211> LENGTH: 25
<212> TYPE: DNA
<213> ORGANISM: artificial sequence
<220> FEATURE:
<223> OTHER INFORMATION: Primer

<400> SEQUENCE: 8
tagtgatggc ctggctcacc tggac                                    25

<210> SEQ ID NO 9
<211> LENGTH: 20
<212> TYPE: DNA
<213> ORGANISM: artificial sequence
<220> FEATURE:
<223> OTHER INFORMATION: Primer

<400> SEQUENCE: 9
tccccaccac caagacctac                                          20

<210> SEQ ID NO 10
<211> LENGTH: 19
<212> TYPE: DNA
<213> ORGANISM: artificial sequence
<220> FEATURE:
<223> OTHER INFORMATION: Primer

<400> SEQUENCE: 10
```
ccttaacctg ggcagagcc                                              19

<210> SEQ ID NO 11
<211> LENGTH: 22
<212> TYPE: DNA
<213> ORGANISM: artificial sequence
<220> FEATURE:
<223> OTHER INFORMATION: Primer

<400> SEQUENCE: 11
tcccgcactt cgacctgagc ca                                          22

<210> SEQ ID NO 12
<211> LENGTH: 21
<212> TYPE: DNA
<213> ORGANISM: artificial sequence
<220> FEATURE:
<223> OTHER INFORMATION: Primer

<400> SEQUENCE: 12
tggcaagaag gtgctgactt c                                           21

<210> SEQ ID NO 13
<211> LENGTH: 19
<212> TYPE: DNA
<213> ORGANISM: artificial sequence
<220> FEATURE:
<223> OTHER INFORMATION: Primer

<400> SEQUENCE: 13
tcactcagct gggcaaagg                                              19

<210> SEQ ID NO 14
<211> LENGTH: 24
<212> TYPE: DNA
<213> ORGANISM: artificial sequence
<220> FEATURE:
<223> OTHER INFORMATION: Primer

<400> SEQUENCE: 14
tgggagatgc cataaagcac ctgg                                        24

<210> SEQ ID NO 15
<211> LENGTH: 24
<212> TYPE: DNA
<213> ORGANISM: artificial sequence
<220> FEATURE:
<223> OTHER INFORMATION: Primer

<400> SEQUENCE: 15
tgatgtgtgt ccattggtgt gagc                                        24

<210> SEQ ID NO 16
<211> LENGTH: 24
<212> TYPE: DNA
<213> ORGANISM: artificial sequence
<220> FEATURE:
<223> OTHER INFORMATION: Primer

<400> SEQUENCE: 16
tgcgaacttg aacgtcagga gtct                                        24

<210> SEQ ID NO 17
<211> LENGTH: 24
<212> TYPE: DNA
<213> ORGANISM: artificial sequence

```
<220> FEATURE:
<223> OTHER INFORMATION: Primer

<400> SEQUENCE: 17
agctgctttc ggctttctcc ctta                                              24

<210> SEQ ID NO 18
<211> LENGTH: 24
<212> TYPE: DNA
<213> ORGANISM: artificial sequence
<220> FEATURE:
<223> OTHER INFORMATION: Primer

<400> SEQUENCE: 18
cctttgcatt tgcagcagtt cagc                                              24

<210> SEQ ID NO 19
<211> LENGTH: 24
<212> TYPE: DNA
<213> ORGANISM: artificial sequence
<220> FEATURE:
<223> OTHER INFORMATION: Primer

<400> SEQUENCE: 19
tcaaccgatc atccctcaca ctct                                              24

<210> SEQ ID NO 20
<211> LENGTH: 24
<212> TYPE: DNA
<213> ORGANISM: artificial sequence
<220> FEATURE:
<223> OTHER INFORMATION: Primer

<400> SEQUENCE: 20
aatcagcagc gcttccattc aagg                                              24

<210> SEQ ID NO 21
<211> LENGTH: 18
<212> TYPE: DNA
<213> ORGANISM: artificial sequence
<220> FEATURE:
<223> OTHER INFORMATION: Primer

<400> SEQUENCE: 21
gctgcctcca cccaagtg                                                     18

<210> SEQ ID NO 22
<211> LENGTH: 21
<212> TYPE: DNA
<213> ORGANISM: artificial sequence
<220> FEATURE:
<223> OTHER INFORMATION: Primer

<400> SEQUENCE: 22
accaactctg ggcagtcaca t                                                 21

<210> SEQ ID NO 23
<211> LENGTH: 20
<212> TYPE: DNA
<213> ORGANISM: artificial sequence
<220> FEATURE:
<223> OTHER INFORMATION: Primer

<400> SEQUENCE: 23
agcaaccacc catgcctgcc                                                   20
```

```
<210> SEQ ID NO 24
<211> LENGTH: 20
<212> TYPE: DNA
<213> ORGANISM: artificial sequence
<220> FEATURE:
<223> OTHER INFORMATION: Primer

<400> SEQUENCE: 24
ctcgggccaa aggcctcacg                                                   20

<210> SEQ ID NO 25
<211> LENGTH: 17
<212> TYPE: DNA
<213> ORGANISM: artificial sequence
<220> FEATURE:
<223> OTHER INFORMATION: Primer

<400> SEQUENCE: 25
cggctgttgg gcactga                                                      17

<210> SEQ ID NO 26
<211> LENGTH: 19
<212> TYPE: DNA
<213> ORGANISM: artificial sequence
<220> FEATURE:
<223> OTHER INFORMATION: Primer

<400> SEQUENCE: 26
ggaaggtccg ctggattga                                                    19

<210> SEQ ID NO 27
<211> LENGTH: 22
<212> TYPE: DNA
<213> ORGANISM: artificial sequence
<220> FEATURE:
<223> OTHER INFORMATION: Primer

<400> SEQUENCE: 27
atggctgctc gcctgtgttg cc                                                22

<210> SEQ ID NO 28
<211> LENGTH: 22
<212> TYPE: DNA
<213> ORGANISM: artificial sequence
<220> FEATURE:
<223> OTHER INFORMATION: Primer

<400> SEQUENCE: 28
aaggtgagca aggtggagat tc                                                22

<210> SEQ ID NO 29
<211> LENGTH: 21
<212> TYPE: DNA
<213> ORGANISM: artificial sequence
<220> FEATURE:
<223> OTHER INFORMATION: Primer

<400> SEQUENCE: 29
ttccgagttc agctccaact g                                                 21
```

VIRAL VECTORS FOR PROPHYLAXIS AND THERAPY OF HEMOGLOBINOPATHIES

CROSS REFERENCE TO RELATED APPLICATIONS

This application claims priority to U.S. Provisional application No. 62/105,829, filed on Jan. 21, 2015, the disclosure of which is incorporated herein by reference.

STATEMENT REGARDING FEDERALLY SPONSORED RESEARCH

This invention was made with government support under contract no. 1R01HL102449 awarded by the National Institutes of Health. The government has certain rights in the invention.

FIELD

The present disclosure related to compositions and methods useful for prophylaxis and/or therapy of hemoglobinopathies.

BACKGROUND

There are a variety of hemoglobinopathies that affect large portions of the human population. For example, sickle-cell anemia (SCA) is a blood related disorder that affects the structure of the hemoglobin molecules. In SCA the hemoglobin molecule is defective, causing the entire blood cell to change shape (Steinberg, M. H., Forget, B. G., Higgs, D. R. & Nagel, R. L. Disorders of hemoglobin: Genetics, Pathophysiology and Clinical Management, (Cambridge University Press, Cambridge, UK, 2001)). After these abnormal hemoglobin molecules release oxygen in circulation, they may cluster together and form long, rod-like structures, which become rigid and assume sickle shape. Unlike healthy red blood cells, which are usually smooth and donut-shaped, sickled red blood cells cannot squeeze through small blood vessels. Instead, they stack up and cause blockages that deprive organs and tissues of oxygen-carrying blood. This produces periodic episodes of pain and ultimately can damage tissues and vital organs and lead to other serious medical problems. Normal red blood cells live about 120 days in the bloodstream, but sickled red cells die after about 10 to 20 days. Because they cannot be replaced fast enough, the blood is chronically short of red blood cells, leading to anemia.

SCA affects millions throughout the world. It is particularly common among people whose ancestors come from Sub-Saharan Africa, South America, Cuba, Central America, Saudi Arabia, India, and Mediterranean countries such as Turkey, Greece, and Italy. In the Unites States, it affects around 72,000 people, most of whose ancestors come from Africa. The disease occurs in about 1 in every 500 African-American births and 1 in every 1000 to 1400 Hispanic-American births. About 2 million Americans, or 1 in 12 African Americans, carry the sickle cell allele.

Beta-thalassemia is one of the two the most common congenital anemias and is due to partial or complete lack of synthesis of beta-globin chains and hemoglobin. Patients affected by beta-thalassemia have mutations in the beta-globin gene. The World Health Organization (WHO) estimates that 50,000 to 100,000 children are born with symptomatic features of beta-thalassemia every year. Cooley's anemia, also known as beta-thalassemia major, the most severe form of this disease, is characterized by ineffective erythropoiesis (IE) and extra medullary hematopoiesis (EMH) requiring regular blood transfusions to sustain life.

In beta-thalassemia intermedia, where a greater number of beta-globin chains are synthesized, the clinical picture is milder and patients do not require frequent transfusions (Musallam, K. M., et al. Non-transfusion-dependent thalassemias. Haematologica 98, 833-844 (2013); Rivella, S. The role of ineffective erythropoiesis in non-transfusion-dependent thalassemia. Blood reviews 26 Suppl 1, S12-15 (2012); Ginzburg, Y. & Rivella, S. beta-thalassemia: a model for elucidating the dynamic regulation of ineffective erythropoiesis and iron metabolism. Blood 118, 4321-4330 (2011)). However, hemoglobin levels often decrease over time, splenomegaly appears, and patients suffer from progressive iron overload due to increased gastrointestinal iron absorption. Current disease management includes prenatal diagnosis, transfusion therapy, iron chelation and allogeneic bone marrow transplantation (BMT), which is limited by finding a compatible bone marrow donor and presents many risks and complications. Beta-thalassemia or Cooley's anemia has a serious impact on the life of those afflicted, as well as on society in general. Therefore, potential gene therapy approaches that provide therapy to these patients would be highly relevant. In this regard, mutations leading to Cooley's anemia can be classified as beta0, such as beta0-39, in which a single point mutation creates a stop codon and no beta-globin protein is produced, or beta+, such as beta+-IVS1-110, where a mutation in the first intron results in alternative splicing and insufficient beta-globin chain synthesis (Musallam, K. M., et al. Non-transfusion-dependent thalassemias. Haematologica 98, 833-844 (2013); Rivella, S. The role of ineffective erythropoiesis in non-transfusion-dependent thalassemia. Blood reviews 26 Suppl 1, S12-15 (2012); Ginzburg, Y. & Rivella, S. beta-thalassemia: a model for elucidating the dynamic regulation of ineffective erythropoiesis and iron metabolism. Blood 118, 4321-4330 (2011)). Previous research has shown that it is possible to rescue beta-thalassemia in mouse models by lentiviral-mediated beta-globin gene transfer (May, C., et al. Successful treatment of murine beta-thalassemia intermedia by transfer of the human beta-globin gene. *Blood* 99, 1902-1908. (2002); May, C., et al. Therapeutic hemoglobin synthesis in beta-thalassaemic mice expressing lentivirus-encoded human beta-globin. *Nature* 406, 82-86 (2000); Rivella, S., et al. A novel murine model of Cooley anemia and its rescue by lentiviral-mediated human beta-globin gene transfer. *Blood* 101, 2932-2939 (2003)). However, these animals are characterized by a complete deletion of the mouse beta-globin gene. Additional hemoglobinopathies are characterized by mutations in the beta-globin gene that lead to additional aberrant beta-globin chains and patho-physiological sequelae similar to sickle cell anemia and/or beta-thalassemia. Thus, there is an ongoing and unmet need for improved compositions and methods for treating hemoglobinopathies. The present disclosure is pertinent to this need.

SUMMARY

The present disclosure provides compositions and methods for prophylaxis and/or therapy of hemoglobinopathies. In general, hemoglobinopathies comprise disorders that are characterized by reduced synthesis or abnormal structure of the hemoglobin molecule. Thalassemias are considered a type of hemoglobinopathy, with the understanding that certain forms of hemoglobinopathies are typically inherited single-gene disorders that result in abnormal structure of one of the globin chains of the hemoglobin molecule, whereas thalassemias are considered other forms of hemoglobinopathies associated with underproduction of normal globin proteins, such as those cases that arise due to mutations in regulatory genes. Thus, the disclosure is pertinent to individuals in need of treatment for disorders that include but are not necessarily limited to those characterized by altered hemoglobin structure, such as in hemoglobin C disease, hemoglobin S-C disease, sickle cell anemia, as well as in various types of thalassemia that are well known in the art, including but not necessarily limited to beta-thalassemia. This is also pertinent to patients that have mixed hemoglobinopathy features, such as hemoglobin S/thalassemia, for instance.

In one aspect the disclosure provides a method for inducing expression of human beta-globin in erythrocytes for use in prophylaxis and/or therapy of a hemoglobinopathy in an individual. The method generally comprises introducing into erythrocyte progenitor cells, typically CD34+ cells, a polynucleotide encoding: i) a 5' long terminal repeat (LTR) and a self-inactivating 3' LTR (self-inactivating meaning the 3' LTR comprises a deletion relative to its native sequence, and thus results is replication incompetent); ii) at least one polyadenylation signal; iii) at least one promoter; iv) a globin gene locus control region (LCR); v) an ankyrin insulator element (Ank); vi) a Woodchuck Post-Regulatory Element (WPRE) configured such that the WPRE does not integrate into a target genome; and vii) a sequence that is a reverse complement to a sequence encoding modified human beta-globin comprising a βT87Q mutation (B-globinM). The sequence of human B-globinM is included with this disclosure. The B-globinM is expressed from integrated DNA that is derived from the viral genome. Thus, the B-globinM sequence in the RNA genome of the modified lentiviral vectors of this disclosure is configured so that the B-globinM is expressed in the context of the double stranded DNA that is from integration of the modified lentiviral genome. The expression can in certain embodiments be exclusive to certain cell types, such as erythrocytes. It will be recognized in certain instances that DNA sequences are provided, but those skilled in the art can readily envision the RNA equivalent of the DNA sequence, such as when a DNA sequence is used to illustrate features of a lentiviral genome.

The sequence encoding the B-globinM comprises a first intron (intron 1) between exon 1 and exon 2, and a second intron (intron 2) between exon 2 and exon 3. In certain embodiments intron 2 comprises more than 476 nucleotides of the human B-globinM intron 2 sequence, and may comprise up to the full intron 2 sequence. After introducing the lentiviral construct into erythrocyte progenitor cells the lentiviral construct integrates into one or more chromosomes in the progenitor cells, and the progenitor cells differentiate into erythrocytes. The erythrocytes derived from the erythrocyte progenitor cells produce the beta-globin protein.

The disclosure provides for modified erythrocytes that produce more human beta-globin than a suitable control. In one embodiment the control comprises a human beta-globin value obtained from control cells. In one non-limiting approach the control cells comprise erythrocytes from an individual who has the hemoglobinopathy, wherein the erythrocytes are progeny of progenitor cells into which a control viral vector was introduced. The control viral vector can comprise, for example, the 5' LTR, the 3' LTR, the at least one polyadenylation signal, the at least one promoter, the LCR, the Ank, a WPRE, and the sequence encoding the B-globinM, but the sequence encoding the B-globinM in the control viral vector comprises 476 or fewer nucleotides of the human B-globinM intron 2 sequence, and thus comprises an intron 2 that contains a deletion. In one embodiment, the modified erythrocytes produce increased adult hemoglobin, fetal hemoglobin, B-globinM, or a combination thereof, relative to a control.

In one embodiment the lentiviral vectors can further comprise a sequence encoding a fusion of an Ldb1 transcription factor and a zinc finger (ZF) domain. In certain embodiments the lentiviral vector can comprise a sequence encoding an RNA polynucleotide that is at has reverse complementarity to mRNA encoding transferrin receptor 1. The RNA polynucleotide is capable of decreasing transferrin receptor 1 mRNA by, for example, an RNAi-mediated process.

In certain approaches the disclosure includes modifying erythrocyte progenitor cells that are CD34+ cells. The CD34+ cells can be separated from the individual before the lentiviral vector is introduced into them. The CD34+ cells can be introduced into the individual subsequent to the introduction of the lentiviral vector. The lentiviral vector can be introduced using any suitable approach. In one embodiment the erythrocyte progenitor cells are infected with viral particles comprising a lentiviral vector, such as a recombinant+strand viral polynucleotide. In certain embodiments, approximately 50 infection particles (IP) per cell are used. In certain embodiments the cells into which the vector is introduced can be enriched for a certain cell type, such as CD34+ cells. In certain approaches the cells are held for a period of from 2-3 days after infection prior to introducing into an individual in need thereof. In embodiments the cells can be frozen and introduced into the patients after they are thawed. The lentiviral vectors can be introduced into a patient using any suitable method. In one approach they are administered by intravenous infusion, which may be performed subsequent to any other technique, such as after depletion of bone marrow cells, i.e., myeloablation. Those skilled in the art will recognize that a cells characterized by a suitable vector copy number (VCN) can be used. In one embodiment the VCN is approximately 1 VCN per cell.

The disclosure includes the lentiviral vectors themselves, the components of which are as described above for use in a method of the disclosure. Lentiviral vectors comprise modified, recombinant polynucleotides, and can comprise RNA or DNA polynucleotides. In certain embodiments a lentiviral vector of this disclosure comprises an isolated polynucleotide, or an isolated preparation of virions that comprise the lentiviral vector. In an embodiment a recombinant lentiviral vector of the disclosure is present in CD34+ cells, wherein the CD34+ cells have been separated from an individual.

Also provided is a method of making a viral particle preparation for use in prophylaxis and/or therapy for one or more hemoglobinopathies. This approach comprises introducing a plasmid encoding a lentiviral vector as described above into packaging cells, wherein the packaging cells comprise a DNA packaging plasmid which encodes at least one virion protein, and wherein the packaging cells comprises a DNA envelope plasmid which encodes an envelope protein. The packaging and envelope plasmids express their respective proteins, which facilitate formation of virions which comprise an RNA lentiviral vector of this disclosure.

DESCRIPTION OF THE FIGURES

FIG. 13 provides an annotated polynucleotide and encoded protein sequence of the ZF-Ldb1 vector and the DNA equivalent of the RNA. The nucleotide sequence in FIG. 13 is SEQ ID NO:1. The ZF-LDB1 AA sequence (shown as GG1=ZF and DDi=LDB1, with the HA terminal amino acid sequence) is SEQ ID NO:2. Vector features labeled in boxes are shown above the pertinent sequences.

DETAILED DESCRIPTION

Figure 1:
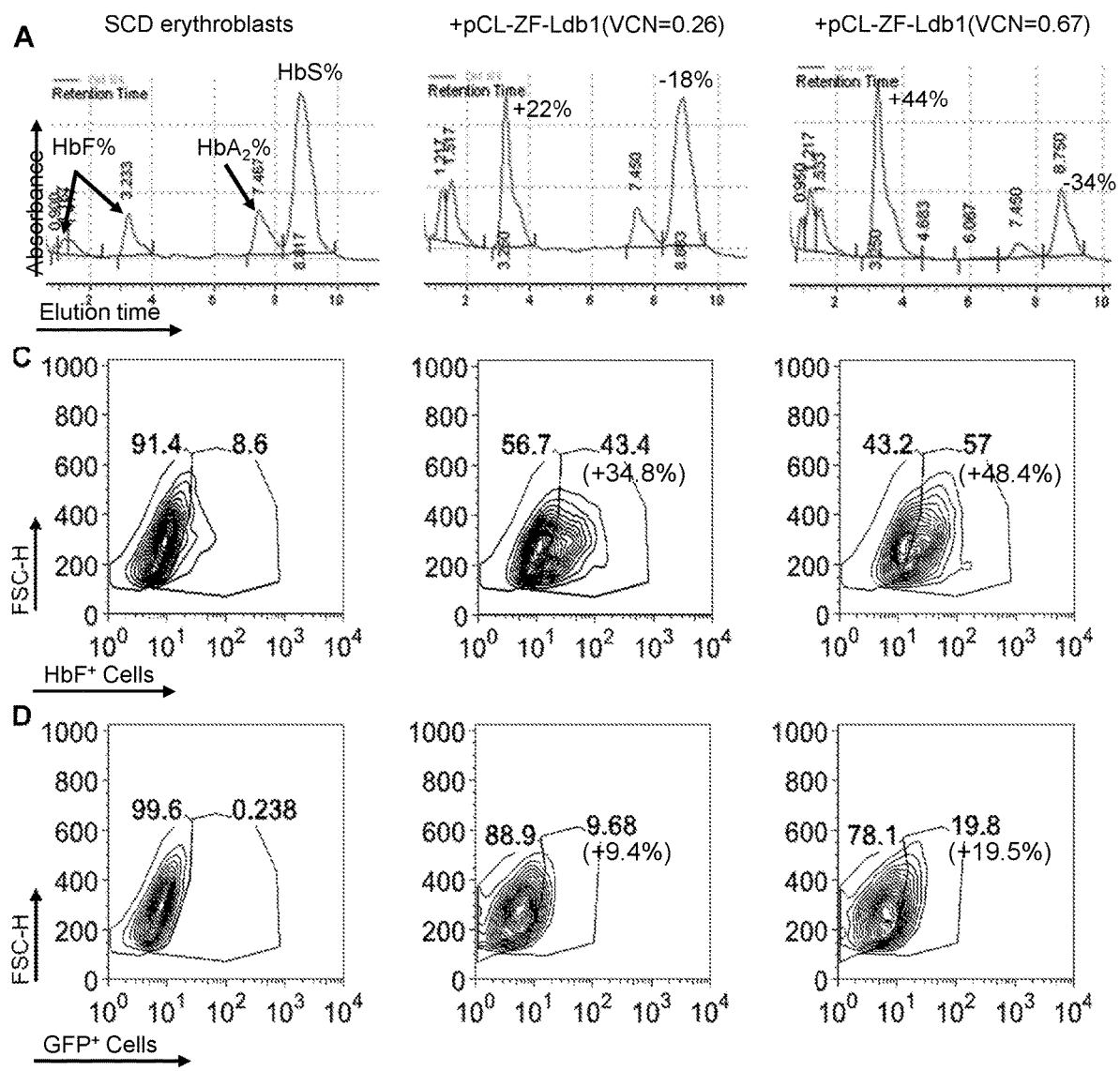
FIG. 1. The level of HbF/GFP expressing cells increases proportionally to the amount of molecules of GG1-SA vector integrated. (A) Lentiviral construct carrying the bicistronic cassette that expresses the Ldb1 SA domain under the ankyrin promoter (Ank Pr.) and the green fluorescence protein (GFP) through an internal ribosomal entry site (IRES). The Woodchuck hepatitis virus Posttrascriptional Regulatory Element (WPRE) increases RNA stability and protein yield. (B) Percentage of F, S and A2 hemoglobins measured by HPLC in differentiated untreated erythroid cells (left) or with up to 0.7 copies of ZF-Ldb1-viral molecules integrated on average (middle and right). (C) Increase in HbF and (D) GFP expressing cells measured by flow cytometry in cells untreated or with 0.26 and 0.67 copies/cell of ZF-Ldb1-viral molecules integrated.

The present disclosure provides compositions and methods for prophylaxis and/or therapy for hemoglobinopathies. In this regard, and as is well known in the art, a few months after birth children start producing red cells containing adult hemoglobin, which is the oxygen carrier molecule made of alpha- and beta-globin chains, encoded, respectively, by the alpha- and beta-globin genes. In many hemoglobinopathies, mutations in the gene encoding the beta-globin chain impair the synthesis of adult hemoglobin or lead to the production of abnormal adult hemoglobin. This leads to limited production of red cells or synthesis of abnormal red cells. For these reasons, patients require blood transfusion for survival. Before birth and during the first months of life, children express fetal hemoglobin, which comprises gamma- and alpha-chains. Generally, after birth the gene encoding the gamma-chain is silenced, while the beta-globin gene is activated, switching the production of hemoglobin from fetal to adult. In rare cases, individuals that do not silence the gamma-globin gene and also carry mutations in the beta-globin gene are spared from the disease associated with reduced or abnormal production of adult hemoglobin. Therefore, reactivation of fetal hemoglobin might be therapeutic in ameliorating diseases associated with mutations in the beta-globin gene. Activation and silencing of the gamma-globin gene depends on the proximity of a genomic region called locus control region (LCR), which maps ~40 to 60 kilobases upstream of the gamma- and beta-globin genes and is associated with many factors that activate transcription. This region is required to "loop" and bind the promoter of the gene that needs to be activated. When the gamma-globin gene is expressed, the LCR loops and binds on the gamma-globin promoter. After birth, the LCR moves away from the gamma-globin promoter and loops and binds the beta-globin promoter leading to silencing of the gamma gene and activation of the globin-gene. The transcription co-factor Ldb1 is involved in the LCR looping to the promoters of the gamma- and beta-globin genes. Ldb1 alone does not promote the binding of the LCR to the promoter, but requires additional factors. Artificial zinc-finger (ZF) proteins have the ability of binding specific sequences on the DNA. Ldb1 has been fused to a specific ZF protein that binds the gamma-globin promoter. In transgenic mice, this protein promotes the looping and binding of the LCR to the promoter of the gamma globin gene, activating its expression (Deng, W., et al. Controlling long-range genomic interactions at a native locus by targeted tethering of a looping factor. Cell 149, 1233-1244 (2012)).

An alternative way to approach therapy of hemoglobinopathies associated with mutation in the beta-globin gene is by inserting in the bone marrow cells (and in particular in the hematopoietic stem cells or HSCs) a functional beta-globin gene. Therefore, gene transfer of the non-mutated form of the beta-globin gene by lentiviral vectors could potentially restore production of the human beta-globin protein in patients and be utilized for gene therapy trials. Lentiviral vectors are well characterized for their ability to infect and insert the human beta-globin gene into HSCs. In this regard, the present disclosure provides novel viral vectors that are designed for prophylaxis and/or therapy of hemoglobinopathies. The viral vectors include but are not necessarily limited to lentiviral vectors. In various embodiments an isolated mammalian hematopoietic progenitor cell or an isolated mammalian stem cell comprising a recombinant lentiviral vector is provided.

Figure 11:
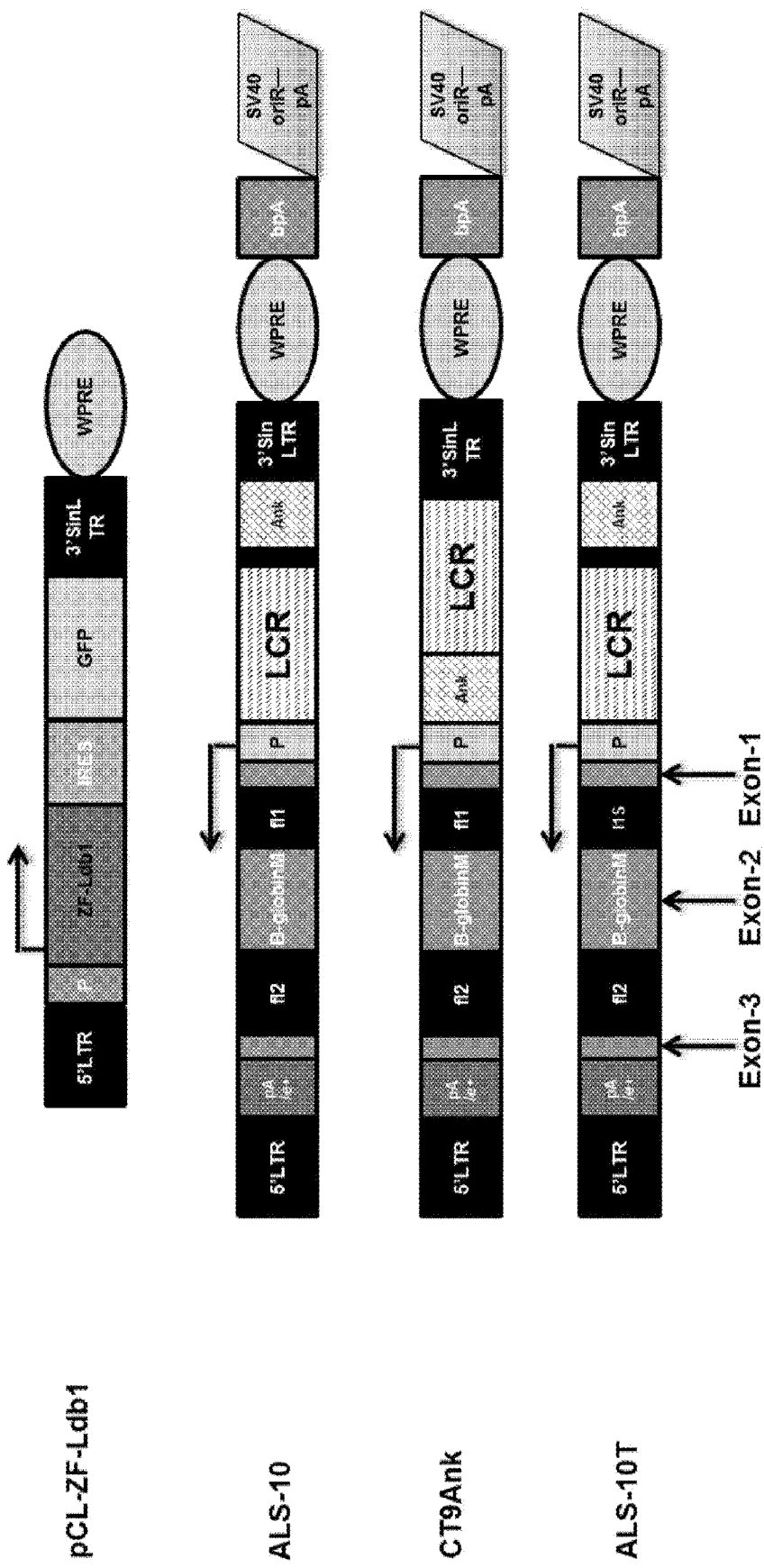
FIG. 11. Graphical maps of vectors. Topmost vector map is pCL-ZF-Ldb1, also referred to as pCL20cAnkyrinGG1DDiGFP. Second from vector map is ALS-10. Third from top vector map is CT9Ank. Bottom vector map is ALS-10T. Each vector comprises a 5' and a 3' self-inactivating long terminal repeat (5'LTR and 3'SinLTR, respectively). Also shown is "B-globinM" which is a mutant beta-globin is known as the "βT87Q" form. The B-globinM is configured in the vector such that it is expressed from an integrated DNA that is derived from the RNA genome via a well-known process. "Ank" is an Ankyrin insulator. "IRES" is an internal ribosomal entry site. "P" designates a promoter. "LCR" is a Locus control region. "GFP" is enhanced green fluorescence protein. "pA" is a polyadenylation signal. "WPRE" is the Woodchuck Post-Regulatory Element. "fI1" is a full beta-globin gene intron 1. "fI2" is a full beta-globin gene intron 2. "I1S" is a modified beta-globin gene intron 1 comprising a microRNA targeting the transferrin receptor. "SV40 oriR-pA" is an origin of replication and polyadenylation signal. Beta-globin gene exons 1, 2 and 3 are labeled accordingly.
Figure 14:
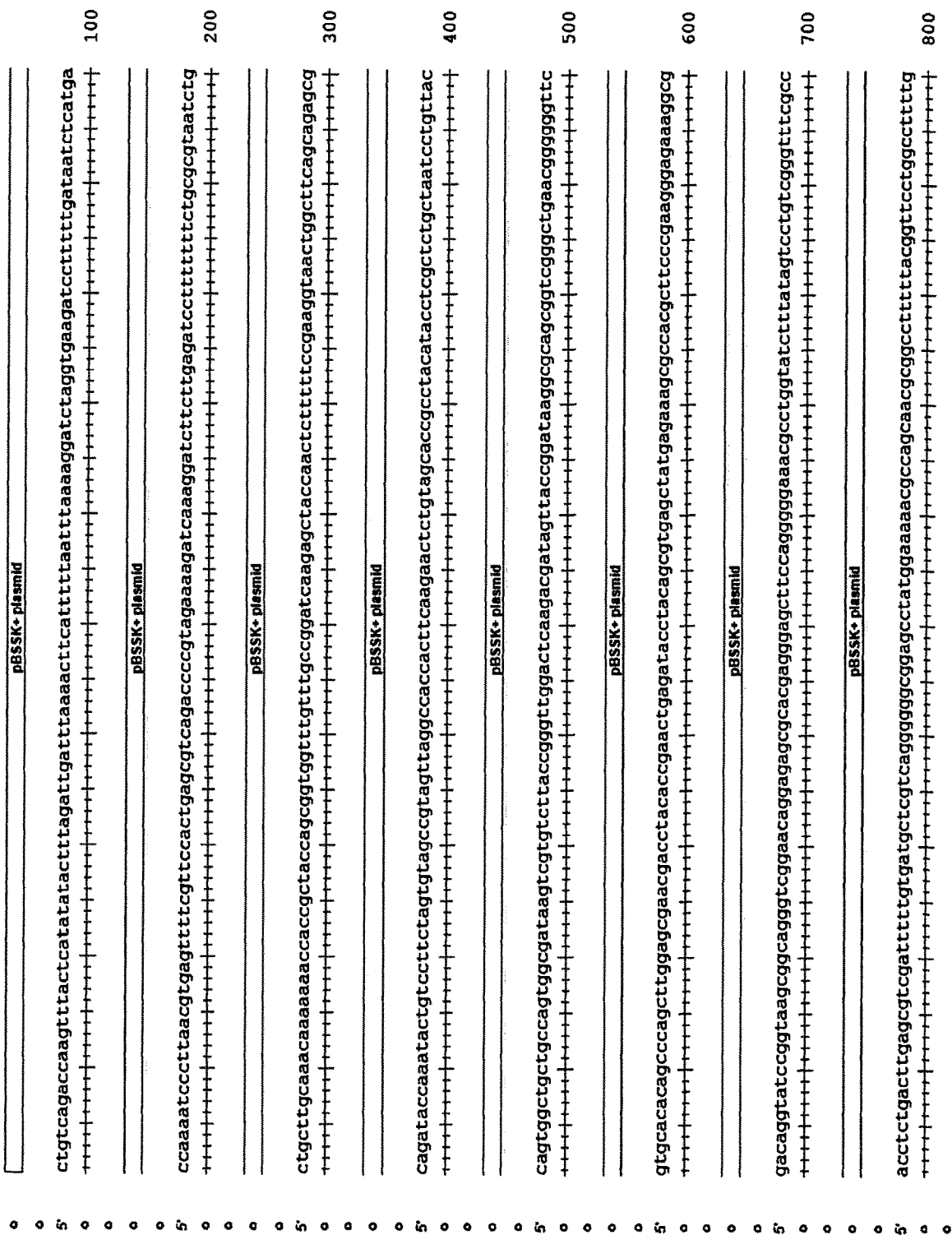
FIG. 14 provides an annotated polynucleotide sequence of the ALS-10 vector as the DNA equivalent of the RNA and encoded protein sequence. The nucleotide sequence shown in FIG. 14 is provided as SEQ ID NO:3. Vector features in boxes are shown above the pertinent sequences. The location of the initiating βT87Q beta globin methionine codon in its antiparallel configuration is the "CAT" triplet to the immediate left of the beta globin 5' UTR, reading in the 5' to 3' direction.
Figure 15:
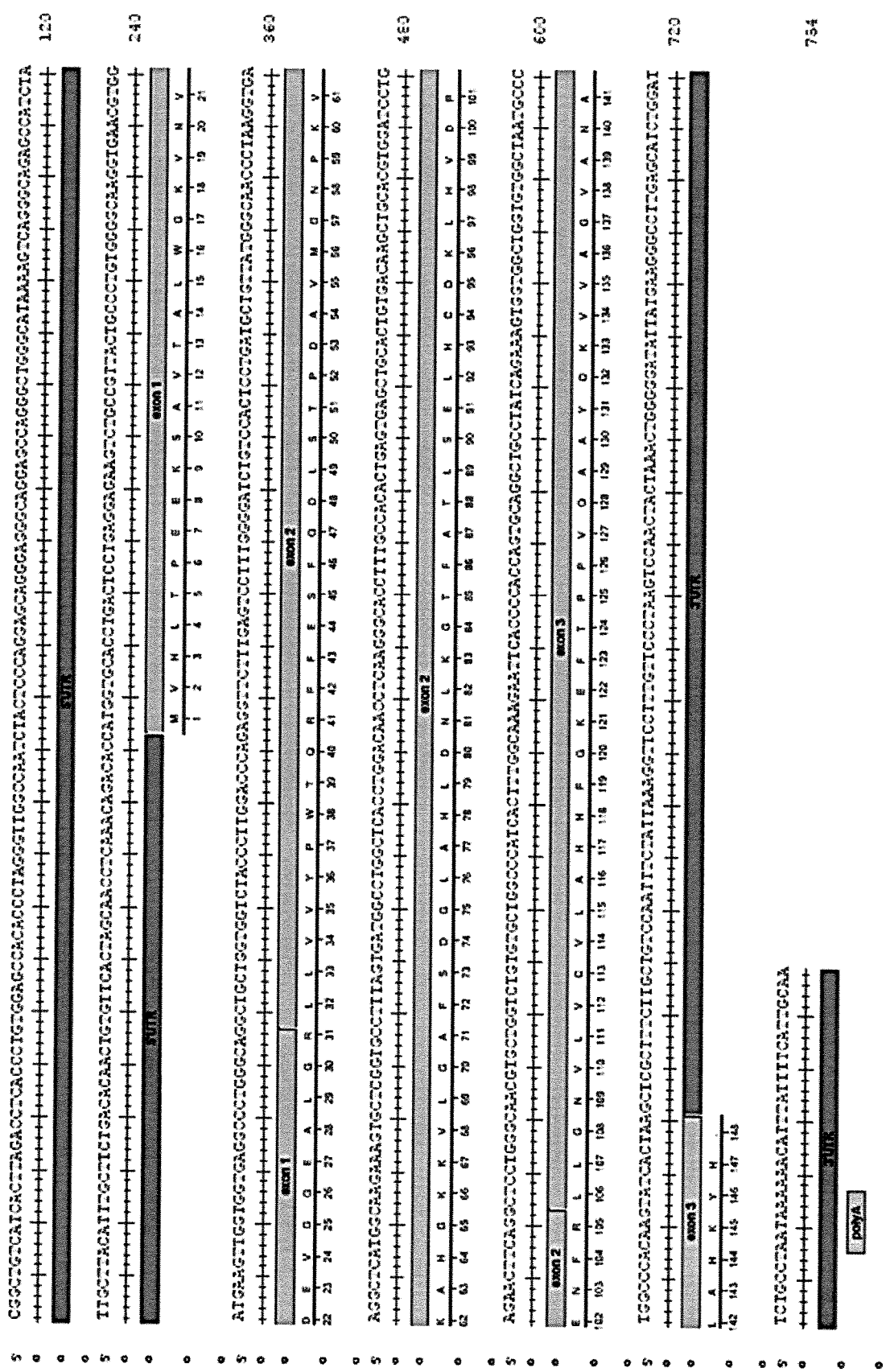
FIG. 15 provides an annotated sequence of the non-mutated beta-globin cDNA. The cDNA sequence is SEQ ID NO:4. Also shown is the beta-globin amino acid sequence which is provided in SEQ ID NO:5. The βT87Q mutation occurs at the Threonine which is shown in the sequence at position 88. The mutation is referred to as βT87Q according to convention wherein the first Methionine at position 1 is not included in the amino acid numbering. In the βT87Q mRNA, the codon for the Threonine at position 88 is replaced by a codon encoding Glutamine.

Various embodiments of lentiviral vectors that are subjects of this disclosure are shown in FIG. 11. Features of these vectors include but are not necessarily limited to the capability to, when introduced to an appropriate cell: 1) reactivate expression of fetal hemoglobin, and/or 2) express a novel transgene adult hemoglobin and/or, concurrently, 3) inactivate the expression of mutant hemoglobin. Certain features of the vectors are known in the art, and FIGS. 13 and 14 provide representative sequences of them. In particular, any suitable IRES sequence can be used, and those skilled in the art will recognize, given the benefit of this disclosure, which promoter sequences can be adapted for use in embodiments of the invention. Likewise, the LCR sequence is known in the art, as are suitable polyadenylation signals that can function, for example, in erythrocytes. The representative sequences of this disclosure, such as those shown in FIGS. 13 and 14, can be altered according to well-known parameters, so long as they impart to erythrocytes the ability to produced therapeutically effective amounts of elevated globin. In certain cases polynucleotide sequences can be identical to those presented herein, or they can have least 80, 81, 82, 83, 84, 85, 86, 87, 88, 89, 90, 91, 92, 93, 94, 95, 96, 97, 98, or 99% identity across a contiguous segment of the sequences.

It is expected that lentiviral vectors of this disclosure will result in the expression of therapeutic levels of hemoglobins where previous vectors have failed to do so. In embodiments, these vectors can be specifically adapted to optimize production of beta-globin plus gamma-globin mRNA, and protein levels in presence of different mutations associated with beta-thalassemia, sickle cell anemia and other hemoglobinopathies. Certain aspects of this disclosure involve combinations of genomic elements, specific embodiments of which are depicted schematically in FIG. 11. The disclosure includes each and every polynucleotide sequence disclosed herein, the RNA equivalent of every DNA polynucleotide (i.e., where uracil replaces thymine) and every DNA equivalent of every RNA, and the complementary sequence and the reverse complement of every polynucleotide sequence. The disclosure includes every amino acid sequence, and all polynucleotide sequences encoding the amino acid sequences. Contiguous segments of polynucleotides and polypeptides sequences are also included. In non-limiting examples, sequences of this disclosure can comprise or consist of any one or any combination of the contiguous segments of each vector construct disclosed herein, including but not limited to the segments and sequences depicted in FIGS. 11, 13, 14 and 15, the RNA equivalents thereof, and the DNA and RNA reverse complements thereof. In aspects of the disclosure integration of a lentiviral vector of the disclosure results in an integrated functional globin gene, the expression of which produces a globin molecule that is effective to a participate in providing a therapeutic benefit to an individual with a globinopathy. The gene may exhibit conditional expression, such as being expressed in erythrocytes, but not being expressed in for example, hematopoietic stem cells comprising an integrated DNA segment derived from the lentiviral construct, wherein the stem cells differentiate into the erythrocytes that express the globin molecule. The disclosure also includes cells, which comprise the recombinant polynucleotides.

The present disclosure includes a demonstration of using the ALS10 lentiviral vector depicted in FIG. 11 to elevate HbA production in cells from hemoglobinopathy patients. In particular, the disclosure includes a demonstration that the ALS10 vector is superior to previously available approaches for improving HbA production in the most severe thalassemic specimens, i.e., those individuals with β0/0 phenotype. In this regard, the disclosure provides a demonstration of using ALS10 to modify CD34+ cells from β0/0 phenotype patients such that HbA production is improved relative to a suitable control, and those skilled in the art will recognize suitable controls given the benefit of this disclosure. In embodiments, the control can be a single value or a range of values. For example, a control can be a standardized curve or an area on a graph. In one embodiment the control comprises the increase in HbA produced using a construct described in Breda, L., et al., *Therapeutic hemoglobin levels after gene transfer in beta-thalassemia mice and in hematopoietic cells of beta-thalassemia and sickle cells disease patients*. PLoS One, 2012. 7(3): p. e32345, which is known in the art as "AnkT9W."

In more detail, and without intending to be constrained by any particular theory, the approach of the current disclosure was taken in part in an effort to increase adult hemoglobin in thalassemic and SCD cells in a tissue specific manner, and proportionally to the number of viral molecules inserted. To attempt to reduce genome toxicity believed to be caused by random integration of viral vectors, we strived to maintain viral integration within an average of 2 copies/cell.

Figure 12:
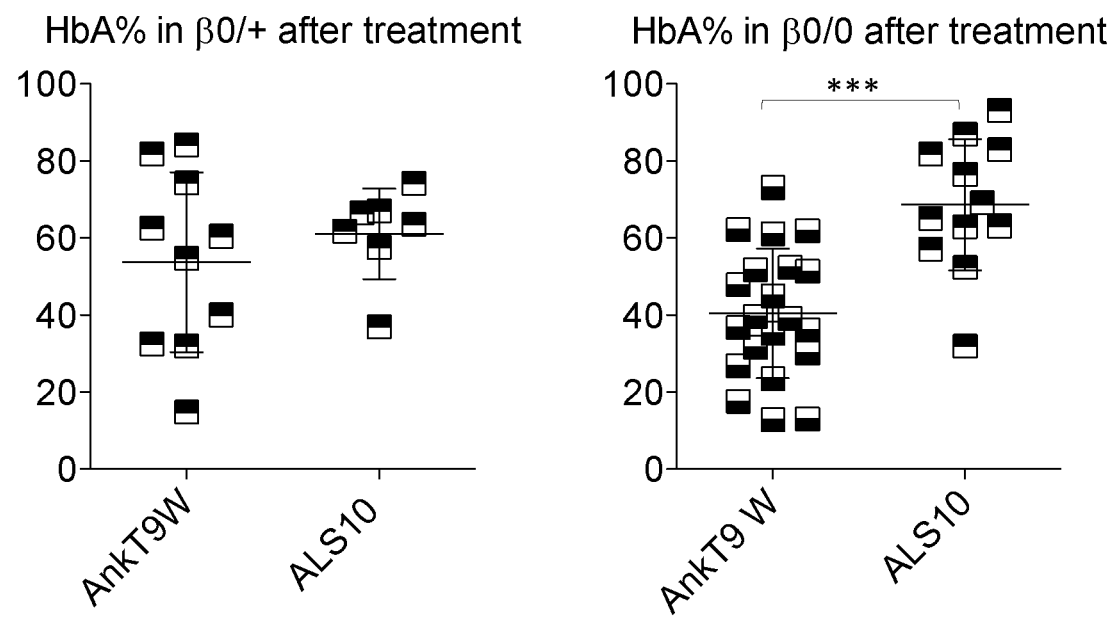
FIG. 12 provides a graphical summary of results comparing adult hemoglobin values (HbA) obtained from β0/+ or β0/0 erythroblasts patient CD34+ cells into which the AnkT9W and ALS10 vectors were introduced, as labeled.

It has been demonstrated in thalassemic specimens with moderate to medium range of HbA reduction (β+/+ and β+/0, respectively) 0.6 copies of AnkT9W were sufficient to generate HbA levels comparable to those detected in healthy or carrier cells, which is about 80-90% (Breda et al, Plos One, 2012). However, in specimens with the most severe phenotype, β0/0, in which no adult HbA is observed, 0.6 copies of AnkT9W could not meet the level of adult hemoglobin observed in healthy or carrier cells, which was a therapeutic threshold that we strived to achieve in the presently provided approach. In connection with this we modified AnkT9W to generate ALS10. In ALS10, the Woodchuck Post-Regulatory Element (WPRE) was eliminated from the integrating sequence to increase the safety of the vector. The WPRE was part of the integrated portion of AnkT9W since it was placed between the LCR and the 3' LTR. The original purpose of the WPRE was to increase the titer of the lentivirus as it had been previously shown to have that effect, but we have now determined that it is dispensable in the current position. WPRE is a viral sequence and is not required for the expression of the beta-globin gene. It is considered safer to limit as much as possible the amount of viral sequences that are integrated in the genome of patient cells. For this reason, we moved this sequence in the vector to the non-integrating region. This preserves the WPRE's ability to produce high titers of viral particles but excludes the WPRE from the genome of patient cells. In order to preserve the ability of WPRE to increase viral titers without having it in the integrating sequence, we removed the WPRE from the integrating portion (before the 3'LTR) and added it back after the 3'LTR so that it is positioned outside the sequence that is integrated in the chromosome(s) of target cells. We also added a strong bovine growth hormone polyA tail after the WPRE region (outlined in FIG. 11). Our data indicate that the modifications do not decrease viral titer during production of compositions of this disclosure. However, we also modified the segment of the construct that results in expression of HbA in erythrocytes that are derived from CD34+ cells into which the lentiviral vector is introduced. In particular, the portion of the beta-globin gene intron 2 that is deleted in the AnkT9W construct is annotated in FIG. 14. As can be seen from that annotation, the beta-globin gene intron 2 encompasses nucleotides 4772-5621, inclusive, and is thus 851 nucleotides in length. However, the intron 2 in AnkT9W comprises a deletion of the 375 nucleotides spanning nucleotides 5,164 through 5,537, inclusive (as designated in FIG. 14). As a consequence of that deletion, the AnkT9W beta-globin gene intron 2 is 476 nucleotides in length. In contrast, and while not intending to be bound by any particular theory, it is considered that including a longer segment of intron 2 in the context of the ALS10 construct is at least partially responsible for the unexpected and statistically significant increase in HbA in the β0/0 patient cells. In this regard, when compared to AnkT9W, ALS10 showed significant improvement and in particular leads to much higher level of HbA in the most severe thalassemic patient specimens, namely, the β0/0 phenotype. It is therefore reasonable expect that the present approach will benefit patients with hemoglobinopathies that are not necessarily due to a β0/0 phenotype, such as SCD. A summary of the results demonstrating this advantage of ALS10 is presented in FIG. 12. The disclosure thus includes lentiviral vectors and cells comprising them, and the integrated construct, wherein the beta-globin gene comprises an intron 2 of more than 476 nucleotides in length, and up to 851 nucleotides in length. The intron is accordingly between 477-875 nucleotides, inclusive, and including all integers and ranges of integers there between. The intron 2 can be thus comprise or consist of 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851 nucleotides. The polynucleotide sequence of the human beta globin gene is depicted in FIG. 13. It includes the 3' enhancer element, the 3' untranslated region (UTR), the polyA signal, exon 3, intron 2, exon 2, intron 1, exon 1, the 5' UTR, and the beta globin promoter segment. It is shown in the 3'-5' orientation because, as is well known in the art, it is anti-parallel to the depicted remainder of the construct and is expressed only after integration and in the context of a double stranded DNA region wherein one strand of the DNA comprises the beta globin gene sequence presented in FIG. 14

In ALS10 the sequence of the beta-globin gene is also modified to increase its ability to prevent the sickling of the sickle-beta-globin chains (referred to as "B-globinM" in FIG. 11). This mutant beta-globin is known as the βT87Q form, due to its amino acid substitution at the 87th position. βT87Q has been used to improve hematological parameters of the SAD and BERK mouse models of SCA (Pawliuk, R., et al. Correction of sickle cell disease in transgenic mouse models by gene therapy. *Science* 294, 2368-2371. (2001)). This form was also used in the first successful clinical trial to correct a patient with β0/βE thalassemia (Cavazzana-Calvo, M., et al. Transfusion independence and HMGA2 activation after gene therapy of human beta-thalassaemia. *Nature* 467, 318-322 (2010)).

The ankyrin insulator that is well known in the art and was present in AnkT9W is also present in ALS10. ALS10 has the ankyrin insulator in the 3'LTR, while the vector AnkT9W has the ankyrin insulator between the promoter and the LCR.

In one aspect of this disclosure, an intron of the beta-globin gene, or other locations such as the 3'UTR, can be modified to include a polynucleotide that targets and decreases the synthesis of the transferrin receptor 1 (TR1). The rational of this approach is based on our observations that decreased erythroid iron intake can be beneficial in beta-thalassemia and, potentially other hemoglobinopathies, because this decreases formation of heme molecules. Heme is normally included in hemoglobin molecules but in many hemoglobinopathies, due to the reduction in synthesis of beta-globin chains, there is an excess of heme not bound to hemoglobin, and these molecules are toxic to red cells. An excess of heme is responsible for apoptosis of erythroblasts and for altering the intracellular content, production of reactive oxygen species (ROS), and for reducing membrane stability and plasticity of erythrocytes, leading to their reduced lifespan, hemolysis and/or sickling. A combination vector that expressed gamma-globin and concurrently knocked-down sickle beta-globin via small hairpin RNA has been described (Samakoglu, S., et al. A genetic strategy to treat sickle cell anemia by coregulating globin transgene expression and RNA interference. *Nature biotechnology* 24, 89-94 (2006)) and this approach can be incorporated in embodiments of the present disclosure (i.e., FIG. 11, in ALS-10T, signified by "I1 S"). With respect to polynucleotides that target TR1 and that can be included in vectors of this disclosure, shRNA is one non-limiting example of an RNAi-mediated approach. But RNAi-based inhibition can be achieved using any suitable RNA polynucleotide that is targeted to TR1 mRNA. With respect to shRNAs, they are known in the art to adopt a typical hairpin secondary structure that contains a paired sense and antisense portion, and a short loop sequence between the paired sense and antisense portions. shRNA is delivered to the cytoplasm where it is processed by DICER into siRNAs. siRNA is recognized by RNA-induced silencing complex (RISC), and once incorporated into RISC, siRNAs facilitate cleavage and degradation of targeted mRNA. In embodiments, an shRNA polynucleotide segment or DNA segment encoding it included for use in suppressing TR1 expression can comprise or consist of between 45-100 nucleotides, inclusive, and including all integers between 45 and 100. The portion of the shRNA that has reverse complementarity to the TR1 mRNA mRNA can be from 21-29 nucleotides, inclusive, and including all integers between 21 and 29. In another approach, a ribozyme that can specifically cleave TR1 mRNA can be included. In another embodiment, microRNA (μRNA) targeted to the TR1 mRNA can be used.

The present disclosure provides an illustration that vector encoding a fusion of an Ldb1 transcription factor and a zinc finger (ZF) domain (ZF-Ldb1) is useful for approaching certain hemoglobinopathies. A ZF-Lbd1 gene can be incorporated into vectors of this disclosure in several configurations. In one non-limiting approach using ALS-10 in FIG. 11 as a representative example, the ZF-Ldb1 gene can be positioned such that the vector comprises consecutively (with the same stranded-ness as the beta-globin coding sequence) the 5'LTR, a polyadenylation signal, the ZF-Ldb1 region and a either a promoter that can drive expression of a separate mRNA encoding the ZF-Ldb1 protein, or an IRES so that the mRNA encoding the ZF-Ldb1 protein can be made as a distinct protein, but from the same mRNA that encodes the beta-globin protein. The rational for including ZF-Ldb1 into ALS is twofold: 1) the ZF-Ldb1 will move the LCR from the promoter of the mutant beta-globin gene to that of the gamma-globin gene. In this way the production of mutant RNA will be reduced or shut down, while expression of the functional gamma-globin gene will be activated: 2) The expression of transgenic beta-globin gene (considered to be a potentially curative gene carried by the lentiviral vector) will not be affected in the presence of ZF-Ldb1. Without intending to be constrained by theory this is expected to lead to an additive or synergistic effect by the production of both hemoglobins: fetal hemoglobin (HbF, α2γ2, from the endogenous locus), and adult hemoglobin (HbA or α2β2, from the therapeutic vector). As hemoglobinopathies in humans are characterized by more than 300 mutations, it is reasonable to predict that the many or all hemoglobinopathies could be improved by a vector of this disclosure. In this regard, we demonstrated that a lentiviral vector encoding the ZF-Ldb1 cassette (pCL-ZF-Ldb1) increases synthesis of fetal hemoglobin (HbF, α2γ2) in CD34-derived erythroid cells from normal individuals and SCA patients. As HbF increased, the synthesis of adult hemoglobin (HbA) or sickle hemoglobin (HbS or α2βs2) diminished, respectively in cells derived from normal individuals or SCA patients. We also investigated the number of vectors integrated per cell, on average. This number is indicated as number of integration per cell or vector copy number (VCN). We observed that the increase in VCN was associated with an increase of HbF both in normal and SCA cells. The number of HbF positive cells measured by flow cytometry also increased proportionally to the VCN. β, γ- and α-globin mRNA levels measured by quantitative PCR also showed that the relative ratio γ/α increased while the β/α or βS/α were reduced in the samples treated with the ZF-Ldb1 vector. Taken together these data suggest that the ZF-Ldb1 can redirect the LCR enhancing effect from the β-globin promoter to the γ-globin promoter. In SCA this effect is particularly beneficial given the toxicity caused by the accumulation of HbS. Examples 1-6 further confirm potential usefulness of including ZF-Ldb1 in ALS10. In particular, these Examples demonstrate infection of hematopoietic stem cells isolated from blood of SCD patients with a lentivirus expressing the ZF-Ldb1 transgene and differentiation of them into mature erythroid cells in vitro. HbF synthesis induced by ZF-Ldb1 was compared to that obtained in specimens treated with hydroxyurea and various additional HbF inducers. ZF-Ldb1 increased HbF synthesis and simultaneously reduced sickle Hb (HbS), establishing a balanced synthesis between α- and functional β-like globins. The induction of HbF in cells treated with ZF-Ldb1 was roughly three times higher (+34%), than that observed using decitabine and pomalidomide; tranylcypromine had an intermediate effect, while butyrate and hydroxyurea showed marginal HbF induction. Notably, erythroid cell differentiation and viability remained unaltered in ZF-Ldb1 expressing cells. Thus, lentiviral-mediated ZF-Ldb1 gene transfer appears superior to existing drug regimens for affecting SCD erythroid cells and it is reasonable to expect that combining ZF- to an ALS10 vector will provide an effective approach to prophylaxis and/or therapy of a variety of hemoglobinopathies. The Examples provide also provide a demonstration of the effectiveness of ALS10 in β0/0 patient cells.

Compositions comprising recombinant lentiviral vectors are provided. In certain approaches pharmaceutical compositions are provided and can be prepared by mixing, for example, virions comprising a lentiviral vector of this disclosure and any suitable pharmaceutically acceptable carriers, excipients and/or stabilizers. Some examples of compositions suitable for mixing with IL-8 can be found in: Remington: The Science and Practice of Pharmacy (2005) 21st Edition, Philadelphia, Pa. Lippincott Williams & Wilkins. In certain approaches.

The disclosure includes methods of making a virion preparations for use in prophylaxis and/or therapy of hemoglobinopathies. In one embodiment this method comprises introducing a plasmid encoding a lentiviral vector of this disclosure into packaging cells. The packaging cells comprise a DNA packaging plasmid, which encodes at least one virion protein, and a DNA envelope plasmid, which encodes a suitable viral envelope protein. The packaging and envelope plasmids express the respective proteins, which facilitate formation of virions which comprise a recombinant RNA lentiviral vector of this disclosure. Suitable packaging systems that can be adapted to produce virions of this disclosure are commercially available, such as from Addgene (Australia).

The following Examples are intended to illustrate various aspects of the present disclosure but are not meant to be limiting in any way.

Example 1

This Example demonstrates that lentivirally expressed ZF-Ldb1 raises HbF levels in CD34+-derived sickle erythroblasts. To obtain the data presented here, we used the lentiviral vector pCL-ZF-Ldb1, (FIG. 11, top vector map), which carries a zinc-finger protein that specifically binds the γ-globin promoters, fused to the self-association (SA) domain of Ldb1, as well as a green fluorescent protein under the control of the erythroid specific ankyrin promoter. The effects of ZF-Ldb1 expression on chromatin contacts within the β-globin locus have been shown using 3C experiments in healthy adult erythroblasts. ZF-Ldb1 expression promotes the juxtaposition of the γ-globin promoters with the LCR leading to transcription [Deng, W., et al., Reactivation of developmentally silenced globin genes by forced chromatin looping. Cell, 2014. 158(4): p. 849-60]. This is accompanied by a concomitant reduction in the expression of adult globin genes, compatible with a mechanism in which the fetal and adult promoters compete for LCR enhancer activity. This example describes an attempt to improve the amount of functional hemoglobin in CD34+ cells isolated from sickle cell patients. Sickle CD34+ cells produce predominantly HbS ($\alpha 2\beta s2$) once differentiated into erythroblasts in vitro. Other hemoglobins, as HbF ($\alpha 2\gamma 2$) and HbA2 ($\alpha 2\delta 2$) are also produced to a lower degree (FIG. 1A, left). Following infection with pCL-ZF-Ldb1 vector, sickle cells dramatically increased HbF synthesis in a manner proportional to the copy number of viral integrants. In a representative experiment the same SCD derived erythroid cells (shown in FIG. 1A, left) transduced with 0.26 or 0.67 viral molecules on average per cell (VCN or vector copy number) produce 22% or 44% (FIG. 1A, middle and right, respectively) more HbF than the control sample. Concomitantly, with progressively higher viral integration the number of HbF (FIG. 1B) and GFP (FIG. 1C) expressing erythroblasts increased, as determined by flow cytometry measurements. The gain in the fraction of GFP+ cells is somewhat lower, likely the result of reduced translation efficiency that is often observed downstream of the internal ribosomal entry site (IRES) between the ZF-Ldb1 cassette and the GFP gene.

Example 2

This Example demonstrates that transgenic ZF-Ldb1 supports high levels of fetal globin induction and concurrently reduces sickle globin levels in SCD erythroblasts. In particular, we analyzed the mRNA and protein content of erythroblasts derived from 10 SCD subjects. CD34+ cells isolated from peripheral blood mononuclear cells (PBMCs) were frozen and used for independent replicate experiments. Infection with pCL-ZF-Ldb1 was performed on pro-erythroblast within the first 10 days of the expansion phase. At this time cells still express high levels of CD1117 and CD44 markers and do not express glycophorin A (data not shown) (Breda, L., et al., Therapeutic hemoglobin levels after gene transfer in beta-thalassemia mice and in hematopoietic cells of beta-thalassemia and sickle cells disease patients. PLoS One, 2012. 7(3): p. e32345).

To assess the ability of ZF-Ldb1 to reactivate HbF we measured the amount of γ-globin mRNA expressed in cells untreated or after transduction. These values were normalized to GAPDH and to α-globin gene expression whose expression is directly proportional to the erythroid differentiation stage in the cells. Cells with 1.1 copies of pCL-ZF-Ldb1 produced on average a 3-fold increase of the γ/α globin ratio (from 0.2±0.11 to 0.6±0.33), compared to untreated cells and, simultaneously, a reduction of the β/α ratio (from 0.38±0.08 to 0.29±0.16) (FIG. 2A, left and center), confirming the ability of the ZF-Ldb1 construct to partially redirect the LCR from the β- to the γ-globin promoter. These changes were observed only in cells expressing transgenic Ldb1, whose expression was proportional to the level of ZF-Ldb1 integration (FIG. 2A, right).

Figure 2:
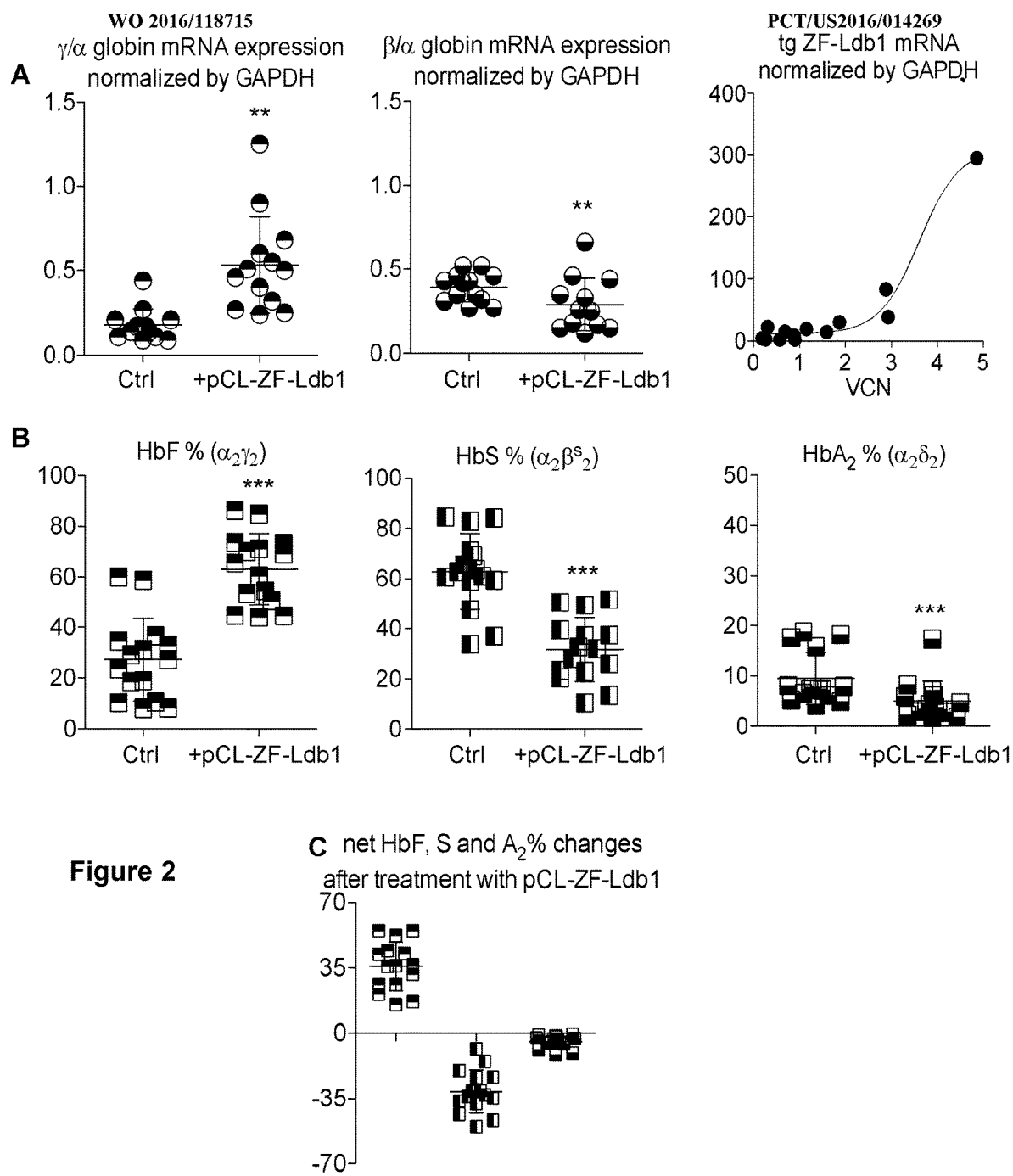
FIG. 2. pCL-ZF-Ldb1 supports high levels of γ-globin/hemoglobin F induction and concurrently reduces sickle globin levels in sickle cell disease (SCD) erythroblasts. (A) β-like globin mRNA content (γ, left, and βs, middle) was measured by Q-PCR and normalized by endogenous GAPDH expression. β-like globin expression changes were further normalized by α-globin expression (which should remain unchanged and is a measure of differentiation across samples). Right: transgenic ZF-Ldb1 mRNA expression in treated samples is plotted against integration of pCL-ZF-Ldb1. (B) HbF (left), HbS (middle) and HbA2 (right) changes in all SCD samples treated with pCL-ZF-Ldb1 LV. (C) Net HbF % increase and HbS %-A2% decrease.

On average, cells treated with pCL-ZF-Ldb1 produced nearly 40% more HbF (63.10%±14.01) compared to untreated cells (27.27%±16.29) (FIG. 2B, left) and lowered production of HbS (−35.65%) and HbA2 (−5.18%) (FIG. 2B, center and right). Reduction of HbA2 is likely the result of reduced contact frequencies between □-globin and the LCR in the presence of ZF-Ldb1. A summary of net HbA increase and HbS and HbA2 decrease is provided in FIG. 3C.

Example 3

Figure 3:
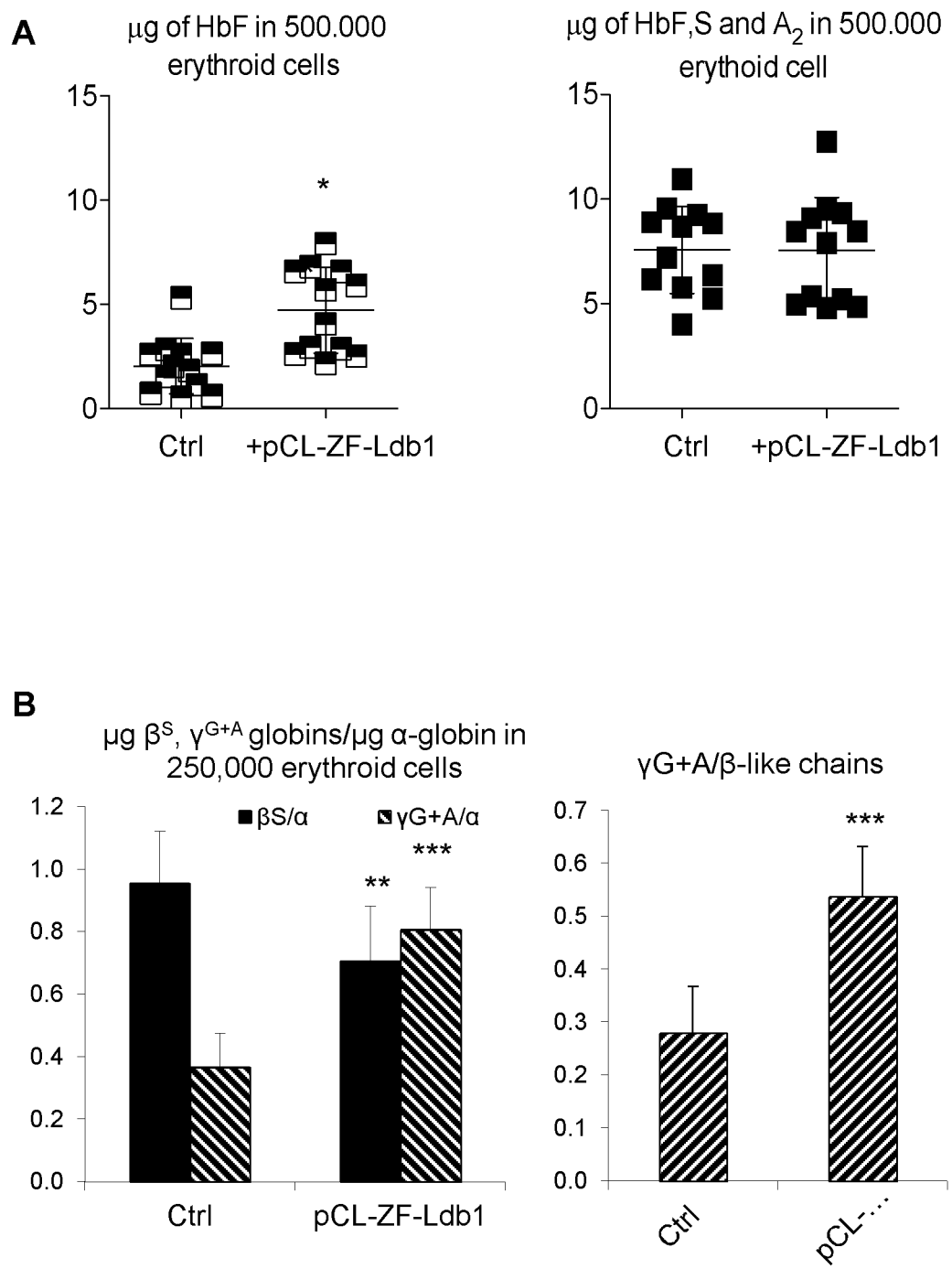
FIG. 3. Quantification of tetrameric Hbs and single globin chains in SCD cells untreated and treated with pCL-ZF-Ldb1. (A) Content of HbF increase (left) and all Hbs (right) in erythroid cells without or with pCL-ZF-Ldb1. (B) Single globin quantification by liquid chromatography in denaturing conditions. On left, the quantity of single β- and γ-globin chains (μg) is calculated over the quantity of single α-globin chain. On right, means of γA+G chains/all β-like chains area indicated. μg of Hbs or single globin chains in hemolysates were extrapolated from calibration curves obtained with standard samples with known Hb concentration.
Figure 4:
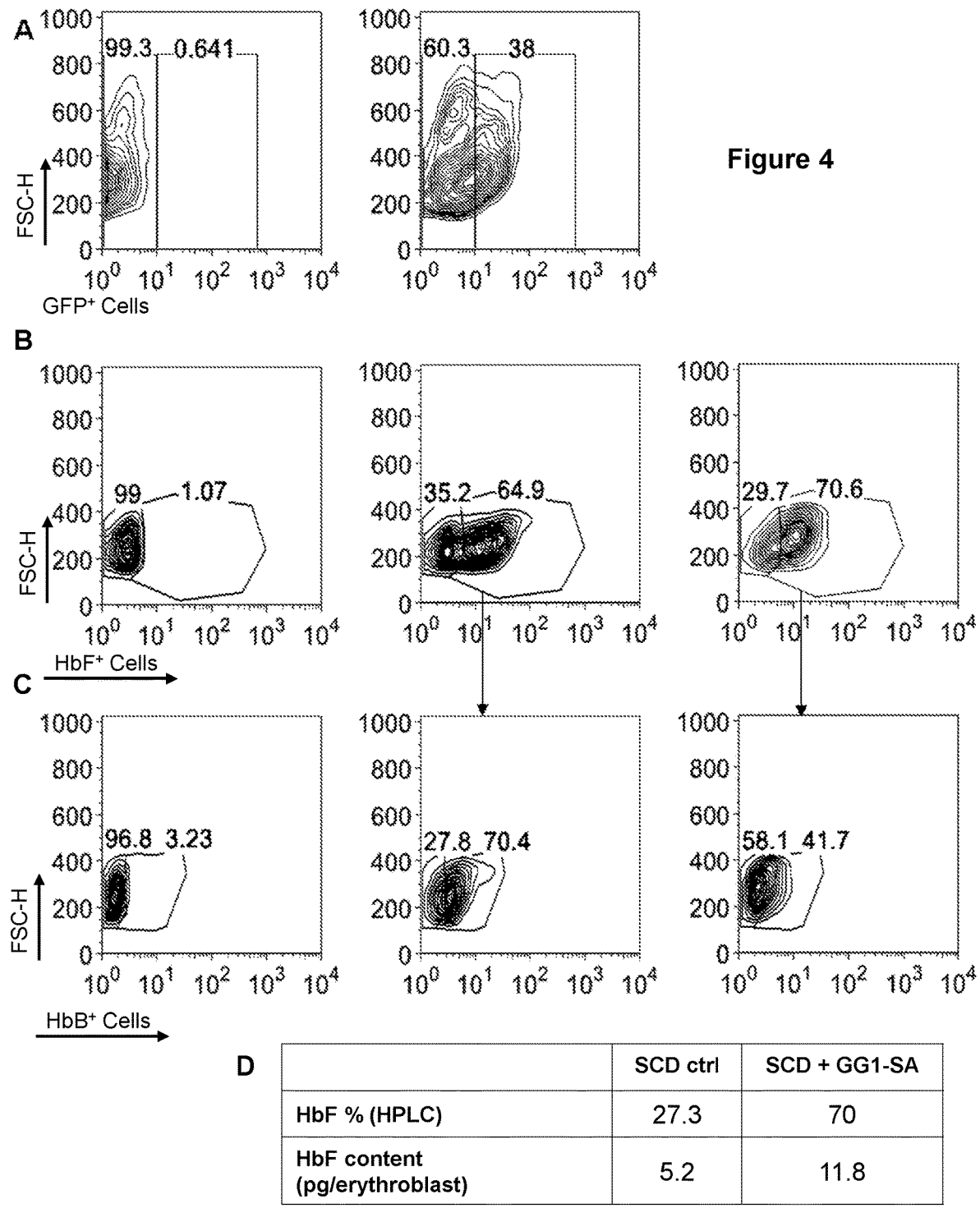
FIG. 4. pCL-ZF-Ldb1-transduced SCD cells expressing HbF have a reduced expression of HbS compared to untransduced cells. (A) The number of GFP expressing SCD erythroblasts after pCL-ZF-Ldb1 integration (right) is compared to untransduced erythroblast (left). (B) Percentage of HbF producing cells in permeabilized erythroblasts (left, no anti-HbF Ab), untransduced (center) and pCL-ZF-Ldb1 transduced (right). (C) β-globin expressing cells within the HbF positive populations from B (center and right) are compared to permeabilized cells (left, no anti-HbB Ab). (D) quantification of HbF of SCD samples (from B) analyzed by HPLC.

To establish the effect of ZF-Ldb1 treatment on the total amount of cellular Hb we measured absolute Hb content per differentiated cell. Importantly, in spite of significant shifts in the ration of fetal to adult globin, total Hb synthesis changes (HbF+HbS+HbA2) remained essentially unaltered (FIG. 3A, right). To corroborate this evidence is the fact that βS chains are diminished while both γA+γG chains are increased in specimens treated with ZF-Ldb1, analyzed by reversed-phase liquid chromatography (FIG. 3B and S1) which allows for the quantification of single globin chains rather than to tetrameric hemoglobin abundance. The reduced amount of HbS was confirmed by flow cytometry (FIG. 4). ZF-Ldb1-expressing SCD erythroblasts, which can be tracked by GFP expression (FIG. 4A), have a greater fraction of HbF positive cells (FIG. 4B), and within the HbF positive population, a lower fraction of HbS compared to untransduced SCD erythroblasts (FIG. 4C). Untreated baseline HbF positive erythroblasts (FIG. 4B, center) were less frequent and contained less than half the HbF/erythroid cell when compared to the ZF-Ldb1 expressing cells (FIG. 4D).

Example 4

Figure 5:
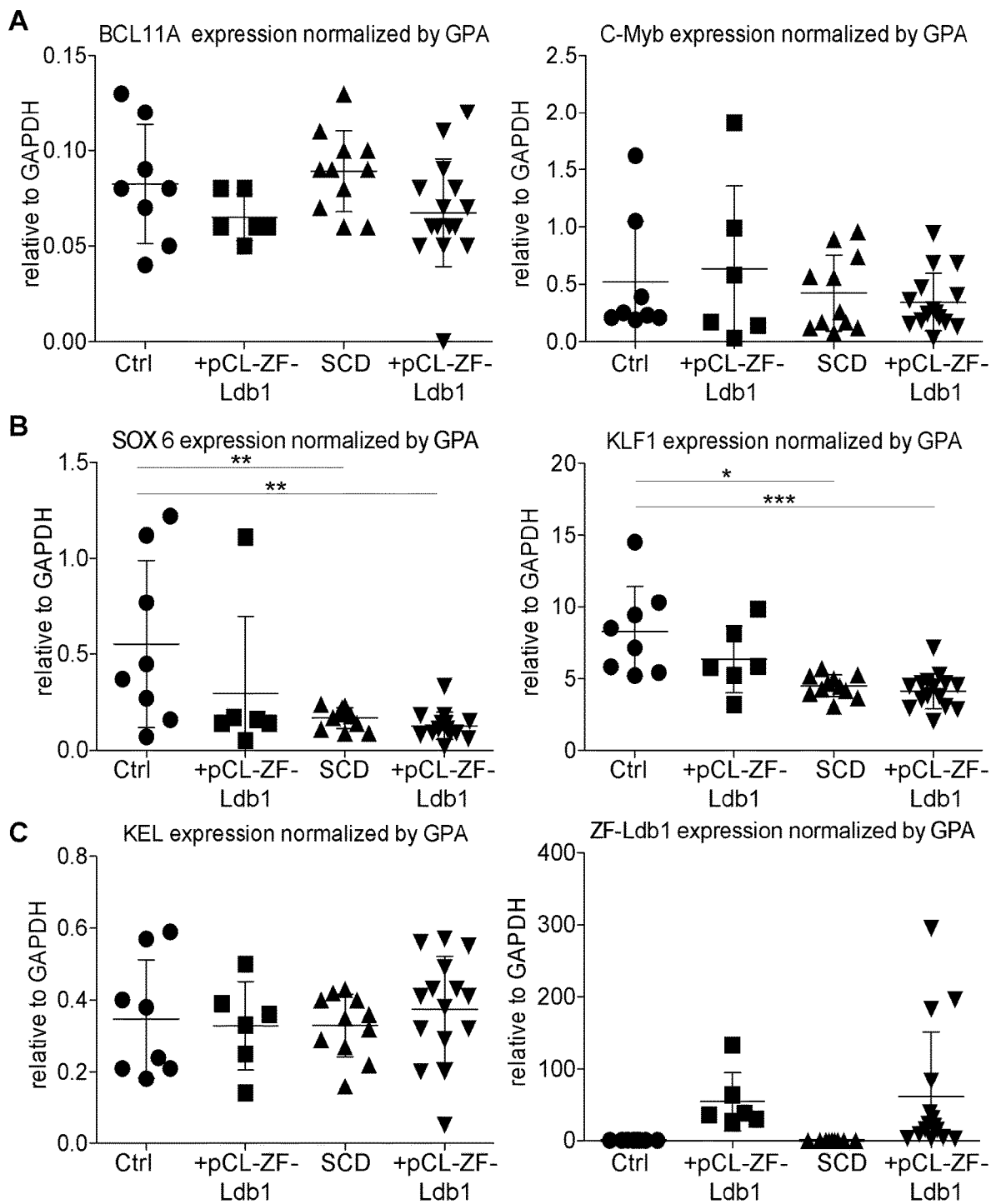
FIG. 5. Expression of γ-globin repressor genes in healthy cells, sickle cells untreated or treated with pCL-ZF-Ldb1 LV. (A) Bcl11A, C-Myb, (B) SOX6 and KLF1 genes' expression is expressed in function of the level of cell differentiation marker glycophorin A (GPA) and normalized by GAPDH expression. The expression of KEL (C, left), the gene that encodes Kell, a blood group antigen, was chosen as internal control. Expression of transgenic Ldb1 in transduced samples (C, right) was confirmed in the same samples analyzed for the other messenger RNAs.
Figure 7:
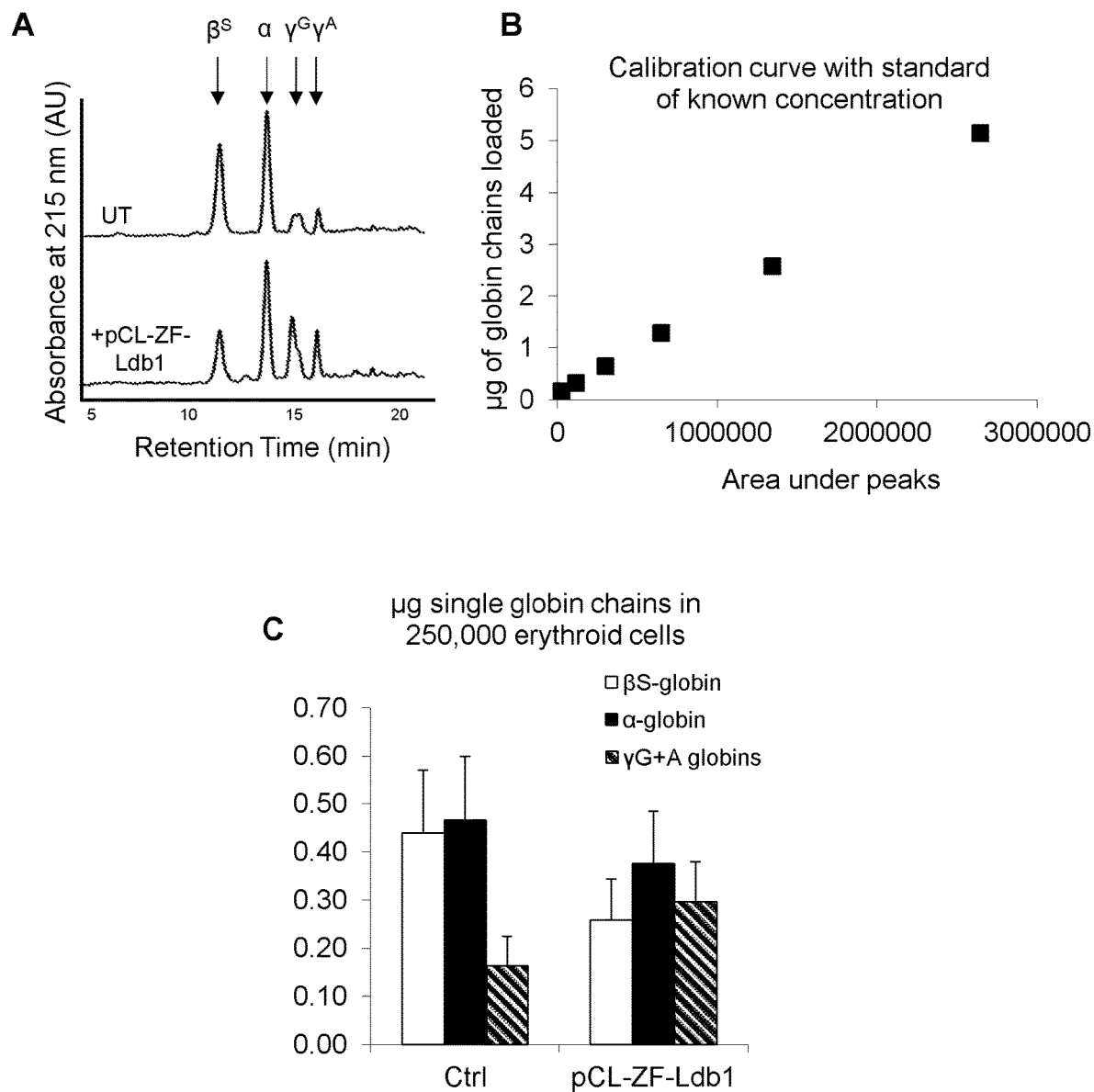
FIG. 7. Differential single globin chain synthesis in cells treated with pCL-ZF-Ldb1. (A) Chromatographic profile of representative sickle cells hemolysate untreated (UT) or treated with pCL-ZF-Ldb1. (B) Calibration curve obtained using known hemoglobin concentration of blood from SCD transgenic mouse. (C) Areas under peak of single globin chains extrapolated from the calibration curve (from B) in samples untreated or after treatment with pCL-ZF-Ldb1 (n=5).
Figure 8:
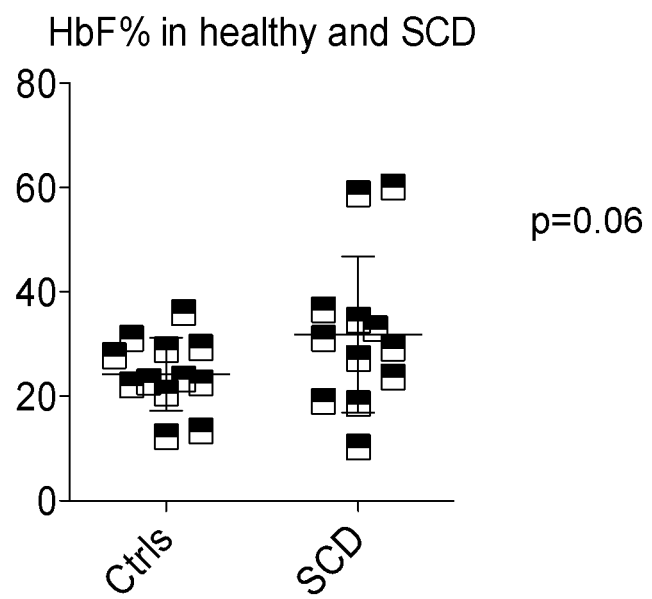
FIG. 8. Trend of moderately elevated HbF levels in CD34+-derived SCD erythroid cells at steady state. Comparative HPLC assessment of HbF % between healthy and SCD erythroid samples in which γ-globin repressors BCl11a, c-Myb, KLF1 and SOX6 were quantified FIG. 9. Cytotoxicity effect and dose/response calibration. Erythroid cells count measurements (benzidine plus count) of cells (N=2) at different doses of drugs in comparison with integration of ~1 copy/cell of GG1-SA. The arrows in black indicate the dose of each drug chosen for the bulk of the experiments.

This Example demonstrates that γ-globin gene repressors SOX6 and KLF1 are down regulated in sickle erythroblasts. In particular, BCL11A, SOX6, C-MYb and KLF1 have emerged as salient repressors of γ-globin during erythroid differentiation. We investigated the impact of pCL-ZF-Ldb1 on transcription of these repressors in both wild type and sickle cell disease derived erythroid cells. RT-qPCR analyses indicates that differentiated erythroblasts obtained from SCD patients present a different pattern of expression for certain negative regulators of γ-globin gene expression, compared to erythroblasts obtained from healthy individuals. BCL11A and C-MYB messenger RNAs present comparable level of expression (FIG. 5A), whereas both KLF1 and SOX6 show significant down regulation in SCD specimens (0.17±0.05 and 4.49±0.76, respectively) compared to healthy ones (0.55±0.43 and 8.29±3.14, respectively) (FIG. 5B). All samples analyzed present similar expression of KEL, an internal control mRNA that increases with level of differentiation. These trends are independent from the level of transgene expression (FIGS. 5 and 5C, right). These data could indicate a more permissive chromatin state of the γ-globin gene in SCD cells in culture, as suggested by a trend of higher content of HbF at steady state in these cells compared to healthy ones (FIG. 7).

Example 5

Figure 6:
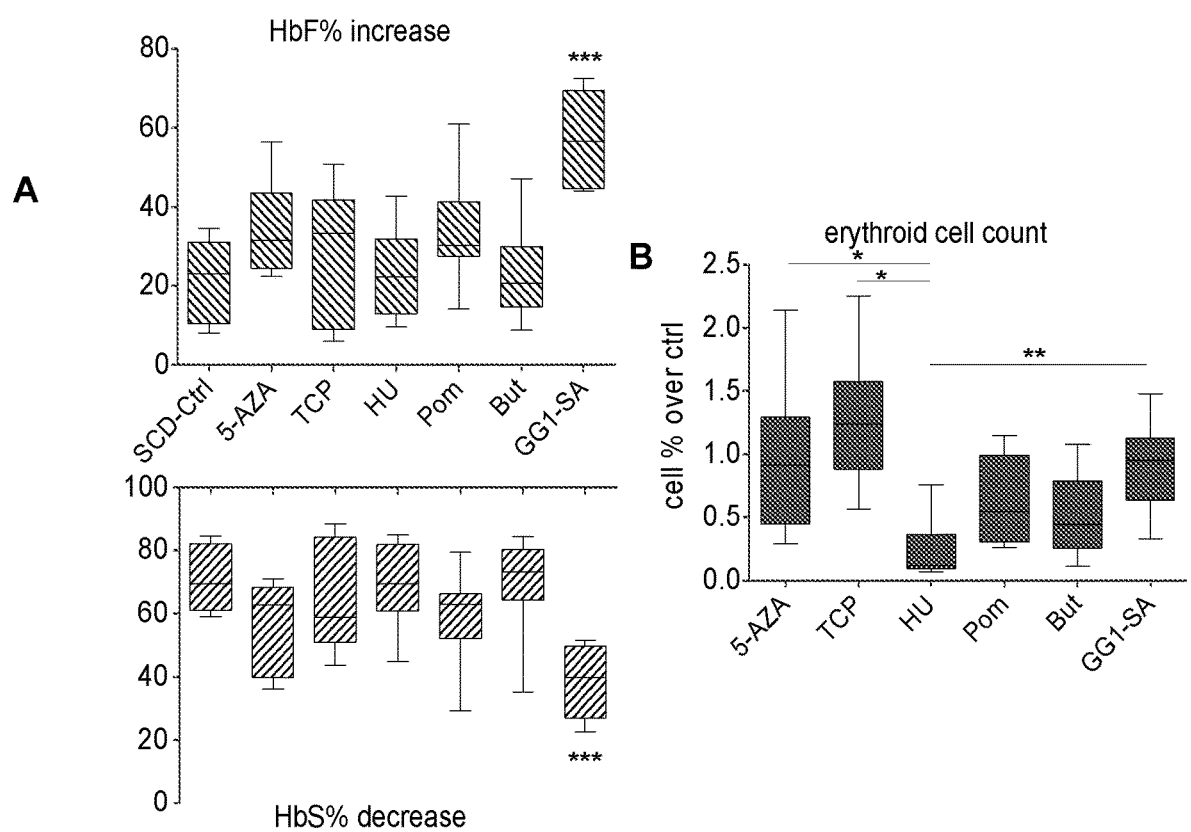
FIG. 6. Hemoglobin F increase/Sickle hemoglobin decrease in CD34+-derived SCD erythroid cells treated with pCL-ZF-Ldb1 LV and with HbF inducers in vitro. (A) (Top) Net increase of HbF % and (bottom) net decrease of HbS % in SCD erythroblasts treated with the HbF inducers decitabine, tranylcypromine, hydroxyurea, pomalidomide, butyrate or with the LV carrying ZF-Ldb1. (B) Erythroid cell count (hemoglobinized cells, or benzidine+ stained cells) for each treatment is been normalized over the untreated sample. In A-B n=11, except for Hu and pCL-ZF-Ldb1 in which n=10, while for But n=9.
Figure 9:
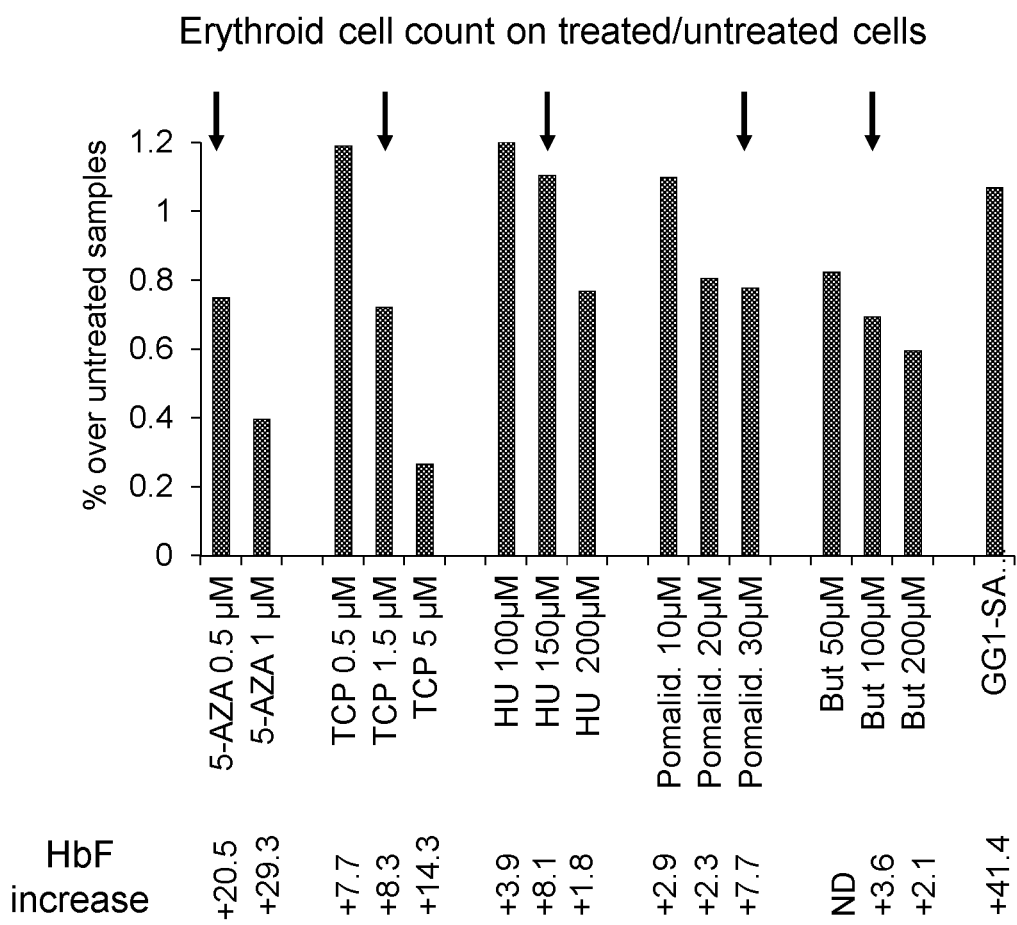
Figure 16:
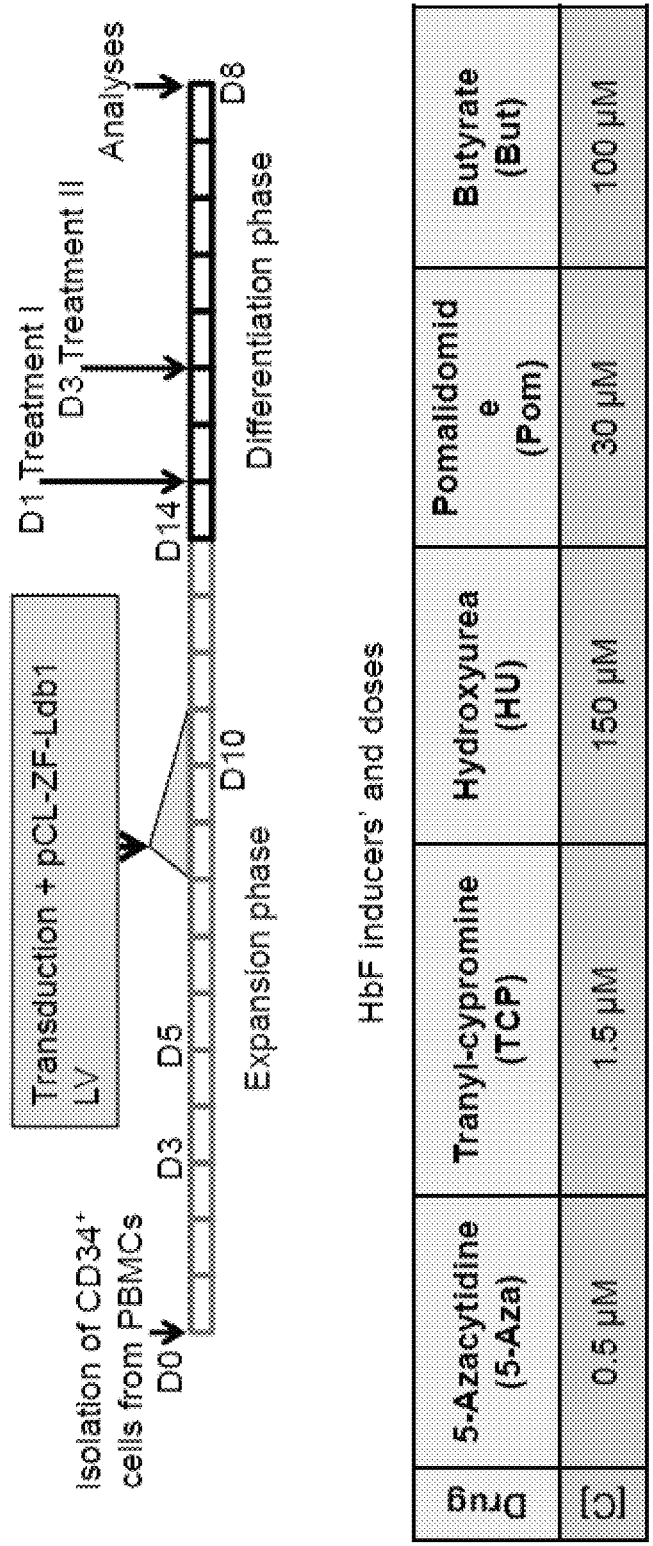
FIG. 16. (Top) Experimental flow for expansion, differentiation and treatment of human SCD CD-34+ cells with pCL-ZF-Ldb1 and/or HbF pharmacological inducers. (Bottom) Type of HbF inducer, biological activity and dose used in the study.

This Example demonstrates that HbF induction in SCD erythroblasts ZF-Ldb1-mediated is greater than induction mediated by pharmacological inducers. A scheme of the experimental procedures is illustrated in FIG. 16. Briefly, erythroid progenitor SCD cells were infected with pCL-ZF-Ldb1 within days 9-11 in expansion phase, or treated at days 1 and 3 of differentiation phase with pharmacological inducers 5-aza-2'-deoxy-cytidine (0.5 μM), tranyl-cypromine (1.5 μM), hydroxyurea (150 μM), pomalidomide (30 μM), and butyrate (100 μM), These concentrations were determined through evaluation of efficacy (net increase of HbF) versus toxicity (cell death); the original scaling dosage was extrapolated from the recent literature (FIG. 9) [Watanapokasin, Y., et al., *In vivo and in vitro studies of fetal hemoglobin induction by hydroxyurea in beta-thalassemia/hemoglobin E patients*. Exp Hematol, 2005. 33(12): p. 1486-92; Moutouh-de Parseval, L. A., et al., *Pomalidomide and lenalidomide regulate erythropoiesis and fetal hemoglobin production in human CD34+ cells*. J Clin Invest, 2008. 118(1): p. 248-58; Shi, L., et al., *Lysine-specific demethylase 1 is a therapeutic target for fetal hemoglobin induction*. Nat Med, 2013. 19(3): p. 291-4]. Studies were performed on day 8 of differentiation phase, at the orthochromatophilic stage when high amounts of hemoglobin were accumulated. As measured by HPLC, pCL-ZF-Ldb1 had the most robust increase of HbF and decrease in HbS. Specifically, on average the net HbF increase in SCD erythroblast treated with the lentivirus was 34.2%±12.53, versus 15.19%±12.77 with 5-aza-cytidine ($p<0.01$), 8.08%±6.28 with tranyl-cypromine ($p<0.001$), 2.39%±2.13 with hydroxyurea ($p<0.001$), 11.84%±9.02 with pomalidomide ($p<0.01$), and 4.84%±5.03 with butyrate ($p<0.001$). ZF-Ldb1 expressing cells presented HbF significantly higher than untreated cells ($p<0.001$) (FIG. 6A, top). Conversely, on average the net HbS decrease in SCD erythroblast treated with the lentivirus was −31.36%±11.61, versus −17.30%±15.04 with 5-aza-cytidine, −6.93%±6.64 with tranyl-cypromine, −3.48%±4.68 with hydroxyurea, 11.61−%±9.27 with pomalidomide, and −4.90%±7.94 with butyrate (FIG. 6A, bottom).

Figure 10:
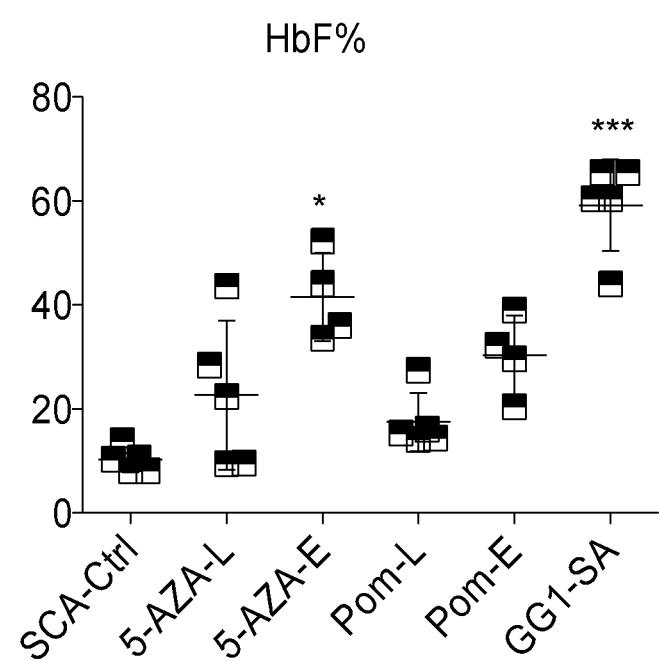
FIG. 10. Variation of HbF % SCD erythroid cells treated with pCL-ZF-Ldb1 vector and with HbF inducers in vitro at different times. Net increase of HbF % in SCD erythroblasts treated with the HbF inducers 5-aza-cytidine or with the LV carrying ZF-Ldb1, according to FIG. 16 (L) and FIG. 17 (E). Kruskal-Wallis with Dunn's multiple comparison test.
Figure 17:
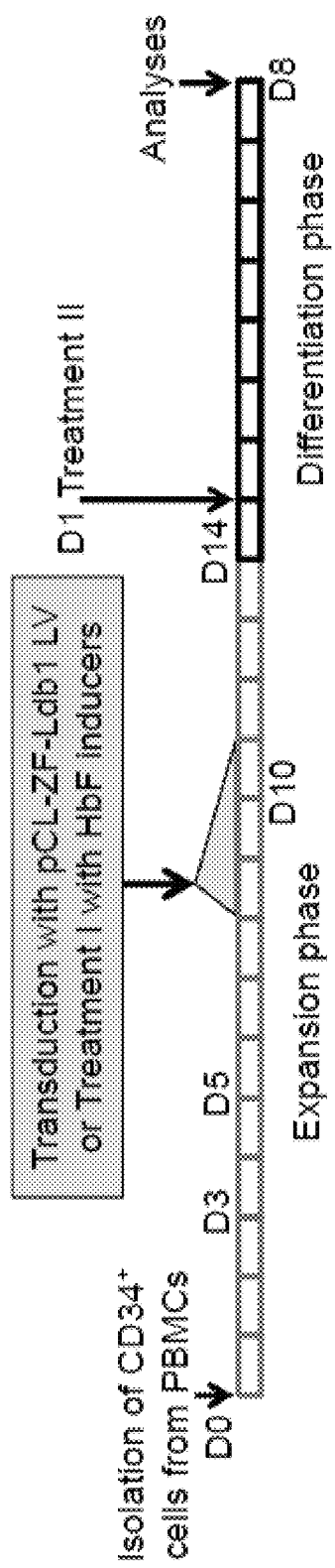
FIG. 17. Experimental flow for expansion, differentiation and treatment of human SCD CD-34+ cells with pCL-ZF-Ldb1 or HbF pharmacological inducers.

Along with recovery of greater levels of functional Hb, cells expressing ZF-Ldb1 did not show significant changes in viability compared to untreated samples, whereas cells treated with pomalidomide, butyrate and hydroxyurea showed reduced viability (FIG. 6B). These differences were confirmed in a subset of samples treated with pharmacological inducers at earlier time points (FIG. 17) to exclude biases due to a delay to drug response (FIG. 10). Taken together, pCL-ZF-Ldb1 was superior to all tested compounds in augmenting HbF and F-Cell levels and importantly was associated with minimal toxicity.

It will be apparent from the foregoing that a lentiviral vector carrying the SA Ldb1 domain linked to a ZF protein, which selectively binds the γ-globin promoters, significantly increased HbF synthesis and exceeds previously described pharmacological inducers. It is therefore reasonable that adding an SA Ldb1 domain linked to a ZF protein to an ALS10 vector of this disclosure will likely enhance beneficial properties of the combined vectors.

Example 6

This Example provides a description of the materials and methods used to obtain the results described in Examples 1-5.

Human and Animal Ethics

Peripheral blood samples from SCD patients were obtained during automated red cell exchange as part of their routine clinical care at Montefiore Medical Center. Since the samples were unlinked and de-identified medical waste, the Montefiore Medical Center Institutional Review Board deemed them to be IRB exempt.

Construct

The ZFs targeting HS2 of the human γ-globin promoters are known in the art. The SA domain containing amino acids 1-200 of Ldb1 was inserted C-terminal to the ZF. The SA domain was attached in C-terminal to GG1 tagged with HA.

Vector Production and Titration

Viral stocks were generated by co-transfection of the gene transfer plasmid (pCL-ZF-Ldb1) together with the envelope plasmid (VSV-G), the packaging plasmid (pMDLg/p RRE), and the pRSV-REV plasmid into 293T cells. An aliquot ($5 \times 10^6$) of 293T cells was seeded into cell culture dishes (10 cm) 24 hours prior to transfection in Iscove's modification of Eagle's medium (DMEM, Cellgro, Manassas, Va.) with 10% fetal bovine serum, 100 U/ml penicillin, and 100 mg/ml streptomycin, at 37° C. under 5% CO2. The culture medium was changed 2 hours prior to transfection. The precipitate was formed by adding the plasmids to 450 uL of 0.1×TE (0.1×TE is 10 mM Tris plus 1 mM EDTA) and 50 µL of 2 M CaCl2, then adding 500 µL of 2×HEPES-buffered saline (281 mM NaCl, 100 mM HEPES, 1.5 mM Na2HPO4) drop wise after which the precipitate was vortexed and immediately added to the cultures. The medium (10 ml) was replaced after 16 hours. Viral supernatants were collected at 24 and 48 hours, cleared by low speed centrifugation, and filtered through cellulose acetate (0.2 µm). Following ultracentrifugation, serial dilutions of concentrated virus (5; 0.5 and 0.05 µL, respectively) were used to infect $1 \times 10^5$ NIH 3T3 cells (ATCC, Manassas, Va.) in 1 mL of transfection buffer complemented with polybrene (Millipore, Billerica, Mass.) at a final concentration of 8 µg/mL. Genomic DNA was extracted after 3 days (Qiagen kit, Valencia, Calif.). The multiplicity of infection (MOI) was calculated using the following formula: number of cells ($1 \times 10^5$) X dilution factor (1 mL/µL viral preparation) X VCN (measured via real-time PCR, using oligos for WPRE element and ID gene, see PCR and Real Time PCR).

Real Time (RT)-PCR

Retrotranscription of total mRNA was done using the SuperScript™ II First Strand Kit (Invitrogen, Carlsbad, Calif.). Q-PCR reactions were performed using the ABI Prism 7700 Sequence Detection System (Applied Biosystems, Foster City, Calif.), with either TaqMan (TaqMan PCR 2× Master mix; Applied Biosystems) or SYBR Green (iTaq™ SYBR® Green Supermix, Bio-Rad Laboratories, Hercules, Calif.) chemistry. Quantitative real-time PCR assays of globin and GAPDH transcripts were carried out using gene-specific double fluorescently labeled probes. The following primer and probe sequences were used (forward, reverse and probe, when used, of each gene, respectively): β: Fw: 5'-CAAGAAAGTGCTCGGTGCCT-3' (SEQ ID NO:6); Rev: 5'-GCAAAGGTGCCCTTGAGGT-3' (SEQ ID NO:7); 5'-FAM-TAGTGATGGCCTGGCTCACCTGGAC-TAMRA-3' (SEQ ID NO:8); α: Fw: 5'-TCCCCACCAC-CAAGACCTAC-3' (SEQ ID NO:9); Rev: 5'-CCT-TAACCTGGGCAGAGCC-3' (SEQ ID NO:10); 5'-FAM-TCCCGCACTTCGACCTGAGCCA-TAMRA-3' (SEQ ID NO:11); γ: Fw: 5'-TGGCAAGAAGGTGCTGACTTC-3' (SEQ ID NO:12); Rev: 5'-TCACTCAGCTGGGCAAAGG (SEQ ID NO:13); 5'-FAM-TGG GAGATGCCAT-AAAGCACCTGG-TAMRA-3 (SEQ ID NO:14)'; BCL11A: Fw: 5'-TGATGTGTGTCCATTGGTGTGAGC-3' (SEQ ID NO:15); Rev: 5'-TGCGAACTTGAACGTCAGGAGTCT, SOX-6 (SEQ ID NO:16): Fw: 5'-AGCTGCTTTCGGCTTTCTCCCTTA-3' (SEQ ID NO:17); Rev: 5'-CCTTTGCATTTGCAGCAGTTCAGC-3' (SEQ ID NO:18); C-MYB: Fw: 5'-TCAACCGAT-CATCCCTCACACTCT-3' (SEQ ID NO:19)'; Rev: 5'-AATCAGCAGCGCTTCCATTCAAGG-3" (SEQ ID NO:20), KLF-1: Fw: 5'-GCTGCCTCCACCCAAGTG-3' (SEQ ID NO:21); Rev: 5'-ACCAACTCTGGGCAGTCA-CAT-3' (SEQ ID NO:22), Kell: Fw: 5'-AGCAACCACC-CATGCCTGCC-3' (SEQ ID NO:23); Rev: 5'-CTCGGGC-CAAAGGCCTCACG-3' SEQ ID NO:24). For real-time PCR of the reference genes, we used as an endogenous control the human glyceraldehyde-3-phosphate dehydrogenase (GAPDH) kit, in which the probe is fluorescently labeled with VIC (Applied Biosystems). The number of integrations (VCN) was quantified by Q-PCR using oligos (Fw: 5'-CGGCTGTTGGGCACTGA-3' SEQ ID NO:25); Rev: 5'-GGAAGGTCCGCTGGATTGA-3' SEQ ID NO:26)) and a probe (5'-FAM-ATGGCTGCTCGCCTGTGTTGCC-TAMRA-3' SEQ ID NO:27) for a specific sequence present in the vector (WPRE) and compared it to an endogenous control present in two copies within the genome (ID-1 Fw: 5'-AAGGT-GAGCAAGGTGGAGATTC-3 SEQ ID NO:28)'; Rev: 5'-TTCCGAGTTCAGCTCCAACTG-3' SEQ ID NO:29).

Two-Phase Liquid Cultures, Benzidine Staining and Transduction

CD34+ cells selection from blood samples was performed by immunomagnetic separation, using the CD34 microbeads kit (Miltenyi Biotec Inc., Auburn, Calif.). These cells were then expanded following a modified version of the protocol described by Leberbauer and colleagues. Cells were seeded in 5 mL of serum-free StemSpan with 50 µL of StemSpan CC-100 cytokine cocktail (both from Stemcell Technologies, Vancouver, BA, Canada), 2 U/mL Erytrhopoietin (Amgen, Thousand Oaks, Calif.), 10-6 M dexamethasone (Sigma) and 1% penicillin streptomycin. CD34+ cultures were kept undifferentiated by refreshing the medium twice a week and density gradient centrifugation was used to remove both dead and spontaneously differentiating cells. At this stage cells were either frozen (with 50% characterized Hyclone FBS, 10% DMSO, Sigma, and 40% Iscove's Modified DMEM, Cellgro), or used for experiments. After 10 days in phase I, cells were transferred into phase II media containing α-modified essential medium supplemented with 30% fetal calf serum and 10-5 M β-mercaptoethanol. Erythropoietin was added (5 U/mL) to stimulate erythroid differentiation. Cells were infected with serial dilutions of the virus. Cells were collected on day 7-10 of phase II for all analyses. The level of differentiation was assessed by benzidine staining. At this stage, cells were analyzed by flow cytometry for GFP, HbF and HbB expression.

Treatment with HbF Inducers

We treated peripheral blood derived CD34+ cells (see procedure) with HbF inducer drugs: Hydroxyurea (HU), 5-azacytidine, pomalidomide, sodium butyrate, Tranyl-cypromine (TCP). Tranyl-cypromine (TCP), 5-aza-2'-deoxycytidine, pomalidomide and sodium butyrate. We first titrated the drugs to find the most efficient and less toxic concentration according to published data. Hydroxyurea (HU; Sigma-Aldrich), dissolved in water, was added to the culture medium at final concentrations of 150 µM. Tranyl-cypromine (Sigma-Aldrich) was dissolved in water and added to the culture medium at final concentrations 1.5 µM. 5-azacytidine (DAC; Sigma-Aldrich) was dissolved in water and added to the culture medium at final concentrations of 0.5 µM. Pomalidomide (Sigma-Aldrich) was dissolved in DMSO and was added to the culture medium at final concentrations of 30 µM. Sodium butyrate (Sigma-Aldrich) was dissolved in water and added to the culture medium at final concentration of 100 µM. The treatment timeline is shown in FIG. 16.

Tetrameric and Single Chain Analysis by High Performance Liquid Chromatography (HPLC)

Red cell pellets were lysed with HPLC-grade water, and the resulting membrane-free hemolysates loaded into a System Gold 126 Solvent Module instrument (Beckman Coulter, Fullerton, Calif.). Hemoglobins were separated on a weak cation-exchange PolyCAT A column (PolyLC, Inc, Columbia, Md.), and detected at a wavelength of 415 nm. The Hbs were bound to the column with mobile phase A (20 mmol/L Bis-Tris, 2 mmol/L KCN, pH 6.96) and eluted with mobile phase B (20 mmol/L Bis-Tris, 2 mmol/L KCN, 200 mmol/L NaCl, pH 6.55). Single chain quantification was assessed via reversed-phase HPLC. Hb samples in this case were injected on a Hitachi D-7000 HSM Series apparatus (Hitachi Instruments, San Jose, Calif.) using a Zorbax 5 µm 300SB-C8 300 Å, LC 150×2.1 mm column (Agilent Technologies, Santa Clara, Calif.) and a gradient from 20% to 60% acetonitrile in 0.1% trifluoroacetic acid in 25 minutes, with UV detection at 215 nm. Serial dilutions of a solution with known concentrations of HbA and HbF (Analytical Control System, Inc, Fishers, Ind.) were used to generate a calibration curve, where the peak areas were plotted against the concentration values. Types and relative quantity of Hbs in samples were assessed by comparison to standard hemoglobin controls.

Example 7

This Example demonstrates that introducing the lentiviral vector ALS10 into CD34+ cells from β0/0 phenotype samples, and thus the most severe thalassemic specimens, results in statistically significantly elevated levels of HbA produced by erythrocytes derived from the modified CD34+ cells. The elevation in HbA is relative to a previously describe construct, which is used in this Example as a comparison control (AnkT9W, from Breda et al, Plos One, 2012), which did not include a complete intron 2. Thus, when compared to the previously described construct, ALS10 showed significant and unexpected improvement, as demonstrated by the results depicted in FIG. 12. To obtain the results presented in FIG. 12, the following materials and methods were used.

Vector Production and Titration

Viral stocks were generated by co-transfection of the gene transfer plasmid (GG1-SA) together with the envelope plasmid (VSV-G), the packaging plasmid (pMDLg/p RRE), and the pRSV-REV vector into 293T cells. An aliquot ($5 \times 10^6$) of 293T cells was seeded into cell culture dishes (10 cm) 24 hours prior to transfection in Iscove's modification of Eagle's medium (DMEM, Cellgro, Manassas, Va.) with 10% fetal bovine serum, 100 U/ml penicillin, and 100 mg/ml streptomycin, at 37° C. under 5% CO2. The culture medium was changed 2 hours prior to transfection. The precipitate was formed by adding the plasmids to 450 uL of 0.1×TE (0.1×TE is 10 mM Tris plus 1 mM EDTA) and 50 µL of 2 M CaCl2, then adding 500 µL of 2×HEPES-buffered saline (281 mM NaCl, 100 mM HEPES, 1.5 mM Na2HPO4) dropwise after which the precipitate was vortexed and immediately added to the cultures. The medium (10 ml) was replaced after 16 hours. Viral supernatants were collected at 24 and 48 hours, cleared by low speed centrifugation, and filtered through cellulose acetate (0.2 µm). Following concentration by ultracentrifugation, serial dilutions of concentrated virus (5; 0.5 and 0.05 µL, respectively) were used to infect $1 \times 10^5$ NIH 3T3 cells (ATCC, Manassas, Va.) in 1 mL of transfection buffer complemented with polybrene (Millipore, Billerica, Mass.) at a final concentration of 8 µg/mL. Genomic DNA was extracted after 3 days (Qiagen kit, Valencia, Calif.). The multiplicity of infection (MOI) was calculated using the following formula: number of cells ($1 \times 10^5$) X dilution factor (1 mL/µL viral preparation) X VCN (measured via real-time PCR, using oligos for Psi element and ID gene, by Real Time PCR).

Two-Phase Liquid Cultures, Benzidine Staining and Transduction

Consented patients with β0/0 and healthy individuals donated between 20 and 30 mL of peripheral blood; alternatively 30 to 60 mL of peripheral blood from β0/0 patients were obtained from the discarded blood from the red cell exchange therapeutic procedure. We selected CD34+ cells by immunomagnetic separation, using the CD34 microbeads kit (Miltenyi Biotec Inc., Auburn, Calif.) and then expanded these cells following a modified version of the protocol described by Leberbauer and colleagues. Cells were seeded in 5 mL of serum-free StemSpan with 50 µL of StemSpan CC-100 cytokine cocktail (both from Stemcell Technologies, Vancouver, BA, Canada), 2 U/mL Erytrhopoietin (Amgen, Thousand Oaks, Calif.), 10-6 M dexamethasone (Sigma) and 1% penicillin streptomycin. CD34+ cultures were kept undifferentiated by refreshing the medium twice a week and density gradient centrifugation was used to remove both dead and spontaneously differentiating cells. At this stage cells were either frozen (with 50% characterized Hyclone FBS, 10% DMSO, Sigma, and 40% Iscove's Modified DMEM, Cellgro), or used for experiments. After 10 days in phase I, cells were transferred into phase II media containing α-modified essential medium supplemented with 30% fetal calf serum and 10-5 M β-mercaptoethanol. Erythropoietin was added (5 U/mL) to stimulate erythroid differentiation. Cells were infected with serial dilutions of the virus. Cells were collected on day 7-10 of phase II for all analyses. The level of differentiation was assessed by benzidine staining.

High Performance Liquid Chromatography (HPLC)

Cell pellets were lysed with HPLC-grade water and loaded into a System Gold 126 Solvent Module instrument (Beckman Coulter, Fullerton, Calif.). Hemoglobins were separated on a PolyCAT A column (PolyLC, Inc, Columbia, Md.), which is packed with silica-based material with a bonded coating of polyaspartic acid, and detected at a wavelength of 415 nm. The Hbs were bound to the column with mobile phase A (20 mmol/L Bis-Tris, 2 mmol/L KCN, pH 6.96) and eluted with mobile phase B (20 mmol/L Bis-Tris, 2 mmol/L KCN, 200 mmol/L NaCl, pH 6.55). Serial dilutions of a solution with known concentrations of HbA and HbF (Analytical Control System, Inc, Fishers, Ind.) were used to generate a calibration curve, where the absorbance detected at 415 nm was plotted against the concentration values. Types and quantity of hemoglobins in samples were assessed by comparison to standard hemoglobin controls.

While the invention has been described through specific embodiments, routine modifications will be apparent to those skilled in the art and such modifications are intended to be within the scope of the present invention.

What is claimed is:

1. A self-inactivating lentiviral vector for inducing expression of human beta-globin in erythrocytes and/or erythrocyte progenitor cells for use in prophylaxis and/or therapy of a hemoglobinopathy in an individual, the lentiviral vector comprising:

i) a 5' long terminal repeat (LTR) and a self-inactivating 3' LTR;
ii) a first polyadenylation signal;
iii) at least one promoter;
iv) a globin gene locus control region (LCR);
v) an ankyrin insulator element (Ank);

vi) a Woodchuck Post-Regulatory Element (WPRE);
vii) a second polyadenylation signal; and
viii) a sequence that is the reverse complement of a sequence encoding modified adult human beta-globin comprising a βT87Q mutation (B-globinM), wherein the sequence encoding the B-globinM comprises a first intron (intron 1) between exon 1 and exon 2, and a second intron (intron 2) between exon 2 and exon 3 of said B-globinM sequence, wherein intron 2 comprises the full-length of the adult human B-globinM intron 2 sequence;
wherein the lentiviral vector comprises in the 5' to 3' direction: said 5' long terminal repeat (LTR), said sequence that is the reverse complement of a sequence encoding modified adult human beta-globin comprising a βT87Q mutation (B-globinM) under the control of said promoter and linked to said first polyadenylation signal, said globin gene locus control region (LCR), said self-inactivating 3' LTR comprising said ankyrin insulator element (Ank), said Woodchuck Post-Regulatory Element (WPRE), and said second polyadenylation signal.

2. The lentiviral vector of claim 1, wherein the lentiviral vector further comprises a sequence encoding a fusion of LIM domain-binding protein 1 (Ldb1) transcription factor and a zinc finger (ZF) domain.

3. The lentiviral vector of claim 1, wherein the lentiviral vector further comprises a sequence encoding a transferrin receptor 1 microRNA or a shRNA sequence which is capable of decreasing transferrin receptor 1 mRNA in a RNAi-mediated process.

4. The lentiviral vector claim 1, wherein the lentiviral vector is present in CD34+ cells, wherein the CD34+ cells have been separated from an individual who has a hemoglobinopathy.

5. The lentiviral vector of claim 1, wherein the lentiviral vector is present in a virion.

6. The lentiviral vector of claim 1, wherein said second polyadenylation signal is a bovine growth hormone polyadenylation signal.

7. A method of making a viral particle preparation for use in prophylaxis and/or therapy for one or more hemoglobinopathies comprising introducing a plasmid encoding a lentiviral vector of claim 1 into packaging cells which comprise a DNA packaging plasmid which encodes at least one virion protein, and a DNA envelope plasmid which encodes an envelope protein, and allowing expression of the virion protein and the envelope protein such that viral particles form, and separating the viral particles from the packaging cells.

8. A lentiviral vector for inducing expression of human beta-globin in erythrocytes and/or erythrocyte progenitor cells for use in prophylaxis and/or therapy of a hemoglobinopathy in an individual, wherein the lentiviral vector comprises SEQ ID NO: 3.

9. The lentiviral vector of claim 8, wherein the lentiviral vector further comprises a sequence encoding a fusion of LIM domain-binding protein 1 (Ldb1) transcription factor and a zinc finger (ZF) domain.

10. The lentiviral vector of claim 8, wherein the lentiviral vector further comprises a sequence encoding a transferrin receptor 1 microRNA or a shRNA sequence which is capable of decreasing transferrin receptor 1 mRNA in a RNAi-mediated process.

11. The lentiviral vector of claim 8, wherein the lentiviral vector is present in CD34+ cells, wherein the CD34+ cells have been separated from an individual who has a hemoglobinopathy.

12. The lentiviral vector of claim 8, wherein the lentiviral vector is present in a virion.

13. A method for inducing expression of human beta-globin in erythrocytes and/or erythrocyte progenitor cells comprising introducing into erythrocytes and/or erythrocyte progenitor cells the lentiviral vector of claim 8.

14. The method of claim 13, wherein the erythrocyte progenitor cells comprise CD34+ cells.

15. The method of claim 14, wherein the CD34+ cells are from an individual who has a hemoglobinopathy.

16. A method of making a viral particle preparation for use in prophylaxis and/or therapy for one or more hemoglobinopathies comprising introducing a plasmid encoding a lentiviral vector of claim 8 into packaging cells which comprise a DNA packaging plasmid which encodes at least one virion protein, and a DNA envelope plasmid which encodes an envelope protein, and allowing expression of the virion protein and the envelope protein such that viral particles form, and separating the viral particles from the packaging cells.

17. An ex vivo method for inducing expression of human beta-globin in erythrocytes and/or erythrocyte progenitor cells comprising introducing into erythrocytes and/or erythrocyte progenitor cells the lentiviral vector of claim 1.

18. The method of claim 17, wherein the erythrocyte progenitor cells comprise CD34+ cells.

19. The method of claim 18, wherein the CD34+ cells are from an individual who has a hemoglobinopathy.

* * * * *